(12) United States Patent
Moghaddam et al.

(10) Patent No.: US 12,194,014 B2
(45) Date of Patent: Jan. 14, 2025

(54) PLATINUM-BASED AMPHIPHILE PRODRUGS

(71) Applicant: NANOMED HOLDINGS PTY LTD, Lane Cove West (AU)

(72) Inventors: Minoo Jalili Moghaddam, Lane Cove West (AU); Xiaojuan Gong, Lane Cove West (AU); Ross Cyril Smith, Lane Cove West (AU)

(73) Assignee: NANOMED HOLDINGS PTY LTD, Lane Cove West (AU)

( * ) Notice: Subject to any disclaimer, the term of this patent is extended or adjusted under 35 U.S.C. 154(b) by 966 days.

(21) Appl. No.: 17/256,082

(22) PCT Filed: Jun. 21, 2019

(86) PCT No.: PCT/AU2019/050646
§ 371 (c)(1),
(2) Date: Dec. 24, 2020

(87) PCT Pub. No.: WO2019/241853
PCT Pub. Date: Dec. 26, 2019

(65) Prior Publication Data
US 2021/0275489 A1    Sep. 9, 2021

(30) Foreign Application Priority Data
Jun. 21, 2018 (AU) .............................. 2018902222

(51) Int. Cl.
| | | |
|---|---|---|
| A61K 31/282 | (2006.01) | |
| A61K 9/127 | (2006.01) | |
| A61K 47/54 | (2017.01) | |
| A61P 35/00 | (2006.01) | |

(52) U.S. Cl.
CPC .......... *A61K 31/282* (2013.01); *A61K 9/1272* (2013.01); *A61K 47/542* (2017.08); *A61K 47/543* (2017.08); *A61P 35/00* (2018.01)

(58) Field of Classification Search
CPC ...... A61K 47/543; A61K 47/542; A61P 35/00
See application file for complete search history.

(56) References Cited

FOREIGN PATENT DOCUMENTS

| | | | |
|---|---|---|---|
| CN | 106046062 A | | 10/2016 |
| CN | 109021026 A | | 12/2018 |
| EP | 0646589 A1 | | 4/1995 |
| WO | 2014106208 A1 | | 7/2014 |
| WO | 2015102928 A1 | | 7/2015 |
| WO | 2015166498 A1 | | 11/2015 |
| WO | WO 2015/166498 | * | 11/2015 |
| WO | 2017115372 A1 | | 7/2017 |
| WO | 2017144551 A1 | | 8/2017 |
| WO | WO2017/144551 | * | 8/2017 |

OTHER PUBLICATIONS

Pinedo et al. (2000) McMahon et al.(2000).*
Nascimento et al., Mol. Phar. (2015) vol. 12(12) pp. 4466-4477
Johnstone et al., InOrg. Chem (2013) vol. 52(17) pp. 9915-9920.*
Novohradsky et al., J'nal of InOrg. Biochem. (2014) vol. 140, pp. 72-79. Varbanhov et al., Dalton Trans (2012) vol. 41(47), pp. 14404-14415.*
Li et al., Bioconjugate Chem., (2016) vol. 27(8), pp. 1802-1806.*
Ana Vanessa Nascimento et al., "Combinatorial-Designed Epidermal Growth Factor Receptor-Targeted Chitosan Nanoparticles for Encapsulation and Delivery of Lipid-Modified Platinum Derivatives in Wild-Type and Resistant Non-Small-Cell Lung Cancer Cells," Molecular Pharmaceutics, Nov. 2015, pp. 4,466-4,477, vol. 12, No. 12.
Timothy C. Johnstone et al., "The Effect of Ligand Lipophilicity on the Nanoparticle Encapsulation of Pt(IV) Prodrugs," Inorganic Chemistry, Jul. 2013, pp. 9,915-9,920, vol. 52, No. 17.
Vojtech Novohradsky et al., "Antitumor platinum(IV) derivatives of oxaliplatin with axial valproate ligands," Journal of inorganic Biochemistry, Jul. 2014, pp. 72-79, vol. 140.
Hristo P. Varbanov et al., "Novel tetracarboxylatoplatinum(IV) complexes as carboplatin prodrugs," Dalton Transactions, Jul. 2012, pp. 14,404-14,415, vol. 41, No. 47.
Wenliang Li et al., "Turning Ineffective Transplatin into a Highly Potent Anticancer Drug via a Prodrug Strategy for Drug Delivery and Inhibiting Cisplatin Drug Resistance," Bioconjugate Chemistry, Jul. 2016, pp. 1,802-1,806, vol. 27, No. 8.
International Search Report & Written Opinion for PCT/AU2019/050646, mailed Aug. 1, 2019.
Office Action in Japanese Patent Application No. 2020-570796, mailed Mar. 15, 2022.
Decision of Refusal for Japanese Patent Application No. 2020-570796, mailed Mar. 7, 2023.
Search Report and Written Opinion in Singapore Patent Application No. 11202107877W, mailed Jul. 24, 2022.
Shuang Liang et al., "Carboplatin-loaded SMNDs to reduce GSH-mediated platinum resistance for prostate cancer therapy," Journal of Materials Chemistry B, Sep. 28, 2018, pp. 7,004-7,014, vol. 6, No. 43. (Abstract only, as that's all we have).
Extended Search Report in European Patent Application No. EP19823050.0, mailed Mar. 3, 2022.
Jenny Z. Zhang et al., "Facile Preparation of Mono-, Di- and Mixed-Carboxylato Platinum(IV) Complexes for Versatile Anticancer Prodrug Design," Chemistry—A European Journal, Jan. 28, 2013, pp. 1,672-1,676, vol. 19, No. 5.
Office Action in Japan Patent Application No. 2020-570796, mailed Oct. 25, 2022.
Office action for related EP Application No. EP19823050.0, mailed Aug. 18, 2023.

* cited by examiner

*Primary Examiner* — Paul V Ward
(74) *Attorney, Agent, or Firm* — Piloff Passino & Cosenza LLP; Rachel K. Piloff; Sean A. Passino

(57) ABSTRACT

The present invention relates to platinum (IV) prodrug lipid-based amphiphiles and compositions thereof. In particular, it relates to cisplatin, oxaliplatin and carboplatin prodrugs with the capacity to make stable liquid crystalline nanoparticles and crystalline nanoparticles, and uses thereof to treat cancer in animals, including humans.

16 Claims, 12 Drawing Sheets

PLATINUM-BASED AMPHIPHILE PRODRUGS

FIELD OF THE INVENTION

The present invention relates to improved prodrugs, and compositions thereof. In particular, it relates to amphiphilic platinum-based prodrugs with the capacity to make stable liquid crystalline or crystalline nanoparticles, and uses thereof to treat animals, including humans.

BACKGROUND OF THE INVENTION

Platinum anticancer agents are one of the most widely-used inorganic anticancer agents that display significant genotoxicity. It is known that platinum drugs interfere with DNA replication via binding with DNA. Three platinum containing drugs are approved worldwide for treatment of cancer in humans, namely, cisplatin, carboplatin and oxaliplatin.

Cis-diamminedichloroplatinum (II) (cisplatin) was serendipitously discovered in the late 1960s and is a very effective chemotherapeutic. The clinical trial database published by U.S. National Institute of Health (NIH), the European clinical trial registerer, maintained by EMA, and the International Clinical Trial Registry Platform of the WHO have listed cisplatin as an agent that has the utmost number of active clinical trials than any other anticancer drug. Upon entry into cells, the low intracellular concentration of chloride ions (4-20 mM) compared to the blood stream (100 mM) results in aquation of one or both of the chloride ligands. The resulting aquated cisplatin forms covalent adducts with the DNA base guanine (G) and to a lesser extent, adenine (A), and distorts the DNA helix, inhibiting replication and transcription, and ultimately leads to apoptosis. Cisplatin has had a major clinical impact, particularly for patients with non-small cell lung cancer, testicular cancer, ovarian cancer, and head and neck cancer. Cisplatin is estimated to be administered to 40-80% of cancer patients undergoing chemotherapy. However, its clinical use is often restricted due to severe adverse effects including nephrotoxicity (kidney damage and reduced kidney function), neurotoxicity (damage to the nervous system), ototoxicity (hearing loss), myelosuppression (decrease in production of various blood cells including leukocytes, erythrocytes, and thrombocytes), and acquired drug resistance.

Efficient delivery of cisplatin into the tumour site requires site specific targeting. Nanoparticles are well known to passively accumulate in tumours and inflammatory tissues due to their unique vascular disorders and characteristics, as well as lack of a lymphatic recovery system—the so called "enhanced permeation and retention effect (EPR)" phenomenon.

Encapsulation of anticancer agents within nanoparticles has been investigated as the second generation chemotherapeutic. Liposomal formulations of cisplatin by physically encapsulating cisplatin (liplacis©) in the interior cavity of liposomes (WO2011032563A1) has been developed to facilitate tumour targeted drug delivery. Synthetic polymeric nanoparticles, encapsulating platinum-based conjugates have been widely investigated (WO2006098496 and Gu et al 2008). However, inefficient encapsulation of physically encapsulated anticancer drugs, rapid leakage and burst release from the nanoparticles before reaching the desired target, and difficulties preparing reproducible formulations of targeted nanoparticles is a drawback of physically encapsulated nano-delivery systems and may cause adverse effects, including lack of efficacy and danger to patients.

There remains a need to generate better methods of delivering platinum-based anticancer agents.

Reference to any prior art in the specification is not, and should not be taken as, an acknowledgment or any form or suggestion that this prior art forms part of the common general knowledge in Australia or any other jurisdiction or that this prior art could reasonably be expected to be ascertained, understood and regarded as relevant by a person skilled in the art.

SUMMARY OF THE INVENTION

The current invention seeks to provide platinum-based prodrugs capable of forming self-assembled structures. The invention also provides pharmaceutical compositions thereof. These higher order phases provide a modified release profile for the platinum-based drug.

In one aspect, this invention provides a prodrug of general formula I:

$$X_1-Y_1-A-(Y_2)_n-X_2 \quad (1)$$

wherein A is an oxidised platinum (IV)-based therapeutically active agent;

$Y_1$ and $Y_2$ are independently selected cleavable bonds between $X_1$ and $X_2$, respectively, and A;

n=0 or 1, wherein when $X_2$ is a substituent according to formula (a), (b), or (c), n is 1;

$X_1$ is selected from the group consisting of a substituent according to formula (a), a substituent according to formula (b), and a substituent according to formula (c):

$$R- \quad (a)$$

$$R-S- \quad (b)$$

$$R-S-L- \quad (c)$$

$X_2$ is selected from the group consisting of H, a substituent according to formula (a), a substituent according to formula (b), and a substituent according to formula (c):

$$R- \quad (a)$$

$$R-S- \quad (b)$$

$$R-S-L- \quad (c)$$

wherein

R is selected from the group consisting of alkyl, alkenyl, alkynyl, branched alkyl, branched alkenyl, branched alkynyl, substituted alkyl, substituted alkenyl, substituted alkynyl groups, and their analogues;

S is selected from the group consisting of (polyethylene glycol)$_m$, wherein m=1-10, an amino acid, and an ethanolamide functionalised amino acid;

L is a linker group that is covalently attached to S—R at one attachment site and to the therapeutically active agent A at a second attachment site via the bond Y to A.

In a preferred embodiment, A is selected from the group consisting of cisplatin, oxaliplatin, carboplatin and derivatives thereof. In one preferred embodiment, A is cisplatin or a derivative thereof. In another preferred embodiment, A is oxaliplatin or a derivative thereof. In yet another preferred embodiment, A is carboplatin or a derivative thereof.

$X_1$ and $X_2$ may be identical or different.

In one embodiment $X_2$ is hydrogen and $X_1$ is selected from the group consisting of a substituent according to formula (a), a substituent according to formula (b), and a substituent according to formula (c). In this embodiment, the platinum (IV)-based therapeutically active agent is attached to one R group, via a cleavable covalent bond, $Y_1$, either directly (formula I(a)), via a spacer group S (formula I(b)) or via a linker group L and a spacer group S (formula I(c)). The R group is a molecule capable of conferring self-assembly properties to the platinum (IV)-based therapeutically active agent. In this embodiment, n=0 or 1 such that $Y_2$ may (n=1) or may not (n=0) be present.

In a preferred embodiment, $X_1$ and $X_2$ are independently selected from the group consisting of a substituent according to formula (a), a substituent according to formula (b), and a substituent according to formula (c). In this embodiment, the platinum (IV)-based therapeutically active agent is attached to two R groups, via independently selected cleavable covalent bonds, $Y_1$ and $Y_2$, either directly (formula I(a)), via a spacer group S (formula I(b)) or via a linker group L and a spacer group S (formula I(c)). $X_1$ and $X_2$ may be identical or different. Preferably, $X_1$ and $X_2$ are identical. In this embodiment, n=1.

R is generally hydrophobic. Optionally, R has a linear chain length equivalent to 10 to 30 carbon atoms. In one embodiment, R is alpha-tocopherol. In another embodiment, R is an isoprenoid group. In other embodiments, R is an hydroxylated alkyl or hydroxylated alkenyl group. Preferred embodiments of R include but are not limited to: alkyl, alkenyl, alkynyl, branched alkyl, branched alkenyl (isoprenoid), branched alkynyl, substituted alkyl, substituted alkenyl, substituted alkynyl groups and their analogues such as alpha-tocopherol, hydroxylated alkyl or alkenyl groups. In preferred embodiments, R has a chain length equivalent to 10 to 30 carbon atoms. Preferably, the chain length is equivalent to 10 to 24 carbon atoms, more preferably equivalent to 12 to 24 carbon atoms, and more preferably equivalent to 14 to 20 carbon atoms. Generally, R is intended to confer self-assembling properties to A.

In preferred embodiments, R is selected from the group consisting of myristyl, myristoyl, palmityl, palmitoyl, stearyl, stearoyl, oleyl, oleoyl, linoleyl, linoleoyl, linolenyl, linolenoyl, arachidonyl, arachidonoyl, phytanyl, phtanoyl, hexahydrofarnesyl, and hexahydrofarnesoyl chains. Most preferably, R is selected from the group consisting of myristyl, myristoyl, oleyl, oleoyl, linoleyl, linoleoyl, phytanyl, phytanoyl, hexahydrofarnesyl, and hexahydrofarnesoyl chains.

Preferably, Y (including $Y_1$ and $Y_2$) is a selectively cleavable bond independently selected from the group consisting of ester and carbonate. Preferably, Y is an ester. $Y_1$ and $Y_2$ may be identical or different, preferably $Y_1$ and $Y_2$ are identical. In a particularly preferred embodiment $Y_1$ and $Y_2$ are both an ester.

S is selected from the group consisting of (polyethylene glycol)$_m$, wherein m=1-10, an amino acid, and an ethanolamide functionalised amino acid. In one preferred embodiment, S is selected from the group consisting of (polyethylene glycol)$_m$, wherein m=1-10, wherein m is selected from the group consisting of 1, 2, 3, 4, 5, 6, 7, 8, 9 and 10. In a particularly preferred embodiment, S is selected from the group consisting of polyethylene glycol (PEG)$_{1-10}$, α-carboxy polyethylene glycol (HOOC-PEG)$_{1-10}$, and α-amino polyethylene glycol (H$_2$N-PEG)$_{1-10}$. Preferably, S is (PEG)$_{1-10}$, more preferably S is (PEG)$_{1-6}$. In a particularly preferred embodiment, S is (PEG)$_{3-6}$. In another preferred embodiment, S is an ethanolamide functionalised amino acid, preferably, lysinoyl ethanolamide.

In one embodiment, L is a selectively cleavable linker group selected from the group consisting of: succinic anhydride, maleic anhydride, glutaric anhydride, diglycolic anhydride, glycolic acid, chloroacetic acid, hydroxy propane sulfonic acid, glycine and alanine.

In one preferred embodiment, the general formula (I) is a compound according to formula (II):

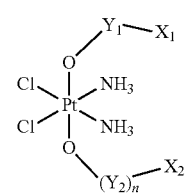

Formula (II)

wherein $Y_1$ and $Y_2$ are independently selected cleavable bonds between $X_1$ and $X_2$, respectively, and a platinum (IV)-based therapeutically active agent;

n=0 or 1, wherein when $X_2$ is a substituent according to formula (a), (b), or (c), n is 1;

$X_1$ is selected from the group consisting of a substituent according to formula (a), a substituent according to formula (b), and a substituent according to formula (c):

R— (a)

R—S— (b)

R—S—L— (c)

$X_2$ is selected from the group consisting of H, a substituent according to formula (a), a substituent according to formula (b), and a substituent according to formula (c):

R— (a)

R—S— (b)

R—S—L— (c)

wherein

R is selected from the group consisting of alkyl, alkenyl, alkynyl, branched alkyl, branched alkenyl, branched alkynyl, substituted alkyl, substituted alkenyl, substituted alkynyl groups, and their analogues;

S is selected from the group consisting of (polyethylene glycol)$_m$, wherein m=1-10, an amino acid, and an ethanolamide functionalised amino acid;

L is a linker group that is covalently attached to S—R at one attachment site and to the platinum (IV)-based therapeutically active agent at a second attachment site via the bond Y to the platinum (IV)-based therapeutically active agent.

In a particularly preferred embodiment, the general formula (II) is a compound selected from the group consisting of:

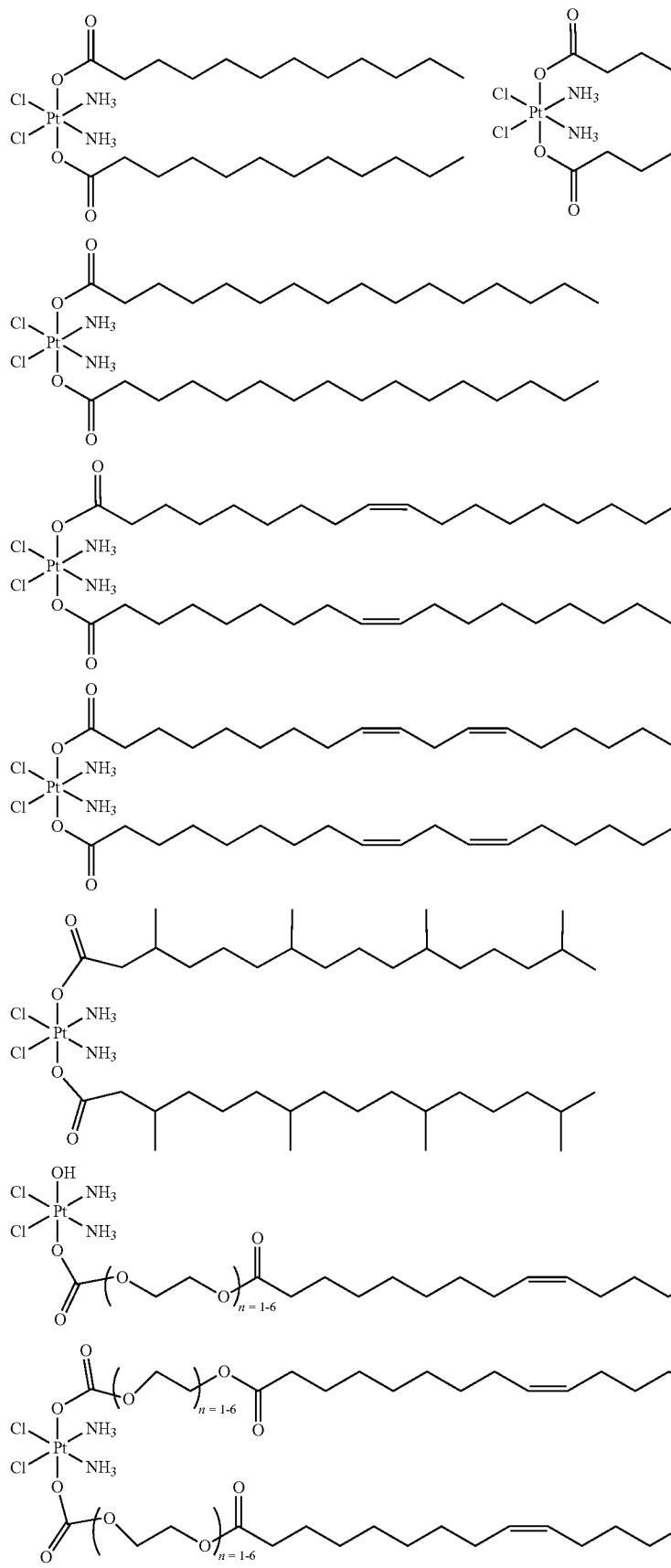

-continued
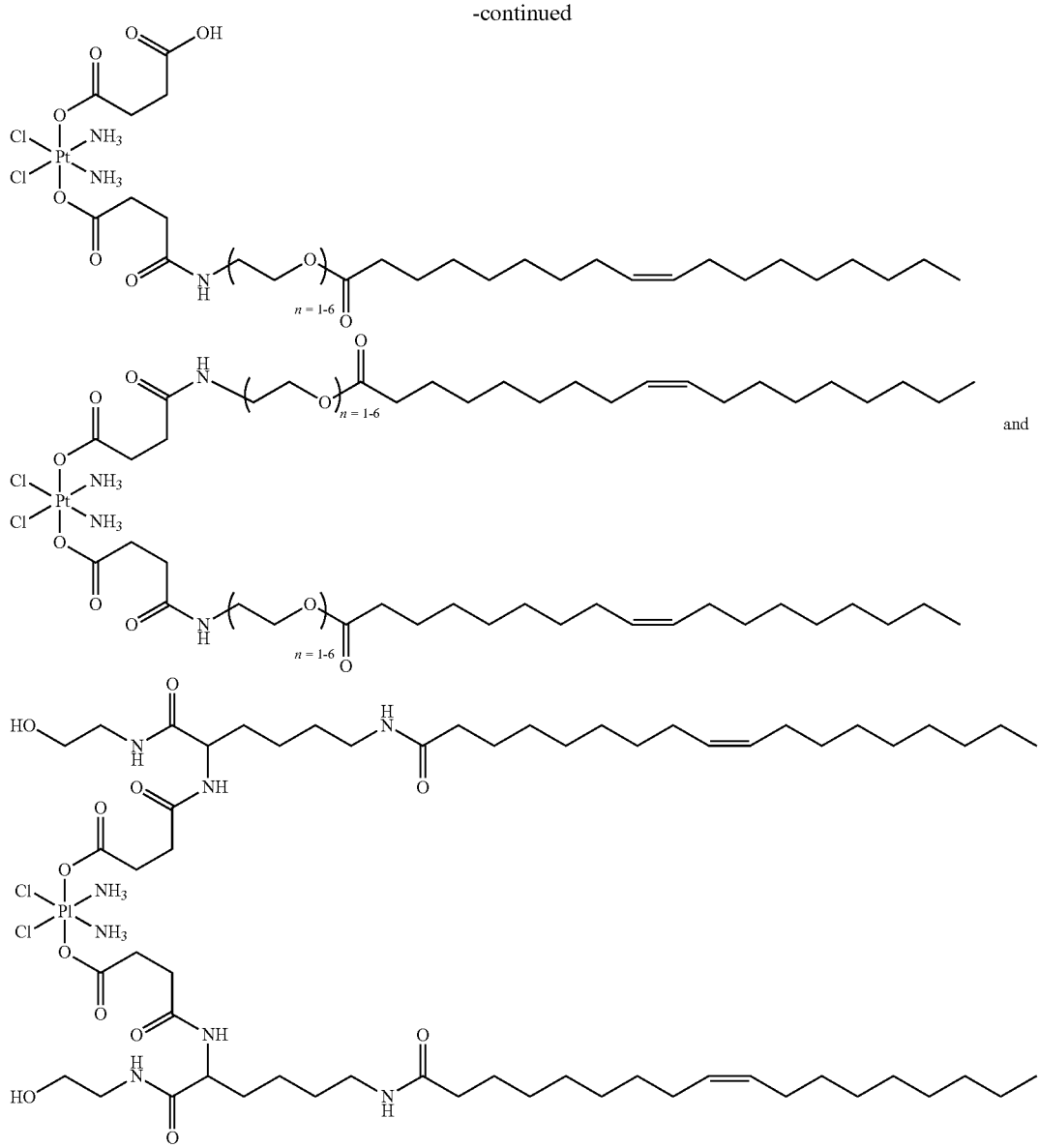
and
In another preferred embodiment, the general formula (I) is a compound according to formula (III):
Formula III
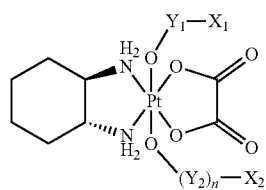
wherein $Y_1$, $Y_2$, $X_1$ and $X_2$ are as defined as in Formula II.
In a particularly preferred embodiment, the general formula (III) is a compound selected from the group consisting of:

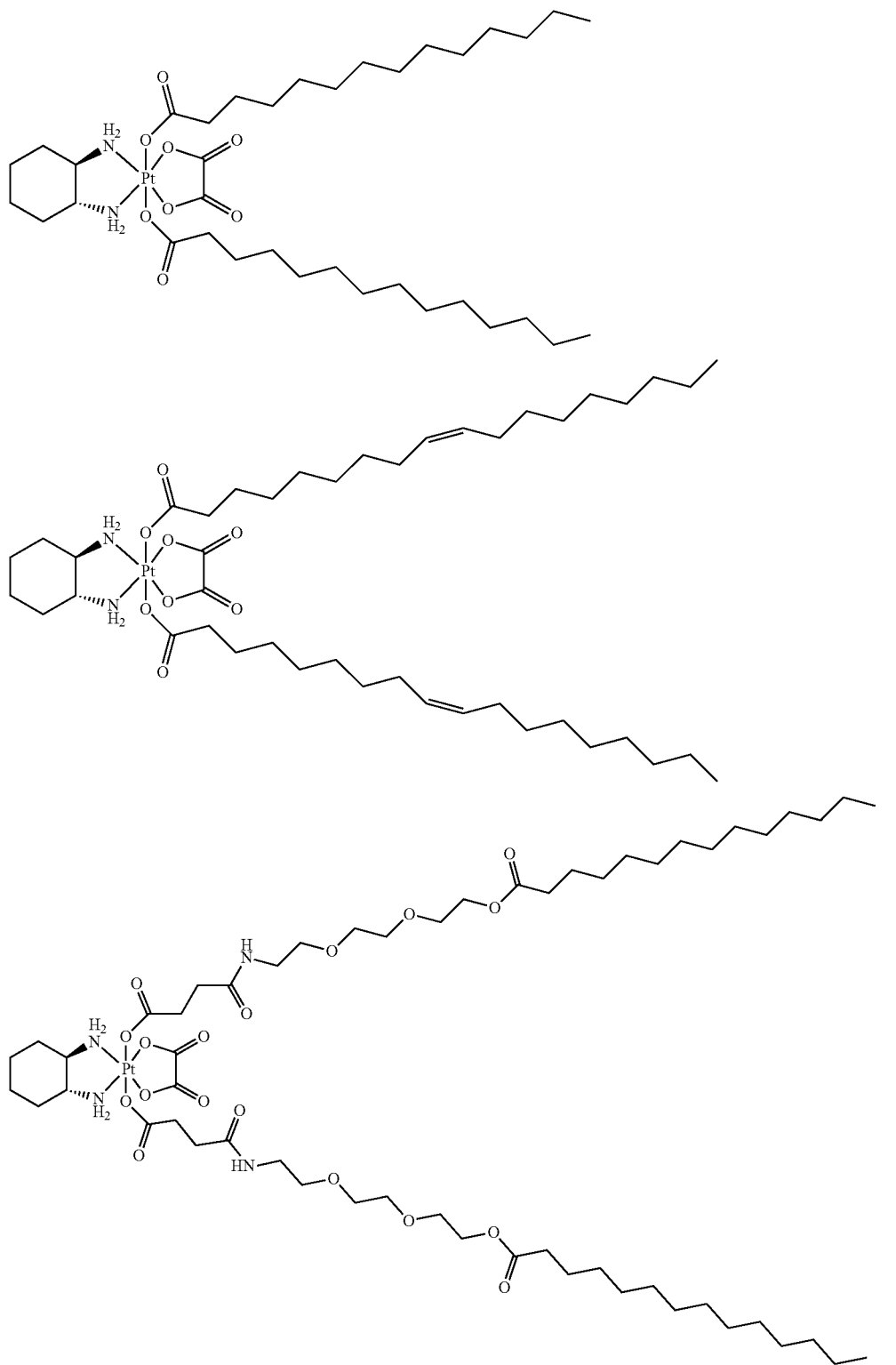

-continued
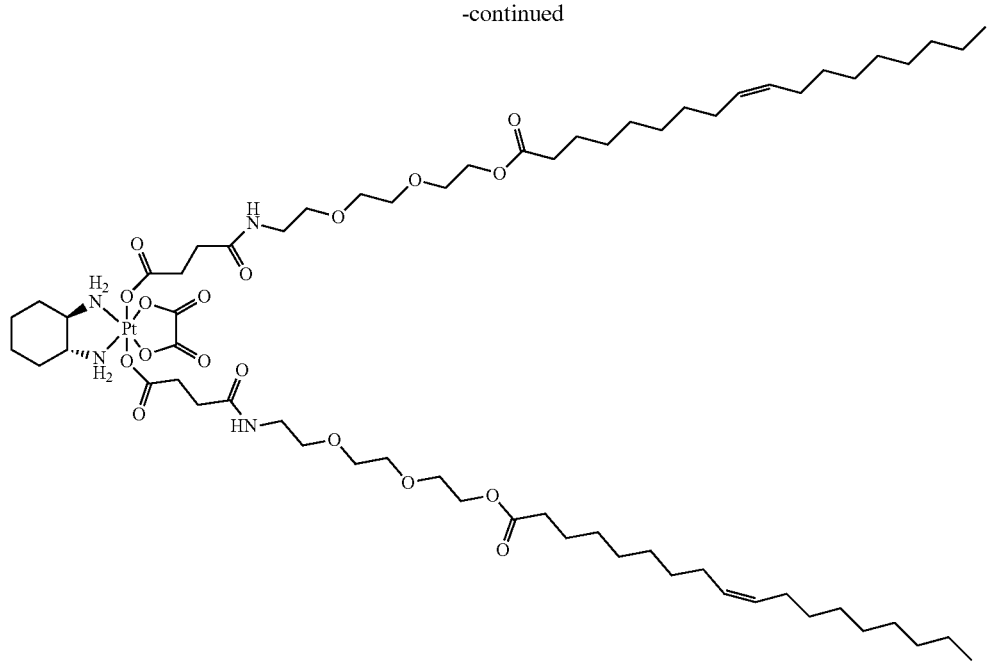
In yet another preferred embodiment, the general formula (I) is a compound according to formula (IV):
Formula IV
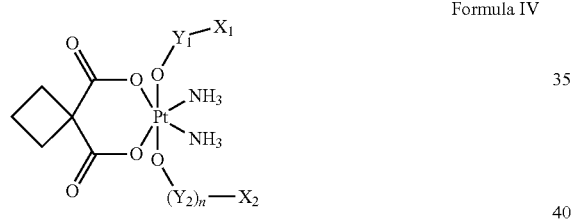
wherein $Y_1$, $Y_2$, $X_1$ and $X_2$ are as defined as in Formula II.
In a particularly preferred embodiment, the general formula (IV) is a compound selected from the group consisting of:
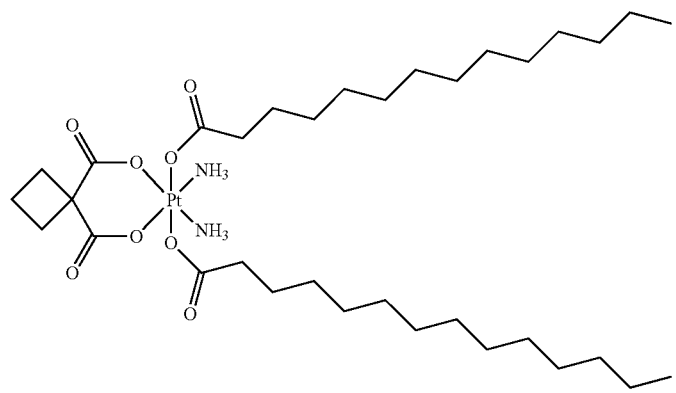

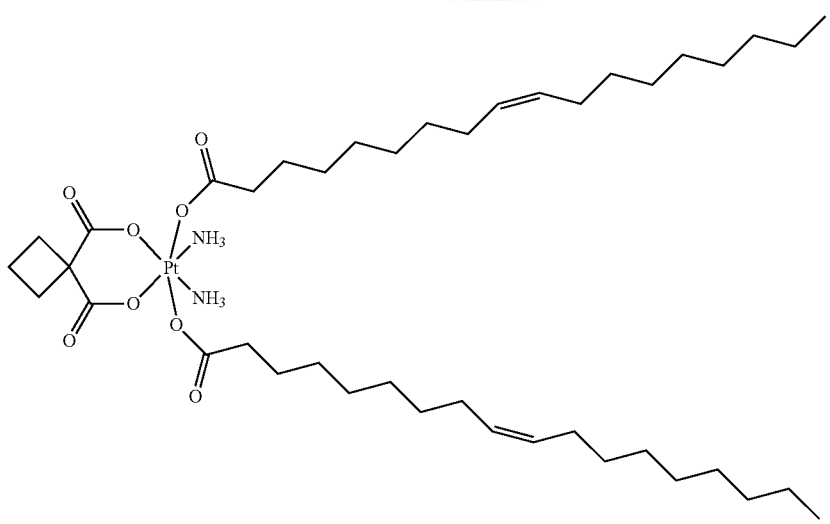
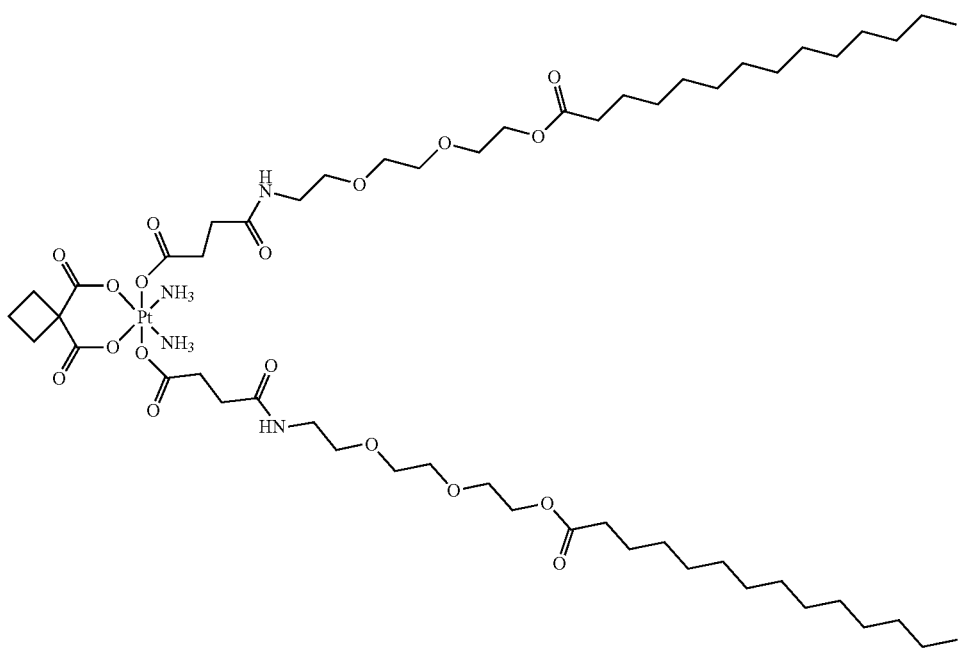
and

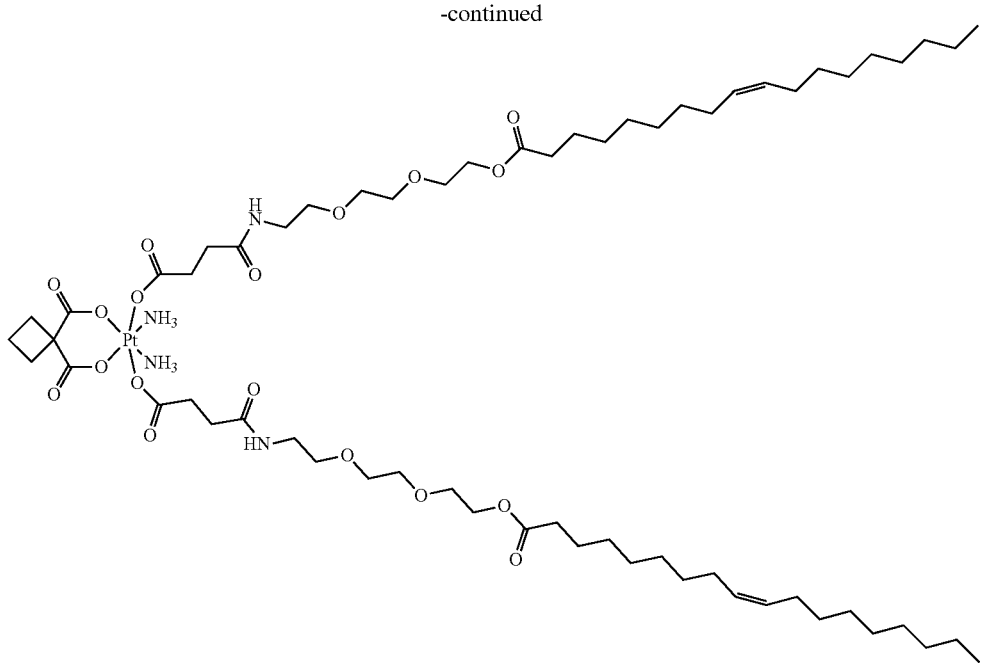

Preferably, a prodrug of general formula (I), (II), (III), or (IV), is capable of forming a self-assembled structure having a lyotropic phase that displays lamellar, cubic, hexagonal, sponge, micellar, or crystalline lamellar morphologies. More preferably, the phase is a lamellar, cubic, hexagonal, micellar or sponge phase. More preferably still, the phase is an inverse phase.

In a second aspect of the invention there is provided self-assembled structures of the prodrugs of the general formula (I), (II) (III), or (IV), of the above aspect. In one embodiment, the self-assembled structures of the prodrugs of the general formula (I), (II), (III), or (IV), further comprise a component selected from the group consisting of: phospholipids, cholesterol, glycerol lipids, other prodrug amphiphiles, hydrophobic drugs and combinations thereof.

Preferably, the self-assembled structure is a lyotropic phase that displays lamellar, cubic, hexagonal, sponge, emulsion, or crystalline lamellar morphologies. More preferably, the phase is a lamellar, cubic, hexagonal, micellar ($L_2$) or sponge ($L_3$) phase. More preferably still, the phase is an inverse phase. Generally inverse phases are advantageous as drug delivery vehicles because of their thermodynamic stability in excess water, greater surface area and controlled channel dimensions, the latter property being particularly important for release of active agent embedded within a self-assembled matrix. Accordingly, there is provided prodrugs that are capable of self-assembly into lamellar, inverse cubic, inverse sponge ($L_3$), inverse hexagonal, or inverse micellar ($L_2$) phases, preferably lamellar, inverse cubic, $L_2$ or $L_3$ phases. In another embodiment, the self-assembled prodrug has a crystalline structure.

The self-assembled structure of the prodrugs according to the current invention may be a bulk phase, or may be colloidal particles or nanoparticles derived therefrom. Particularly preferred colloidal particles or nanoparticles may be selected from the following group: liposomes, cubosomes, hexosomes, "sponge-like" particles (spongosomes) or inverse micelles. Depending on conditions, more than one phase or colloidal particles may be present in a self-assembled structure.

In a particularly preferred embodiment, the self-assembled structures are selected from compounds of cisplatin prodrugs of formula (II), compounds of oxaliplatin prodrugs of formula (III), or compounds of carboplatin prodrugs of formula (IV). Preferably, the self-assembled structures are lamellar, cubic, $L_2$ or $L_3$ phases, solid lipid nanoparticles, or combinations thereof. Such self-assembled structures may be suitably stabilised for pharmaceutical use by a surfactant stabiliser, such as polyethyleneglyocol-lipid, polysorbate, poloxamer, and combinations thereof.

In another aspect of the invention, there is provided a method of modulating the release of a platinum (IV)-based therapeutically active agent, such as a drug or prodrug, comprising covalently linking the platinum (IV)-based therapeutically active agent A to at least one tail component R via a cleavable covalent bond Y, preferably including a spacer S and optionally including a linker L, to form an amphiphile of the general formula (I), (II) (III), or (IV), capable of self-assembling into a self-assembled structure, and wherein the amphiphile is cleavable in vivo to release the therapeutically active agent. The amphiphile may be capable of self-assembling into a self-assembled structure ex vivo and/or in vivo.

In another aspect of the present invention there is provided a method of modulating the release of a platinum (IV)-based therapeutically active agent, such as a drug or prodrug, comprising covalently linking the platinum (IV)-based therapeutically active agent A to at least one tail component R via a cleavable covalent bond Y, preferably including a spacer S and optionally including a linker L, to form an amphiphile of the general formula (I), (II) (III), or (IV), capable of self-assembling into a self-assembled structure under physiological conditions, and wherein the amphiphile is cleavable in vivo to release the therapeutically active agent.

In one embodiment of this aspect there is provided a method of modulating the bioavailability of a platinum (IV)-based therapeutically active agent, the method including covalently linking the platinum (IV)-based therapeutically active agent A to at least one tail component R via a cleavable covalent bond Y, preferably including a spacer S and optionally including a linker L, to form an amphiphile of the general formula (I), (II) (III), or (IV), wherein the covalent bond is cleavable in vivo to release the therapeutically active agent from the self-assembled structure; administering self-assembled structures of the amphiphile to a patient.

In one embodiment of this aspect there is provided a method of modulating the bioavailability of a platinum (IV)-based therapeutically active agent, the method including covalently linking the platinum (IV)-based therapeutically active agent A to at least one tail component R via a cleavable covalent bond Y, preferably including a spacer S and optionally including a linker L, to form an amphiphile of the general formula (I), (II) (III), or (IV), wherein the covalent bond is cleavable in vivo to release the therapeutically active agent from the self-assembled structure; administering the amphiphile to a patient such that the amphiphile self-assembles into a self-assembled structure.

In another aspect of the present invention there is provided a method of modulating the bioavailability and release of a platinum (IV)-based therapeutically active agent, such as a drug or prodrug, comprising covalently linking the platinum (IV)-based therapeutically active agent A to at least one tail component R via a cleavable covalent bond Y, preferably including a spacer S and optionally including a linker L, to form an amphiphile of the general formula (I), (II) (III), or (IV), capable of self-assembling into a self-assembled structure, and wherein the amphiphile is cleavable in vivo to release the therapeutically active agent. The amphiphile may be capable of self-assembling into a self-assembled structure ex vivo and/or in vivo.

In another aspect of the present invention there is provided a method of modulating the bioavailability and release of a platinum (IV)-based therapeutically active agent, such as a drug or prodrug, comprising covalently linking the platinum (IV)-based therapeutically active agent A to at least one tail component R via a cleavable covalent bond Y, preferably including a spacer S and optionally including a linker L, to form an amphiphile of the general formula (I), (II) (III), or (IV), capable of self-assembling into a self-assembled structure under physiological conditions, and wherein the amphiphile is cleavable in vivo to release the therapeutically active agent.

In another aspect, there is provided a method of modulating the release of a platinum-based therapeutically active agent or an agent capable of being metabolised in vivo to a platinum-based therapeutically active agent, the method comprising covalently linking an oxidised platinum (IV)-based therapeutically active agent, A, to at least one tail component, X, to form an amphiphile capable of self-assembling into a self-assembled structure, and wherein the amphiphile is cleavable in vivo to release the therapeutically active agent, wherein the amphiphile is of general formula (I), (II), (III) or (IV). The amphiphile may be capable of self-assembling into a self-assembled structure ex vivo and/or in vivo.

In another aspect, there is provided a method of modulating the release of a platinum-based therapeutically active agent or an agent capable of being metabolised in vivo to a platinum-based therapeutically active agent, the method comprising covalently linking an oxidised platinum (IV)-based therapeutically active agent, A, to at least one tail component, X, to form an amphiphile capable of self-assembling under physiological conditions, and wherein the amphiphile is cleavable in vivo to release the therapeutically active agent, wherein the amphiphile is of general formula (I), (II), (III) or (IV).

In one embodiment of this aspect there is provided a method of modulating the bioavailability of a platinum (IV)-based therapeutically active agent, the method including covalently linking an oxidised platinum (IV)-based therapeutically active agent, A, to at least one tail component, X, to form an amphiphile, wherein the amphiphile is of general formula (I), (II), (III) or (IV), wherein the covalent bond is cleavable in vivo to release the therapeutically active agent from the self-assembled structure; administering self-assembled structures of the amphiphile to a patient.

In one embodiment of this aspect there is provided a method of modulating the bioavailability of a platinum (IV)-based therapeutically active agent, the method including covalently linking an oxidised platinum (IV)-based therapeutically active agent, A, to at least one tail component, X, to form an amphiphile, wherein the amphiphile is of general formula (I), (II), (III) or (IV), wherein the covalent bond is cleavable in vivo to release the therapeutically active agent from the self-assembled structure; administering the amphiphile to a patient such that the amphiphile self-assembles into a self-assembled structure.

In another aspect, there is provided a method of modulating the bioavailability and release of a platinum-based therapeutically active agent or an agent capable of being metabolised in vivo to a platinum-based therapeutically active agent, the method comprising covalently linking an oxidised platinum (IV)-based therapeutically active agent, A, to at least one tail component, X, to form an amphiphile capable of self-assembling into a self-assembled structure, and wherein the amphiphile is cleavable in vivo to release the therapeutically active agent, wherein the amphiphile is of general formula (I), (II), (III) or (IV). The amphiphile may be capable of self-assembling into a self-assembled structure ex vivo and/or in vivo.

In another aspect, there is provided a method of modulating the bioavailability and release of a platinum-based therapeutically active agent or an agent capable of being metabolised in vivo to a platinum-based therapeutically active agent, the method comprising covalently linking an oxidised platinum (IV)-based therapeutically active agent, A, to at least one tail component, X, to form an amphiphile capable of self-assembling into a self-assembled structure under physiological conditions, and wherein the amphiphile is cleavable in vivo to release the therapeutically active agent, wherein the amphiphile is of general formula (I), (II), (III) or (IV).

In another aspect, there is provided a method of modulating the bioavailability and release of a platinum-based therapeutically active agent or an agent capable of being metabolised in vivo to a platinum-based therapeutically active agent, the method comprising covalently linking an oxidised platinum (IV)-based therapeutically active agent, A, to at least one tail component, X, to form an amphiphile capable of self-assembling into a self-assembled structure, and wherein the amphiphile is cleavable in vivo to release the therapeutically active agent, wherein the amphiphile is of general formula (I), (II), (III) or (IV). The amphiphile may be capable of self-assembling into a self-assembled structure ex vivo and/or in vivo.

In another aspect of the present invention there is provided a pharmaceutical composition for the treatment of a disease state comprising as an active ingredient self-assembled structures of formula (I), (II), (III) or (IV). In some embodiments, the pharmaceutical composition for the treatment of the disease state consists essentially of an active ingredient that is a self-assembled structure of formula (I), (II), (III) or (IV), optionally in combination with an additional component selected from the group consisting of phospholipids, cholesterol, glycerol lipids, other prodrug amphiphiles, hydrophobic drugs, and combinations thereof, in self-assembled structures. In some embodiments, the self-assembled structures display a lamellar, cubic, hexagonal, micellar cubic, micellar or sponge phase. Preferably, the active ingredient is a self-assembled structure of formula (I), (II), (III) or (IV), wherein the self-assembled structure is selected from the group consisting of liposomes, cubosomes, hexosomes, inverse micellar, less ordered sponge-like nanoparticles, solid lipid nanoparticles, or a combination thereof.

In some embodiments, the disease state is that of the presence of a tumor, and the pharmaceutical composition comprises as an active ingredient solid lipid particles or self-assembled structures of Formula (I), (II), (III) or (IV).

The self-assembled structure/active ingredient is preferably present in the pharmaceutical composition in a therapeutically active amount.

In another aspect of the present invention there is provided a method for treatment of a disease state comprising administering to a patient in need thereof a therapeutically effective amount of a pharmaceutical composition for the treatment of a disease state comprising as an active ingredient self-assembled structures of formula (I), (II), (III), or (IV), optionally in combination with an additional component selected from the group consisting of phospholipids, cholesterol, glycerol lipids, prodrug amphiphiles, hydrophobic drugs and combinations thereof, in self-assembled structures. In some embodiments the self-assembled structures display lamellar, cubic, hexagonal, micellar cubic, micellar or sponge-like phase. Preferably, the active ingredient is self-assembled structures of formula (I), (II), (III) or (IV), wherein the self-assembled structure is selected from the group consisting of: liposomes, cubosomes, hexosomes, inverse micellar, less ordered sponge-like nanoparticles, solid lipid nanoparticles, or a combination thereof.

In some embodiments, the disease state is due to the presence of a tumour and in this case it is preferable that the pharmaceutical composition comprises an active ingredient of a self-assembled structure of formula (I), (II), (III) or (IV), optionally in combination with an additional component selected from the group consisting of phospholipids, cholesterol, glycerol lipids, other prodrug amphiphiles, hydrophobic drugs, and combinations thereof, in self-assembled structures in the form of liposomes, cubosomes, hexosomes, inverse micellar, less ordered sponge nanoparticles, solid lipid nanoparticles, or a combination thereof.

In another aspect of the present invention there is provided a prodrug according to the current invention of formula (I), (II), (III), or (IV), optionally in combination with an additional component selected from the group consisting of phospholipids, cholesterol, glycerol lipids, other prodrug amphiphiles, hydrophobic drugs, and combinations thereof, in a self-assembled structure for the manufacture of a medicament for the treatment of a disease state. The medicament comprises self-assembled bulk or colloidal particle structures as described in previous aspects of the current invention.

In one embodiment of this aspect there is provided a method of delivering a platinum (IV)-based therapeutically active agent utilising the enhanced permeation and retention effect by forming self-assembled structures comprising the active, the method comprising covalently linking the platinum (IV)-based therapeutically active agent A to at least one tail component R, preferably two tail components, via a cleavable covalent bond Y, preferably including a spacer S and optionally including a linker L, to form an amphiphile of formula (I), (II), (III), or (IV), capable of self-assembling into a self-assembled structure, and wherein the amphiphile is cleavable in vivo to release the therapeutically active agent. The amphiphile may be capable of self-assembling into a self-assembled structure ex vivo and/or in vivo. Preferably, the therapeutically active agent is cisplatin, oxaliplatin, carboplatin, or a derivative thereof.

In one embodiment of this aspect there is provided a method of delivering a platinum (IV)-based therapeutically active agent utilising the enhanced permeation and retention effect by forming self-assembled structures comprising the active, the method comprising covalently linking the platinum (IV)-based therapeutically active agent A to at least one tail component R, preferably two tail components, via a cleavable covalent bond Y, preferably including a spacer S and optionally including a linker L, to form an amphiphile of formula (I), (II), (III), or (IV), capable of self-assembling into a self-assembled structure under physiological conditions, and wherein the amphiphile is cleavable in vivo to release the therapeutically active agent. Preferably, the therapeutically active agent is cisplatin, oxaliplatin, carboplatin, or a derivative thereof.

In one embodiment of this aspect, there is provided a method of delivering a platinum (IV)-based therapeutically active agent, the method including covalently linking the platinum (IV)-based therapeutically active agent A to at least one tail component R, preferably two tail components, via a cleavable covalent bond Y, preferably including a spacer S and optionally including a linker L, to form an amphiphile of formula (I), (II), (III), or (IV), wherein the covalent bond is cleavable in vivo to release the therapeutically active agent from the self-assembled structure; administering self-assembled structures of the amphiphile to a patient.

In one embodiment of this aspect, there is provided a method of delivering a platinum (IV)-based therapeutically active agent, the method including covalently linking the platinum (IV)-based therapeutically active agent A to at least one tail component R, preferably two tail components, via a cleavable covalent bond Y, preferably including a spacer S and optionally including a linker L, to form an amphiphile of formula (I), (II), (III), or (IV), wherein the covalent bond is cleavable in vivo to release the therapeutically active agent from the self-assembled structure; administering the amphiphile to a patient such that the amphiphile self-assembles into a self-assembled structure.

Preferably, the amphiphile self-assembles to form a self-assembled structure of a lyotropic mesophase that display lamellar, cubic, hexagonal, sponge and/or micellar morphologies and their analogous nanoparticles, solid lipid nanoparticles or a combination thereof.

In one embodiment, there is provided a pharmaceutical composition comprising as an active ingredient self-assembled structures of formula (I), (II), (III) or (IV) for use in a method of treating a disease state. In some embodiments, the pharmaceutical composition consists essentially of an active ingredient that is a self-assembled structure of formula (I), (II), (III) or (IV), optionally in combination with an additional component selected from the group consisting of phospholipids, cholesterol, glycerol lipids, other prodrug amphiphiles, hydrophobic drugs and combinations thereof, in self-assembled structures. In some embodiments, the self-assembled structures display a lamellar, cubic, hexagonal, micellar cubic, micellar or sponge phase. Preferably, the active ingredient is a self-assembled structure of formula (II), (III), or (IV) in liposomes, inverse cubosomes, inverse hexosomes, inverse micelles or less ordered sponge-like nanoparticles or solid lipid nanoparticles, or a combination thereof.

In some embodiments of this aspect of the invention, the disease state is that of the presence of a tumor, and the pharmaceutical composition comprises as an active ingredient solid lipid particles or self-assembled structures of Formula (II), (III), or (IV).

A further aspect of the present invention relates to a process for preparing the bulk phases of lamellar, cubic, hexagonal, sponge phases and crystalline mesophases according to the current invention prepared by the process of this aspect.

A further aspect of the present invention relates to a process for preparing colloidal particles or nanoparticles from the bulk phase according to the current invention. There is further provided colloidal particles according to the current invention prepared by the process of this aspect.

Any embodiment herein shall be taken to apply mutatis mutandis to any other embodiment unless specifically stated otherwise.

The present disclosure is not to be limited in scope by the specific embodiments described herein, which are intended for the purpose of exemplification only. Functionally-equivalent products, compositions and methods are clearly within the scope of the invention, as described herein.

Further aspects of the present invention and further embodiments of the aspects described in the preceding paragraphs will become apparent from the following description, given by way of example and with reference to the accompanying drawings.

It will be understood that the term "comprises" (or its grammatical variants) as used in this specification is equivalent to the term "includes" and should not be taken as excluding the presence of other elements or features.

DETAILED DESCRIPTION OF THE EMBODIMENTS

Figure 1:
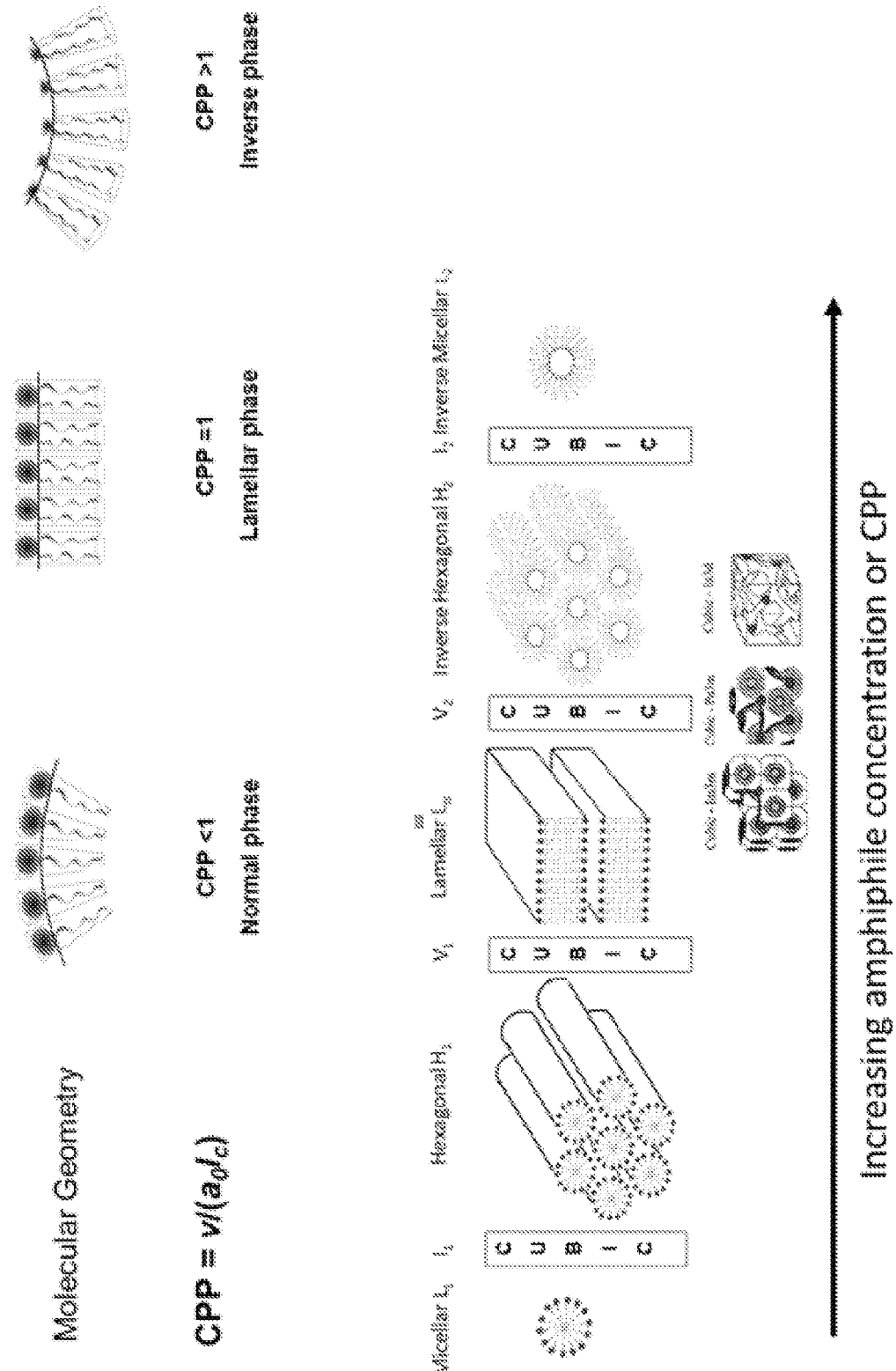
FIG. 1: Schematic picture of the different phases that can occur upon hydration of different amphiphiles. Abbreviations for different mesophases are micellar ($L_1$); micellar cubic ($I_1$), normal hexagonal ($H_1$), bicontinuous cubic ($V_1$), Lamellar ($L_\alpha$), inverse bicontinuous cubic ($V_2$), inverse hexagonal ($H_2$), inverse micellar cubic ($I_2$), and inverse micellar ($L_2$), where subscripts 1 and 2 refer to "normal" and "inverse" phases, respectively.

It will be noted that various terms employed in the specification, examples and claims have meanings that will be understood by one of ordinary skill in the art. However, for clarity of meaning intended in this document, certain terms are defined below.

The term "prodrug" as used throughout the specification refers to a therapeutically active compound including structural modifications thereto, such that in vivo the prodrug is converted, for example, by hydrolytic, reductive, oxidative, or enzymatic cleavage to the therapeutically active compound by one or more reactions or steps. It includes an active that requires general steps of metabolism to produce the active therapeutic molecule—that is, this term is also understood to encompass "pre-prodrugs".

The term cisplatin prodrug as used throughout the specification refers to a compound of general formula (II) that is capable of being converted to cisplatin in vivo, for instance, by means of reductive chemical reaction or enzymatic reaction.

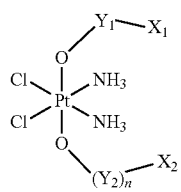

Formula (II)

The term oxaliplatin prodrug as used throughout the specification refers to a compound of general formula (III) that is capable of being converted to oxaliplatin in vivo, for instance, by means of reductive chemical reaction or enzymatic reaction.

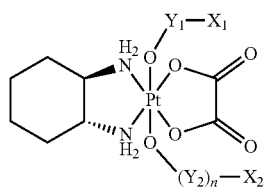

Formula (III)

The term carboplatin prodrug as used throughout the specification refers to a compound of general formula (IV) that is capable of being converted to carboplatn in vivo, for instance, by means of reductive chemical reaction or enzymatic reaction.

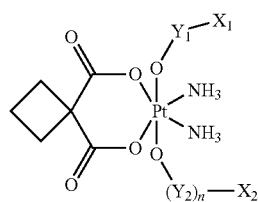

Formula (IV)

wherein
$Y_1$ and $Y_2$ are independently selected cleavable bonds between $X_1$ and $X_2$, respectively, and a platinum (IV)-based therapeutically active agent;
n=0 or 1, wherein when $X_2$ is a substituent according to formula (a), (b), or (c), n is 1;
$X_1$ is selected from the group consisting of a substituent according to formula (a), a substituent according to formula (b), and a substituent according to formula (c):

R—            (a)

R—S—           (b)

R—S—L—         (c)

$X_2$ is selected from the group consisting of H, a substituent according to formula (a), a substituent according to formula (b), and a substituent according to formula (c):

R—            (a)

R—S—           (b)

R—S—L—         (c)

wherein
R is selected from the group consisting of alkyl, alkenyl, alkynyl, branched alkyl, branched alkenyl, branched alkynyl, substituted alkyl, substituted alkenyl, substituted alkynyl groups, and their analogues;
S is selected from the group consisting of (polyethylene glycol)$_m$, wherein m=1-10, an amino acid, and an ethanolamide functionalised amino acid;
L is a linker group that is covalently attached to S—R at one attachment site and to the platinum (IV)-based therapeutically active agent at a second attachment site via the bond Y to the platinum (IV)-based therapeutically active agent.

The term "self-assembled structure" as used throughout the specification is meant to refer to an aggregate of amphiphiles that possess some degree of internal organisational order. The self-assembled structures may be formed by contacting the amphiphile with solvent. The self-assembled structure may refer to either a bulk lyotropic phase, a colloidal particle derived therefrom (a so-called "colloidosome" or "nanoparticle"), or a solid lipid particle.

The term "bulk phase" as used throughout the specification is understood to mean a lyotropic phase that includes but is not limited to: micellar cubic ($I_1$); normal hexagonal ($H_1$); bicontinuous cubic ($V_1$); lamellar ($L_\alpha$); inverse bicontinuous cubic ($V_2$); inverse hexagonal ($H_2$); inverse micellar ($L_2$) and sponge ($L_3$) phases.

The term "colloidal particles" or "nanoparticles" as used throughout the specification is to be understood to refer to "colloidosomes" and solid lipid particles. The term "colloidosome" as used throughout the specification is to be understood to refer to a colloidal particle that possesses the same internal nanostructure of a bulk lyotropic phase. The term solid lipid particle as used throughout the specification is understood to mean a colloidal particle of the prodrug of the current invention, wherein the colloidal particle comprises a core of the neat prodrug and usually will be stabilised by a surface layer of surfactant. The neat prodrug core may be in a crystalline, microcrystalline, liquid crystalline or a non-crystalline form. It will be understood that the term "particle" refers to particles that may be nanoparticles or microparticles based on their average size. Often such particles are referred to as "solid lipid nanoparticles" although they may in fact be in a size range of microparticles. This form of self-assembled structure does not swell upon contact with excess solvent.

The term "lamellar phase" as used throughout the specification is to be understood to mean a stacked bilayer arrangement, where opposing monolayers of the hydrophilic portion of amphiphile molecules are separated by a polar solvent domain, while the hydrophobic portion of the amphiphile molecule of the back-to-back layers are in intimate contact to form a hydrophobic layer. The planar lamellar phase is referred to as the "$L_\alpha$ phase".

The term "cubic phase" as used throughout the specification refers to two main classes of phases: micellar cubic and bicontinuous cubic. "Micellar cubic phase" refers to a phase consisting of spherical micelles arranged in a cubic array. A "normal micellar cubic phase" or "$L_I$ phase" consists of spherical normal micelles. The term "inverse micellar cubic phase" consists of spherical inverse micelles arranged in a cubic array.

"Bicontinuous cubic phase" refers to a family of closely related phases that consist of a single curved lipid bilayer that forms a complex network that separates the polar solvent space into two continuous, but non-intersecting volumes. Bicontinuous cubic phases possess long range order based upon a cubic unit cell. Bicontinuous cubic phases have zero mean curvature; that is, at all points on surface of the amphiphile bilayer, the surface is as convex as it is concave. Bicontinuous cubic phases may be of the normal ("$v_I$ phase") or inverse ("$v_{II}$ phase") type. Several types of long range orientational orders have been observed for bicontinuous cubic phases; the orientational order in these phases correspond to space groups Ia3d, Pn3m, and Im3m. When a colloidosome possesses the internal structure of a bulk cubic phase the colloidosome may be referred to as a "cubosome".

The term "hexagonal phase" as used throughout the specification is to be understood to mean an amphiphile phase consisting of long, rod-like micelles packed into a hexagonal array. A "normal hexagonal phase" is a hexagonal phase consisting of long, rod-like normal micelles, whilst an "inverse hexagonal phase" is a hexagonal phase consisting of long, rod-like inverse micelles. The normal hexagonal phase may be referred to as the "$H_I$ phase" and the inverse hexagonal phase may be referred to as the "$H_{II}$ phase". When a colloidosome possesses the internal structure of a bulk hexagonal phase the colloidosome may be referred to as a "hexosome".

The term "sponge phase" or "$L_3$ phase" as used throughout the specification refers to a phase that resembles a bicontinuous cubic phase, in that it possesses an amphiphile bilayer that separates the polar solvent space into two unconnected volumes, but it does not possess long range order. Accordingly, these phases are analogous to a "melted cubic phase".

The term "lattice parameter" as used throughout the specification means a set of lattice constants that define a unit cell of a crystalline solid or liquid crystal, and may include values such as the length of the unit cell.

The term "isoprenoid" as used throughout the specification is to mean an alkyl chain consisting of isoprene (2-methyl-1,3-butadiene) monomers or subunits. The use of the term "isoprenoid" as used herein is intended to encompass unsaturated, partially saturated or fully saturated isoprene analogues and derivatives.

The term "pharmaceutical composition" as used throughout the specification means a composition comprising a therapeutically effective amount of at least one prodrug according to the current invention and at least one pharmaceutically acceptable carrier, excipient, diluent, additive or vehicle selected based upon the intended form of administration, and consistent with conventional pharmaceutical practices.

The terms "therapeutically active agent", "pharmaceutically active agent", "active agent" and "active ingredient" as used throughout the specification refer to substances that are intended for, without limitation, the diagnosis, cure, mitigation, treatment, prevention and/or modification of a state in a biological system. The terms "drug" and "therapeutically active agent" are used interchangeably throughout this specification.

In the context of the invention, the "therapeutically active agent" is a platinum-based therapeutically active agent. In a preferred embodiment, the therapeutically active agent is selected from the group consisting of cisplatin, oxaliplatin, carboplatin and derivatives thereof. In one preferred embodiment, the therapeutically active agent is cisplatin or a derivative thereof. In another preferred embodiment, A is oxaliplatin or a derivative thereof. In yet another preferred embodiment, A is carboplatin or a derivative thereof. The purpose of the invention is to deliver a platinum-based drug in the form of a platinum (IV) prodrug. A skilled person in this field understands that the active form of such a drug is a form capable of, without limitation, the diagnosis, cure, mitigation, treatment, prevention and/or modification of a state in a biological system. The active form of the platinum-based drugs cisplatin, oxaliplatin and carboplatin is currently understood to be native platinum (II)-based forms, specifically cisplatin (II), oxaliplatin (II) and carboplatin (II) and derivatives thereof. The purpose of the invention is to deliver a platinum-based drug in a form that is capable of being metabolised in vivo to an active platinum (II)-based drug either directly or indirectly, for example via an oxidised platinum (IV)-based drug comprising two axial hydroxyl groups. Accordingly, as administered Pt (IV) converts to Pt (II) in vivo, "therapeutically active agent" in this specification includes both the Pt (IV) and Pt (II) forms.

In one embodiment, the therapeutically active agent is a platinum-based agent functionalised with at least one axial hydroxyl group. In one embodiment, the oxidised platinum (IV) based agent is functionalised with one axial hydroxyl group and one axial carboxyl group. In a preferred embodiment, the oxidised platinum (IV) based agent is functionalised with two axial hydroxyl groups. In one preferred embodiment, the oxidised platinum (IV) based agent is cisplatin (IV) functionalised with two axial hydroxyl groups. In another preferred embodiment, the platinum-based agent is oxaliplatin (IV) functionalised with two axial hydroxyl groups. In yet another preferred embodiment, the oxidised platinum (IV) based agent is carboplatin (IV) functionalised with two axial hydroxyl groups.

In one embodiment, the therapeutically active agent is a prodrug, in which case $X_1$—$Y_1$-A-$(Y_2)_n$—$X_2$ represents a pre-prodrug. In this embodiment, the axial hydroxyl groups are further functionalised with $X_1$—$Y_1$ and $(Y_2)_n$—$X_2$. In one embodiment, wherein n=0 and $X_2$=H, only one axial hydroxyl group is functionalised. $X_1$—$Y_1$-A-$(Y_2)_n$—$X_2$ is capable of being metabolised in vivo to a platinum (II)-based drug either directly or via an oxidised platinum (IV)-based drug comprising two axial hydroxyl groups.

As used herein, "therapeutically effective amount" relates to the amount or dose of a drug such as a cisplatin prodrug or composition thereof that will lead to one or more desired effects, in particular the inhibition or cessation of tumour growth. A therapeutically effective amount of a substance will vary according to factors such as the disease state, age, sex, and weight of a subject, and the ability of the substance to elicit a desired response in the subject.

In one aspect, this invention provides a prodrug of general formula I:

  (I)

wherein A is an oxidised platinum (IV)-based therapeutically active agent;

$Y_1$ and $Y_2$ are independently selected cleavable bonds between $X_1$ and $X_2$, respectively, and A;

n=0 or 1, wherein when $X_2$ is a substituent according to formula (a), (b), or (c), n is 1;

$X_1$ is selected from the group consisting of a substituent according to formula (a), a substituent according to formula (b), and a substituent according to formula (c):

  (a)

  (b)

  (c)

$X_2$ is selected from the group consisting of H, a substituent according to formula (a), a substituent according to formula (b), and a substituent according to formula (c):

  (a)

  (b)

  (c)

wherein

R is selected from the group consisting of alkyl, alkenyl, alkynyl, branched alkyl, branched alkenyl, branched alkynyl, substituted alkyl, substituted alkenyl, substituted alkynyl groups, and their analogues;

S is selected from the group consisting of (polyethylene glycol)$_m$, wherein m=1-10, an amino acid, and an ethanolamide functionalised amino acid;

L is a linker group that is covalently attached to S—R at one attachment site and to the therapeutically active agent A at a second attachment site via the bond Y to A.

R is generally hydrophobic. Optionally, R has a linear chain length equivalent to 10 to 30 carbon atoms. In one embodiment, R is alpha-tocopherol. In another embodiment, R is an isoprenoid group. In other embodiments, R is an hydroxylated alkyl or hydroxylated alkenyl group. Preferred embodiments of R include but are not limited to: alkyl, alkenyl, alkynyl, branched alkyl, branched alkenyl (isoprenoid), branched alkynyl, substituted alkyl, substituted alkenyl, substituted alkynyl groups and their analogues such as alpha-tocopherol, hydroxylated alkyl or alkenyl groups. In preferred embodiments, R has a chain length equivalent to 10 to 30 carbon atoms. Preferably, the chain length is equivalent to 10 to 24 carbon atoms, more preferably equivalent to 12 to 24 carbon atoms, and more preferably equivalent to 14 to 20 carbon atoms. Generally, R is intended to confer self-assembling properties to A.

In preferred embodiments, R is selected from the group consisting of myristyl, myristoyl, palmityl, palmitoyl, stearyl, stearoyl, oleyl, oleoyl, linoleyl, linoleoyl, linolenyl, linolenoyl, arachidonyl, arachidonoyl, phytanyl, phytanoyl, hexahydrofarnesyl, hexahydrofarnesoyl. Most preferably, R is selected from the group consisting of oleyl, oleoyl, linoleyl, linoleoyl, phytanyl, phytanoyl, hexahydrofarnesyl, hexahydrofarnesoyl, myristoyl and myristoyl chains.

As used herein the term "alkyl" refers to a straight or branched chain hydrocarbon radical having from 10 to 30 carbon atoms, or any range between. The alkyl group is optionally substituted with substituents, multiple degrees of substitution being allowed. Examples of "alkyl" as used herein include, but are not limited to, decane, undecane, dodecane, tridecane, tetradecane, pentadecane, hexadecane, heptadecane, octadecane, nonadecane, icosane, henicosane, docosane, tricosane, tetracosane, pentacosane, hexacosane, heptacosane, octacosane, nonacosane, triacontane, and the like.

As used herein, the term "$C_{10}$-$C_{30}$ alkyl" refers to an alkyl group, as defined above, containing at least 10 and at most 30 carbon atoms respectively, or any range in between (e.g. alkyl groups containing 12-24 carbon atoms are also within the range of $C_{10}$-$C_{30}$).

As used herein the term "alkenyl" refers to an alkyl group containing a double bond. It may also be optionally substituted with substituents; multiple degrees of substitution being allowed.

The terms "optionally substituted" or "may be substituted" and the like, as used throughout the specification, denotes that the group may or may not be further substituted or fused (so as to form a polycyclic system), with one or more non-hydrogen substituent groups. Suitable chemically viable substituents for a particular functional group will be apparent to those skilled in the art. Examples of suitable substituents include, but are not limited to oxygen or sulfur substituted analogues.

In some embodiments according to the current invention, L is a linker group. A "linker" refers to a group that acts as a multifunctional domain between the therapeutically active agent A and the group S—R. Linkers are at least bifunctional, containing at least one functional group (an "attachment site") to anchor the group S—R at one site in the molecule, and another selectively cleavable functional group at another attachment site to anchor the drug A via a Y bond. Preferably, the linker group is a covalent bond.

L includes a selectively cleavable functional group selected from the group consisting of: succinic anhydride, maleic anhydride, glutaric anhydride, chloroacetic acid, hydroxy propane sulfonic acid, glycine and alanine.

The bond Y (including $Y_1$ and $Y_2$) between A and X is capable of being cleaved in vivo upon metabolism of $X_1$—$Y_1$-A-$(Y_2)_n$—$X_2$. Examples of the bond Y include selectively cleavable bonds including but not limited to: esters and carbonates. In a preferred embodiment, the covalent bond is labile so that it may be cleaved when required to release the active drug, but stable enough to resist premature activation. Preferably, Y is an ester bond. $Y_1$ and $Y_2$ may be identical or different, preferably $Y_1$ and $Y_2$ are identical. In a particularly preferred embodiment $Y_1$ and $Y_2$ are both an ester.

In some embodiments according to the current invention, S is a spacer. A "spacer" refers to a bifunctional group that links directly to the therapeutically active domain A or via a linker L on one end and the hydrophobic group R on the other end. The spacer supports improved solvation of the head group in polar solvents and renders better self-assembly properties. Spacers are usually bifunctional, containing one functional group to anchor to the R group on one end of the molecule, and one to attach the drug A or via a linker (L) using a selective and cleavable Y bond.

S is selected from the group consisting of (polyethylene glycol)$_m$, wherein m=1-10, an amino acid, and an ethanolamide functionalised amino acid. In one preferred embodiment, S is selected from the group consisting of (polyethylene glycol)$_m$, wherein m=1-10, wherein m is selected from the group consisting of 1, 2, 3, 4, 5, 6, 7, 8, 9, and 10. In a particularly preferred embodiment, S is selected from the group consisting of polyethylene glycol (PEG)$_{1-10}$, α-carboxy polyethylene glycol (HOOC-PEG)$_{1-10}$ or α-amino polyethylene glycol (H$_2$N-PEG)$_{1-10}$. Preferably, S is (PEG)$_{1-10}$, more preferably S is (PEG)$_{1-6}$. In a particularly preferred embodiment, S is (PEG)$_{3-6}$. In another preferred embodiment, S is an ethanolamide functionalised amino acid, preferably, lysinoyl ethanolamide.

In the present specification, the term "amino acid" refers to a molecule containing both an amino group and a carboxy group. For example, in an α-amino acid, there is an "α-amino group" attached directly to the carbon atom bearing both an amino and a carboxyl group and an "α-carboxyl group" attached directly to the carbon atom bearing both an amino and a carboxyl group. The term "carboxyl" may refer to either a COOH group or a —COO— group. α-amino acids are of the general form H$_2$N—CHR—COOH, where R is a side chain or H. The side chain in general is an alkyl chain, which is optionally substituted, commonly but not necessarily at its distal end. The N terminus of the amino acid is that end at which the amine functionality is located, and the C terminus is the end at which the carboxyl functionality is located. It would be clear to a skilled person that amino acid includes, but is not limited to, the twenty canonical/naturally occurring amino acids, whether in L- or D- form.

As stated herein above, in accordance with the present disclosure, the amino acids can also be chemically functionalised. "Functionalised" refers to a subject amino acid having one or more functional side groups chemically derivatized. Such functionalised molecules include, for example, those molecules in which free amino groups, free carboxyl groups, side chain groups, or a combination thereof, have been derivatized. The terms "functionalised" and "derivatized" are used interchangeably in the specification. An example of a functionalised amino acid is lysinoyl ethanolamide.

Preferably, A is a hydrophilic therapeutically active agent. For example, A is a therapeutically active agent with a logP value of less than 0. In another embodiment, A is an agent capable of being metabolised to a therapeutically active agent, the therapeutically active agent being hydrophilic with a logP value of less than 0. In one embodiment, A is itself a prodrug that is converted, for example by hydrolytic, oxidative, reductive or enzymatic cleavage to the therapeutically active agent by one or more reaction steps. When A itself is a prodrug, the general formula (I) may be considered to describe a compound referred to as a pre-prodrug.

The current invention envisages that the therapeutically active agent may itself be a prodrug instead of a drug or active. It will be recognised by the skilled addressee that in the compounds according to formula (I) above, A is a prodrug that undergoes modification in vivo to release the therapeutically active agent. That is, the platinum-based drug is a precursor to the therapeutically active agent formed in vivo after cleavage of the prodrug by, for instance by a chemical reaction.

The compound A may or may not require further chemical modification steps before resulting in the therapeutically active form. i.e. the compound A may itself be a prodrug, in which case X$_1$—Y$_1$-A-(Y$_2$)$_n$—X$_2$ could be described as a pre-prodrug. In embodiments where the therapeutically active agent is itself a prodrug, at least further chemical modification step/s may then be necessary before the amphiphile prodrug is converted to the therapeutically active form.

A is a therapeutically active platinum (IV)-based agent. In a preferred embodiment, A is selected from the group consisting of cisplatin, oxaliplatin, carboplatin and derivatives thereof. In one preferred embodiment, A is cisplatin or a derivative thereof. In another preferred embodiment, A is oxaliplatin or a derivative thereof. In yet another preferred embodiment, A is carboplatin or a derivative thereof.

Preferably, the amphiphile is a substrate for an enzymatic or a chemical reaction that promotes formation of the therapeutically active form of the therapeutically active agent present in the amphiphile. It is preferable that the amphiphile is predetermined to be one which may be acted upon by a chemical reaction in the patient. More preferably the chemical reaction acts on the cleavable linker.

In one preferred embodiment, the general formula (I) is a compound according to formula (II):

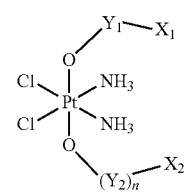

Formula (II)

wherein
Y$_1$ and Y$_2$ are independently selected cleavable bonds between X$_1$ and X$_2$, respectively, and a platinum (IV)-based therapeutically active agent;
n=0 or 1, wherein when X$_2$ is a substituent according to formula (a), (b), or (c), n is 1;
X$_1$ is selected from the group consisting of a substituent according to formula (a), a substituent according to formula (b), and a substituent according to formula (c):

R—                    (a)

R—S—                (b)

R—S—L—            (c)

X$_2$ is selected from the group consisting of H, a substituent according to formula (a), a substituent according to formula (b), and a substituent according to formula (c):

R—                    (a)

R—S—                (b)

R—S—L—            (c)

wherein
R is selected from the group consisting of alkyl, alkenyl, alkynyl, branched alkyl, branched alkenyl, branched alkynyl, substituted alkyl, substituted alkenyl, substituted alkynyl groups, and their analogues;
S is selected from the group consisting of (polyethylene glycol)$_m$, wherein m=1-10, an amino acid, and an ethanolamide functionalised amino acid;
L is a linker group that is covalently attached to S—R at one attachment site and to the platinum (IV)-based therapeutically active agent at a second attachment site via the bond Y to the platinum (IV)-based therapeutically active agent.
R is a molecule capable of conferring self-assembly properties to the compound. Preferably, R is alkyl, alkenyl, alkynyl or isoprenoid of chain length between 12-24 carbon atoms. Preferably, Y is an ester or carbonate, more preferably an ester. Preferably, S is PEG$_m$ wherein m=1-6, more preferably m=3-6. In another preferred embodiment, S is lysinoyl ethanolamide.
In particularly preferred embodiments, the general formula (II) is a compound selected from the group consisting of:
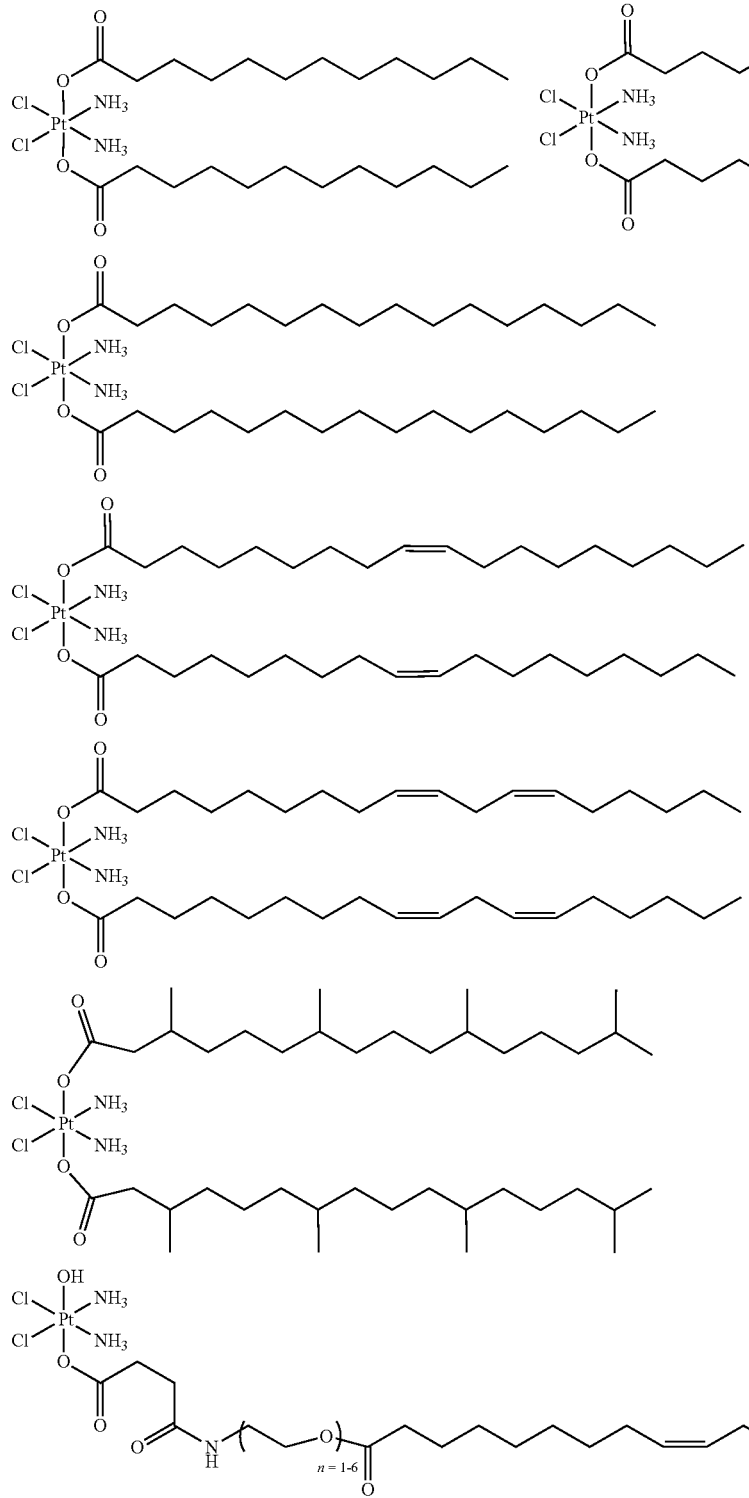

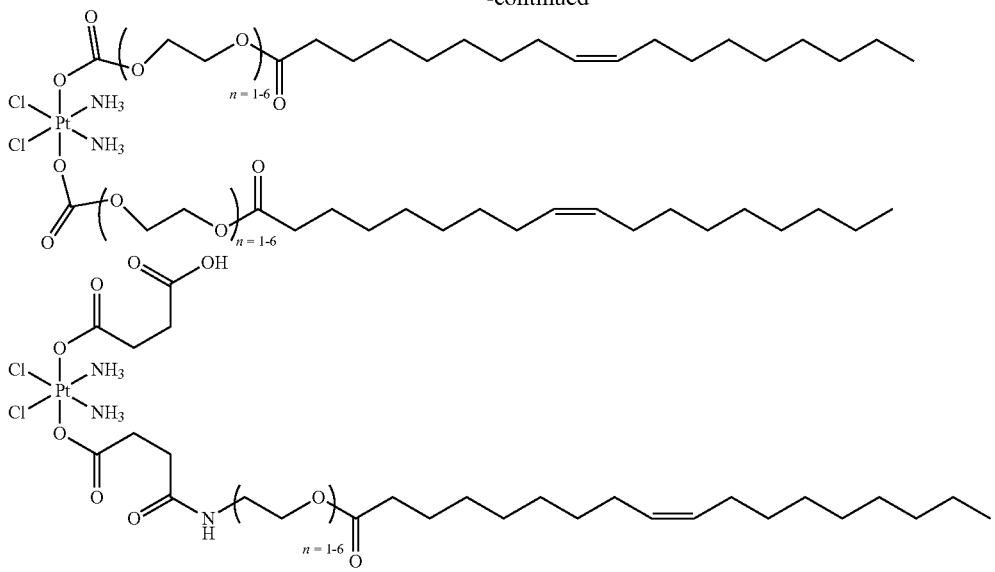

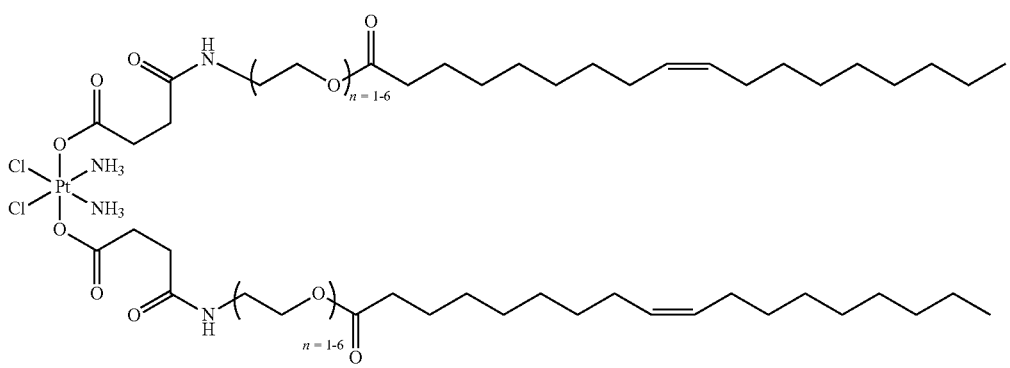

and

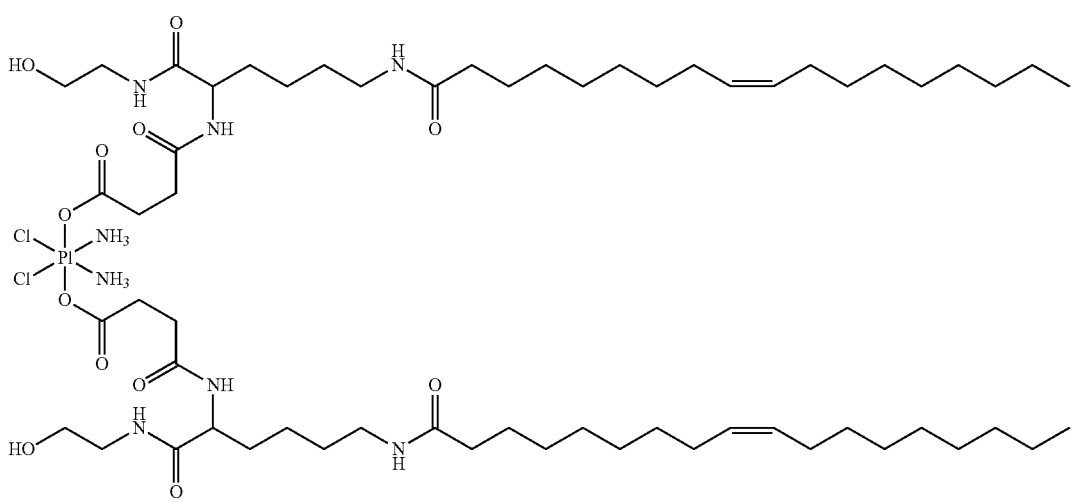

Particularly preferred embodiments of the compounds of the present invention are cis,cis,tranS-[PtCl$_2$(NH$_3$)$_2$ (lauroyl)$_2$]; cis,cis,tranS-[PtCl$_2$(NH$_3$)$_2$ (myristoyl)$_2$]; cis,cis,trans-[PtCl$_2$(NH$_3$)$_2$ (palmitoyl)$_2$]; cis,cis,tranS-[PtCl$_2$(NH$_3$)$_2$ (oleoyl)$_2$]; cis,cis,trans-[PtCl$_2$(NH$_3$)$_2$ (linoleoyl)$_2$]; cis,cis,trans-[PtCl$_2$(NH$_3$)$_2$ (phytanoyl)$_2$]; cis,cis,trans-[PtCl$_2$(NH$_3$)$_2$ (oleoyl carbonate)$_2$]; CiS,Cis,trans-[PtCl$_2$(NH$_3$)$_2$ (Nα-succinoyl)-(Nε-oleoyl)-Lysinoyl-ethanolamide)$_2$]; cis,cis,trans-[PtCl$_2$(NH$_3$)$_2$-(succinoyl-triethylene glycolyl-oleoyl)$_2$], or their pharmaceutically acceptable forms including solvates, hydrates, and salts.

In another preferred embodiment, the general formula (I) is a compound according to formula (III):

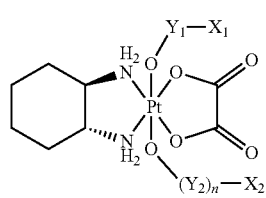
Formula III
wherein $Y_1$, $Y_2$, $X_1$ and $X_2$ are as defined as in Formula II.
In particularly preferred embodiments, the general formula (III) is a compound selected from the group consisting of:
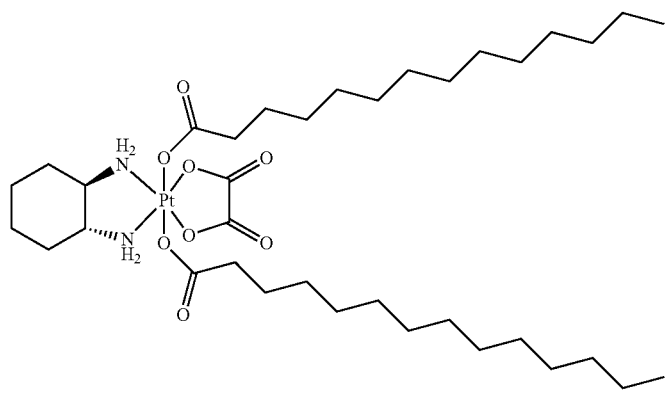
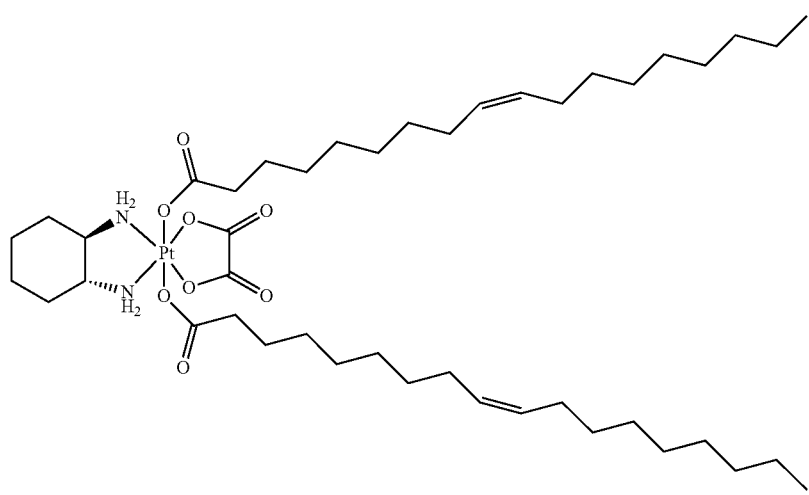

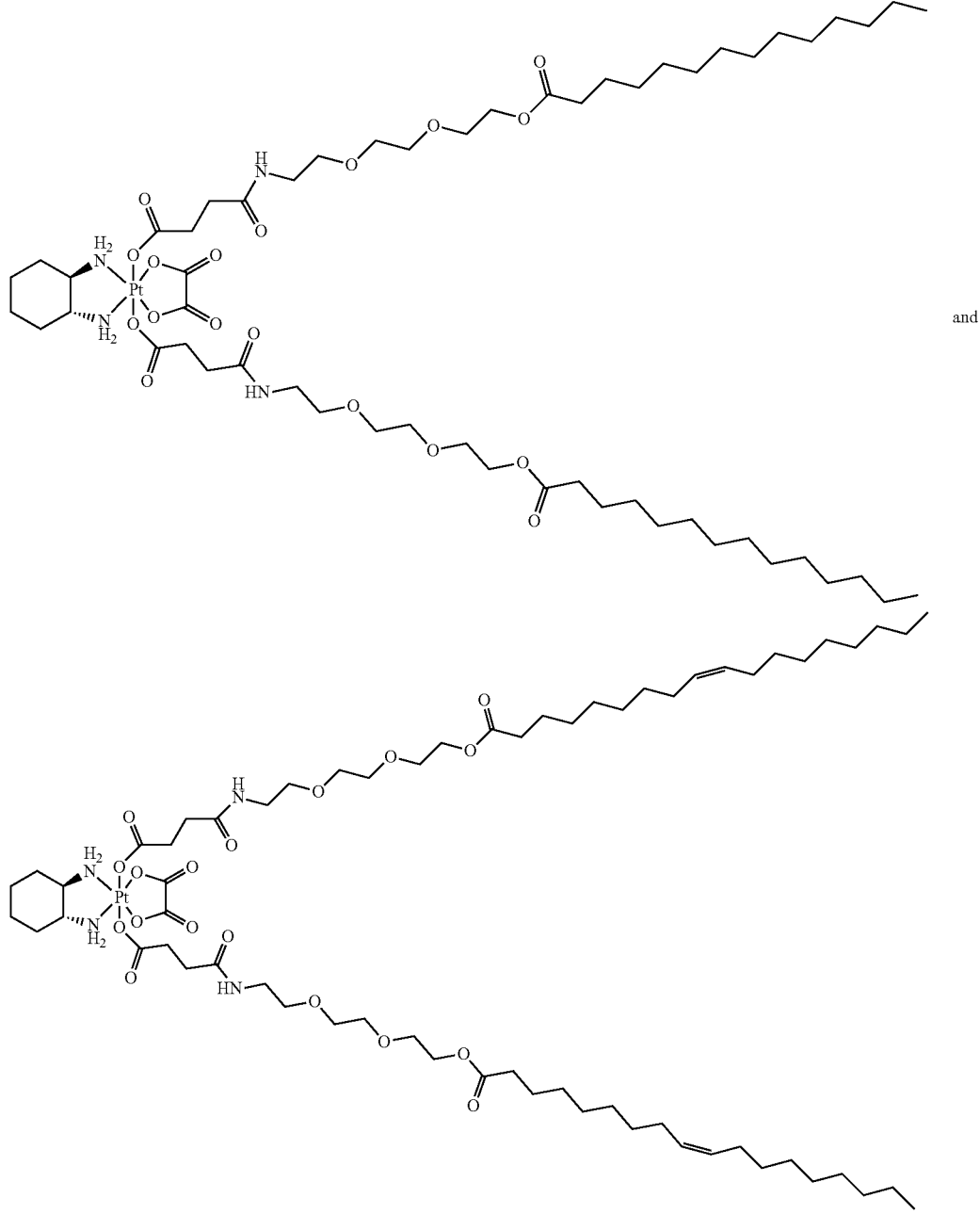
and
In yet another preferred embodiment, the general formula (I) is a compound according to formula (IV):
Formula IV
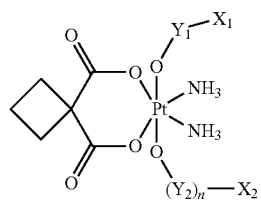
wherein $Y_1$, $Y_2$, $X_1$ and $X_2$ are as defined as in Formula II.

In particularly preferred embodiments, the general formula (IV) is a compound selected from the group consisting of:
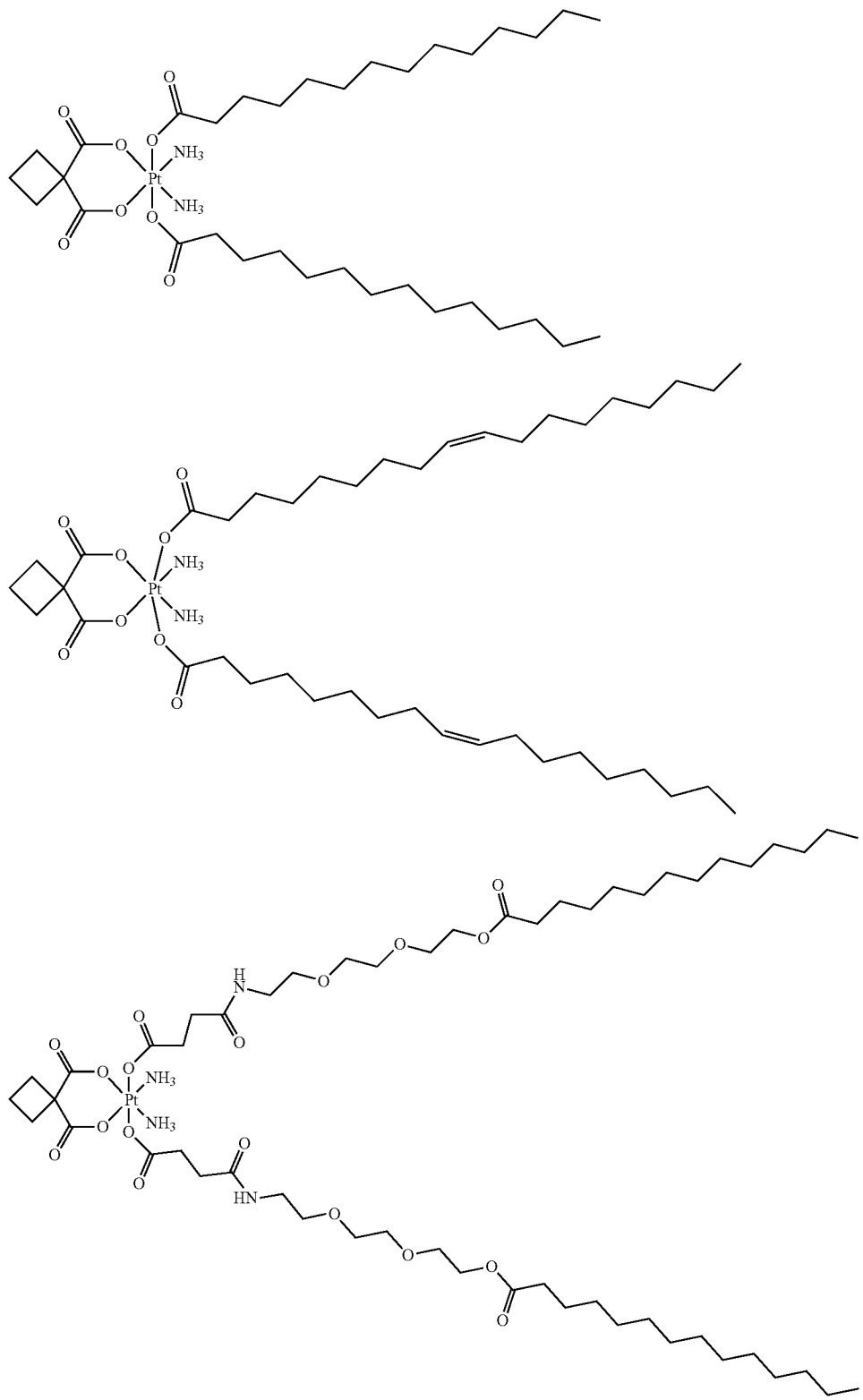
and

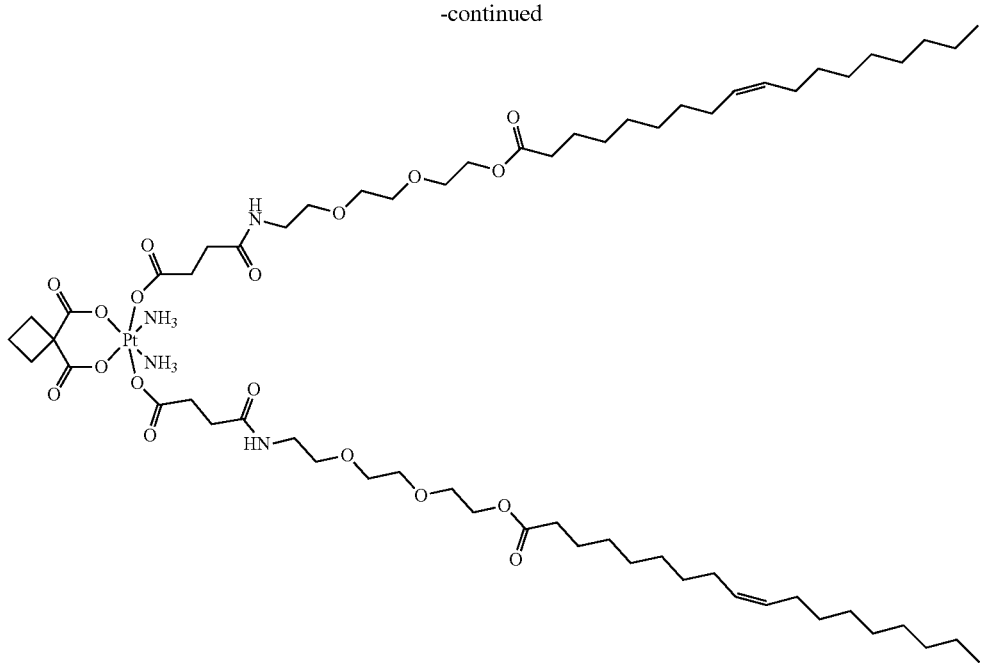

Preferably, a prodrug of general formula (I), (II), (III), or (IV), is capable of forming a self-assembled structure having a lyotropic phase that displays lamellar, cubic, hexagonal, sponge, emulsion, or crystalline lamellar morphologies. More preferably, the phase is a lamellar, cubic, hexagonal, or sponge phase. More preferably still, the phase is an inverse phase.

There is also provided self-assembled structures of the prodrugs of the general formula (I), (II) (III), or (IV), of the above aspect. In one embodiment, the self-assembled structures of the prodrugs of formula (I), (II), (III), or (IV), may be used in combination with an additional component selected from the group consisting of phospholipids, glycerol lipids, cholesterol, other prodrug amphiphiles, hydrophobic drugs, and combinations thereof, in self-assembled structures to form nanoparticles with the capability to deliver combined chemotherapeutics or combined chemotherapeutics and diagnostics.

In some embodiments, a prodrug of the formula (I), (II), (III), or (IV), may be used in combination with a targeting ligand, including a targeting molecule, peptide, antibody, protein or aptamer, to more efficiently delivery the active to the target.

In a particularly preferred embodiment, the self-assembled structures are of compounds of cisplatin (IV) of formula (II) optionally in combination with an additional component selected from the group consisting of phospholipids, glycerol lipids, cholesterol, other prodrug amphiphiles, hydrophobic drugs, and combinations thereof, in self-assembled structures. Such structures may be suitably stabilised for pharmaceutical use benefitting from a surfactant stabiliser such as poloxamer, PEGylated lipids, polysorbate, and combinations thereof.

A preferred embodiment according to the current invention is a self-assembled structure comprising the compounds according to formula (II) above. Preferably the self-assembled structure is of the form lamellar, cubic, hexagonal and sponge phases. Where the self-assembled structure is of the form of a nanoparticle, the average particle size is preferably between 10-500 nm, more preferably 10-200 nm.

Reaction conditions for the synthesis of compounds according to the current invention would be readily determined by one of ordinary skill in the art with a minimum amount of experimentation, and are also exemplified in the accompanying examples. In a particularly preferred embodiment, the compounds are prepared according to scheme 1:

Scheme 1

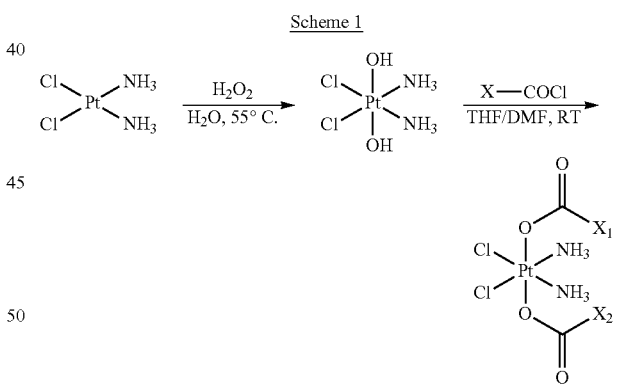

where $X_1$ and $X_2$ are defined as herein described.

Figure 2:
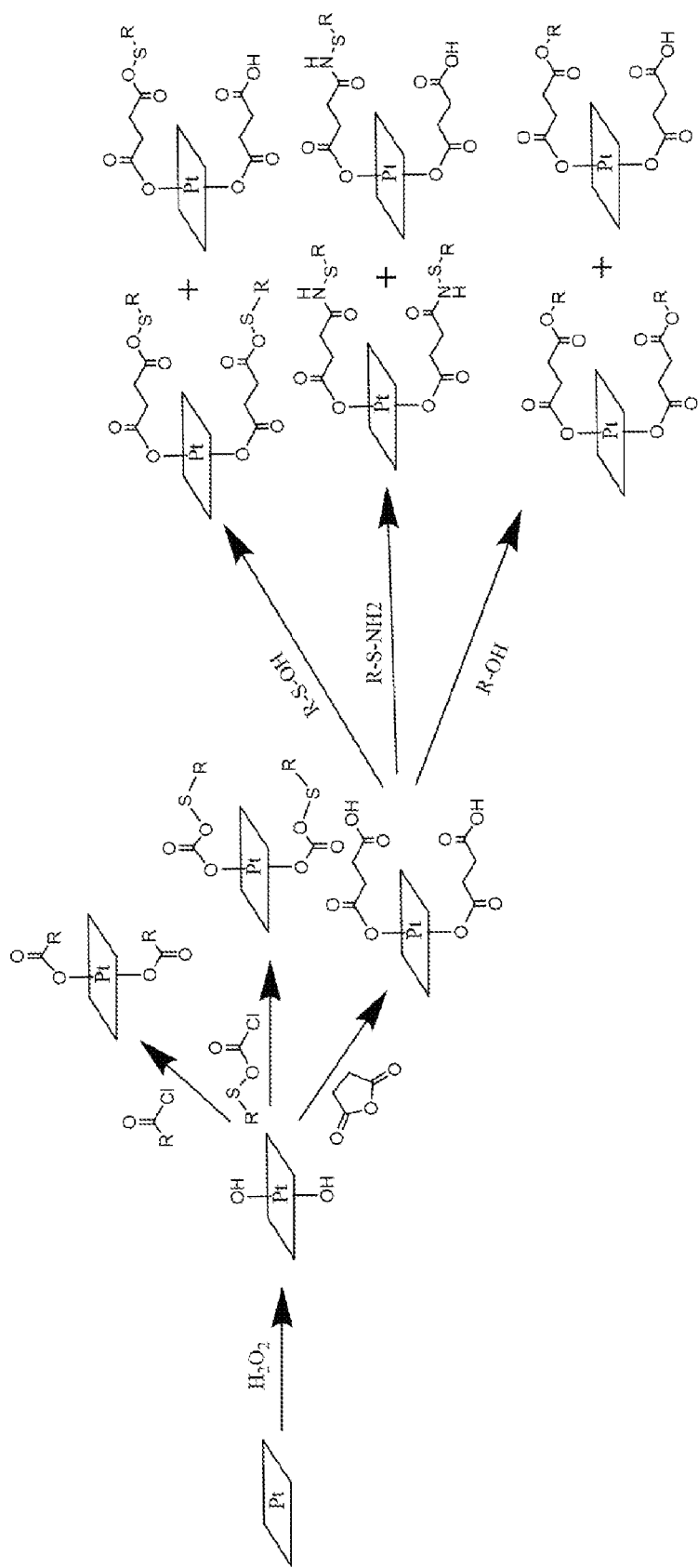
FIG. 2: Schematic flowchart depicting illustrative methods for functionalizing platinum (II) complexes.

Reaction schemes for preparing additional compounds according to the invention are depicted in FIG. 2. It will be understood that these are illustrative and not intended to be exhaustive examples.

Reaction conditions for the synthesis of compounds according to the current invention would be readily determined by one of ordinary skill in the art with a minimum amount of experimentation, and are also exemplified in the accompanying examples.

The starting materials and reagents used to synthesise the compounds according the current invention are either available from commercial suppliers such as, for example, the Chemical Company Sigma-Aldrich Chemical Company (St. Louis, MO), and Merck (Australia), unless otherwise mentioned or are prepared by methods known to those of ordinary skill in the art.

The self-assembled structures of the current invention represent a desirable prodrug delivery system, owing to their modified release properties relative to prodrugs that do not undergo self-assembly into lamellar, inverse cubic, inverse hexagonal and inverse sponge and micellar phases. Without wishing to be bound by theory or mode of action, it is believed that the self-assembled structures of the current invention possess modified release properties firstly, due to the differences of the hydrolytic effect on the self-assembled amphiphile molecules and the complexity of access to single molecules in a self-assembly system compared with that of the isolated single molecules in a non-assembled system. Secondly, in the case of the preferred compounds it is believed that the hydrophobic tail R and the spacer S of the preferred prodrugs result in compounds with different substrate activity for the reduction required to convert the prodrug, and its analogues to cisplatin, or oxaliplatin or carboplatin and thus resulting in a modified release profile for the compounds according to the current invention. Lastly, it is also believed that the hydrolysis of the compounds of the current invention releases fatty chain moieties that may, in itself form self-assembled structures which in turn may alter the local environment and consequently affecting the chemical reduction and transformation of the prodrug to native cisplatin (II).

It is further similarly believed that the self-assembled structures according to the current invention are more desirable than prodrug self-assembled structures that display micellar morphologies. The prodrug lamellar, cubic, hexagonal, sponge phases or inverse micellar nanoparticles according to the current invention possess much greater amphiphile: solvent interface area than any of the previously disclosed prodrug self-assembled structures. Furthermore, unlike normal micelles, the inverse phases according to the current invention are stable in excess aqueous solvent.

In one embodiment, the self-assembled structures of the current invention comprise at least one solvent domain and at least one amphiphile domain, wherein the amphiphile domain comprises at least one prodrug according to formula (I), (II), (III), or (IV), wherein R is defined as any group capable of conferring self-assembly properties to the therapeutically active agent.

The solvent domain of the current invention comprises at least one polar solvent. Examples of polar solvents include solvents conventionally used for amphiphile self-assembly, such as, for example, but not limited to the following: water, glycerol, propylene glycol, butylene glycol, N-methylformamide, hydrazine, propylene carbonate, methanol, ethanol, and selected ionic liquids such as ammonium nitrate, and mixtures thereof.

The solvent may also comprise other components, including e.g. salts, pH buffering agents, sugars, such as glucose and sucrose, stabilizing reagents, such as polysorbate 80, PEG-PPO-PEG copolymer, and more specifically Poloxamer 127, Poloxamer 108, PEG-lipid chains of various PEG length or lipid chains, such as PEG4000-oleoyl, PEG4000-linoleoyl, PEG2000-oleoyl, PEG2000-linoleoyl, PEG10000-oleoyl, PEG10000-linoleoyl, and combinations thereof.

In some embodiments, a prodrug of formula (I), (II), (III), or (IV) may be used in combination with an additional component selected from the group consisting of phospholipids, glycerol lipids, cholesterol, other prodrug amphiphiles, hydrophobic drugs and combinations thereof, in a self-assembled structure selected from liposomes, cubosomes, hexosomes, inverse micellar and sponge-like nanoparticles.

Pharmaceutically active agents that are capable of being incorporated into an amphiphile drug delivery vehicle are known to a person skilled in the art. See, for example, WO 2005/0210046 (DBL Australia Pty Ltd) and WO9830206. Examples of pharmaceutically or therapeutically active agents that may be incorporated into the vehicle include but are not limited to: global proteins and glycoproteins, highly reactive lipids such as prostaglandins, bioactive large drug molecules such as proteins, polysaccharides, DNA and RNA, smaller drug molecules such as cyclosporine, paclitaxel, indomethacin, fenofibrate, progesterone, amphotericin B (AMB), irinotecan, and combinations thereof.

It will be recognised by one skilled in the art that the formation of the desired lyotropic liquid crystalline phases of the current invention require a stringent balance between the specific hydrophilic and hydrophobic domains. Accordingly, the person of ordinary skill in the art will recognise that the selection of X in relation to A will dictate whether the prodrug of the current invention will form either the lyotropic phases and/or the solid lipid particles according to the current invention.

In general, the interplay between surfactant head group, tail and volume is very important in determining lyotropic phase behaviour. The relationship between the molecular geometry and phase behaviour can be described by the critical packing parameter (CPP). CPP is defined as $CPP=v/a_0 l_c$, where v is molecular volume, $a_0$ is the cross-sectional area of the surfactant head group, and $l_c$ corresponds to the hydrophobic tail length. Since the development of this formula, CPP has been used widely in predicting the mesophase behaviour based on the curvature of the molecule. For a molecule with a small head group and a bulky hydrophobe, the CPP value would be equivalent or greater than 1, thereby inducing a mean zero or negative interfacial curvature and potentially formation of inverse mesophase.

The cleavable tail according to the current invention is selected based upon formation of a CPP greater than one when considered in context of the head group according to the current invention. FIG. 1 illustrates this interplay between the head and tail groups. The phases to the left of the lamellar phases have a critical packing density of less than 1 and often they happen at lower concentrations of the amphiphiles. The phases to the right of the lamellar phases have a CPP of more than 1 and usually occur at higher concentration of the amphiphiles. The CPP is not constant for an amphiphile molecule and changes with external factors such as temperature, pressure, concentration of the amphiphile and pH, as well as some additional solvents and additives. However, still this parameter can be used as a simple speculation of the phases that may occur upon hydration of the amphiphiles at room temperature or physiological temperature and at physiological pHs and pressure.

The self-assembly behaviour of amphiphiles in solvent arises because of the preferential interaction between the solvent and either the hydrophilic or hydrophobic portion of the amphiphilic molecules. When an amphiphile is exposed to a polar solvent, the hydrophilic portion of the amphiphile tends to preferentially interact with the polar solvent, resulting in the formation of hydrophilic domains ('solvent domain'). The hydrophobic portion of the amphiphile molecules tend to be excluded from this domain, resulting in the formation of a hydrophobic domain ('hydrophobic domain').

Lyotropic liquid crystals are formed by addition of a solvent to an appropriate solid or liquid amphiphile. They may be classified in terms of the curvature of the interface between the hydrophilic and hydrophobic domains. The curvature between these domains is dependent upon several factors, including the concentration and molecular structure of the amphiphile. When the interface displays net curvature towards the hydrophobic domain, the phase is termed 'normal'. When the interface displays net curvature towards the hydrophilic domain, the phase is termed 'inverse' or 'inverse'. If the net curvature of the system approaches zero, then the resulting phase may possess a lamellar-type structure that consists of planar amphiphile bilayers separated by solvent domains. Alternatively, the net curvature may approach zero if each point on the surface is as convex in one dimension as it is concave in another dimension; such phases are referred to as "bicontinuous cubic" phases. Examples of particular phases that can be formed by self-assembled structures include but are not limited to: micellar (normal and inverse), hexagonal (normal and inverse), lamellar, cubic (normal, inverse and bicontinuous), and other intermediate phases such as inverse micellar cubic, the ribbon, mesh or noncubic 'sponge' bicontinuous phases.

The bulk phases described above may be dispersed to form colloidal particles or nanoparticles that retain the internal structure of the non-dispersed bulk phase. These colloidal particles have also been investigated for their application as drug delivery vehicles. U.S. Pat. No. 5,531,925 discloses colloidal particles or nanoparticles comprising an interior of an amphiphilic-based phase, surrounded by a surface phase anchored to the bi- or mono-layer of the interior phase. The interior phase of the particles may be selected from lamellar, inverse cubic, hexagonal or $L_3$ ("sponge") phases, or mixtures thereof.

When these particles possess the internal structure of an inverse bicontinuous cubic phase, the particles are colloquially referred to as cubosomes. Similarly, when the particles possess the internal structure of an inverse hexagonal phase, they are referred to as hexosomes. When the particles possess the internal structure of a lamellar phase, they are referred to as liposomes. Colloidal particles or nanoparticles may also be formed from 'sponge' phases.

An alternative drug delivery vehicle is solid-lipid particles. Solid lipid particles are comprised of a crystalline amphiphile core stabilised by a surfactant surface layer, such as polysorbate 80, poloxamer and PEGylated lipids. Solid lipid particles have been used as carriers for hydrophobic drugs. For example, Camptothecin, an anticancer agent which was adsorbed on the solid lipid and dispersed as SLNs demonstrated increased drug levels in the brain tissues (Yang 1999, J. control release, 59(3):299-307). The drug loading of conventional SLN is however limited by the solubility of drug in the lipid melt and the structure of lipid matrix.

In an effort to increase drug loadings, the "pharmacosome" approach has been employed. This approach involves generating a prodrug that is capable of assembling into a micelle or liposome. Jin et al. identified some lipid-nucleoside analogues that can form normal lamellar vesicles or higher ordered nanostructures (WO2010063080 A1, U.S. Pat. No. 8,603,999 B2). However, micelles possess substantial drawbacks as phases suitable for drug delivery. Micellar systems can disintegrate under dilution and below the critical micelle concentration (CMC).

Bulk Phases

In one aspect, the self-assembled structure of the current invention comprises at least one bulk phase.

The bulk phase of the current invention comprises at least one phase selected from the following group: lamellar, inverse bicontinuous cubic, inverse hexagonal, inverse micellar cubic, inverse micellar ($L_2$) and sponge ($L_3$). Preferably, the bulk phase comprises at least one phase selected from the group consisting of lamellar, inverse cubic phase, $L_2$ inverse micellar phase, and $L_3$ 'sponge' phase. Most preferably, the bulk phase comprises lamellar, inverse cubic phase, and inverse micellar and sponge phases.

In a preferred embodiment, the bulk phases according to the current invention may be readily produced at a temperature range of about room temperature to about 50° C. and be stable within this temperature range for at least several months.

A preferred embodiment according to the current invention are bulk lyotropic inverse phases. The thermodynamic stability of the lyotropic phases according to the present invention to dilution in excess aqueous solvent means that the bulk phase maintains its primary higher ordered structure, although the lattice parameter might be changed due to the swelling of the amphiphile in water. Most preferably, the lyotropic phase according to the current invention is a lamellar, an inverse bicontinuous cubic phase, an inverse micellar phase or inverse sponge phases.

It will be recognised by one skilled in the art that the observed lyotropic phase is dependent upon temperature. The bulk phases according to the current invention are stable between room temperature and physiological temperature, are preferably stable at temperatures from about 35° C. to about 40° C. and are most preferably stable from about 35° C. to about 37° C.

Processes for preparing bulk phases according to the current invention are known to those skilled in the art. In one embodiment, bulk phases according to the present invention may be prepared by dissolving each amphiphile in an appropriate buffer to the appropriate concentration. Examples of appropriate buffers include but are not limited to physiologically acceptable buffers, such as, for example, phosphate, phosphate buffered saline (PBS), tris(hydroxymethyl)aminomethane (Tris), 4-(2-hydroxyethyl)-1-piperazineethanesulfonic acid (HEPES), Tris-sucrose, Tris-glycine, and glycine buffers.

In another embodiment, the preferred phases according to the current invention are prepared by mechanically mixing molten lipid between room temperature −50° C. until a visually homogenous sample are obtained. Optionally, addition of a co-solvent such as, for example, ethanol in the range of 10-20% by weight may assist the homogenisation process.

Colloidal Particles: Colloidosomes or Nanoparticles

A further aspect of the invention relates to self-assembled structures of the current invention that comprise one or more particles that retain the internal structure of the bulk phase. Such particles are referred to as "colloidosomes" or "nanoparticles".

In one embodiment, the self-assembled structures of the current invention comprise colloidosomes or selected from the following group: liposomes, cubosomes, hexosomes, inverse micelles and "sponge-like" particles (spongosomes). In a preferred embodiment, the colloidal particles are selected from the following group: liposomes, cubosomes, inverse micelles, and spongosomes, most preferably, the colloidal particles or nanoparticles are liposomes, cubosomes, and spongosomes.

In a particularly preferred embodiment according to the current invention, the colloidosomes are derived from a lamellar and inverse phase. The thermodynamic stability of the lyotropic phases according to the present invention means that the bulk phases can progressively be diluted in excess aqueous solvent and dispersed into colloidosomes while maintaining the same liquid crystalline structures as that of bulk phases.

The colloidosomes according to the current invention may be prepared according to processes known to those skilled in the art. For example, colloidosomes/nanoparticles may be prepared by hydration of a thin lipid film in water or saline solution (e.g., phosphate buffered saline). In addition, sugars such as glucose, dextrose might be added to the media. Inverse phase colloidosomes such as inverse cubosomes and hexosomes may be hydrated in water to form gel like bulk phases that can be consequently dispersed into particles by using shear forces such as sonication and high-pressure homogenisation in the presence of stabilising agents.

It will be recognised by one of ordinary skill in the art that in order to prepare stable colloidosomes it is necessary to add a stabilisation agent or fragmentation agent. Suitable fragmentation agents are known to those skilled in the art and include, for example, poloxamer or polysorbate or PEGylated lipids. Poloxamer is the most widely used stabilising agents for inverse phase colloidosomes and is a block copolymer of polyethylene glycol (PEG) and polypropylene oxide (PPO). In a preferred embodiment according to the current invention, the stabilising agent are triblock copolymers of PEG-PPO-PEG of different building blocks. In a particularly preferred embodiment according to the current invention, the stabilisation agent is poloxamer 407, poloxamer 108, and PEGylated lipids (PEG2K-10K-oleoyl).

In one embodiment, colloidal particles or nanoparticles are prepared by dispersing a bulk phase. The bulk phases of the current invention may be dispersed by dropwise addition of an ethanolic solution of the bulk phases into water containing a stabilising reagent. Alternatively, the bulk phase may be dispersed by adding water containing at least one stabilising reagent to the bulk phases. The size of these particles can be controlled by means of vortexing, sonication, filtration, extrusion and homogenisation, techniques well known to one skilled in the art.

In a preferred embodiment, colloidosomes or nanoparticle dispersions according to the current invention are prepared by preferably dispersing the bulk phases of the prodrug-amphiphile mixture with water containing a stabilising reagent using vortexing, and shear forces, such as probe-type ultrasonic homogeniser or an ultrasonic bath. The colloidosome prepared according to this embodiment may optionally be subject to one or more additional processing steps. Such processing methods are known to those skilled in the art and include high pressure homogenisation, and stepwise extrusion through membranes. The membranes employed for stepwise extrusion may possess pore sizes including, for example, 0.8, 0.4, 0.2, 0.1, 0.08 and 0.05 µm. In one embodiment, the processing step is a size selection process.

In a preferred embodiment, the course colloidosomes or nanoparticles preparation is further processed by means of passing through a series of polycarbonate (PC) membranes. The size range of the membranes will be selected by a person skilled in the art according to the desired particle size of the final product. The equipment which may be used for this processing step are known to those skilled in the art, but may include, for example, an extruder.

It will be recognised by the skilled addressee that the size of the nanoparticles of the current invention will depend upon the intended use. For example, for intravenous administration the preferred colloidosome size range is commonly between about 30 nm and about 400 nm. More preferably, the size range is between about 30 nm and about 200 nm for intravenous application.

For delivery of nanoparticles into specific organs such as liver and passive targeting to tumours, particle sizes of between about 30 nm to about 400 nm are contemplated. More preferably particle sizes are about 30 nm to less than about 200 nm. Without wishing to be bound by theory, it is believed that particles of the size between 30-200 nm are passively targeted to cancer cells, owing to their enhanced permeation and retention time in the leakier and chaotic neovasculature of solid tumours. See, for example Matsumura et al and Brannon-Peppas L. et al 2012.

Colloidal Particles: Solid Lipid Particles

A preferred aspect of the current invention seeks to provide solid-lipid particles comprised of at least one platinum (IV)-based prodrug.

Solid lipid particles according to the current invention may be manufactured by processes known to those skilled in the art. See, for example, Mehnert and Mäder 2001.

The appropriate process used to manufacture solid lipid particles according to the current invention may be selected according to the physicochemical properties of the prodrug of the current invention. It will be recognised by one skilled in the art that some of the typical methods to manufacture solid lipid particles, for example those methods that require the lipid to be melted whilst in an aqueous solution, are not applicable to the prodrugs according to the current invention that possess a melting point higher than 100° C.

In one embodiment, the solid lipid particles of the current invention are prepared according to mechanical methods. According to this embodiment, one or more stabilisers are added to the neat amphiphile. Examples of stabilisers include but are not limited to: triblock polymers (for example, poloxamer 407, poloxamer 108, and PEGylated lipids). The amount of stabiliser added to the neat amphiphile may be between about 5-30% (w/w), is preferably between about 10-30% (w/w) and is most preferably between about 15-30% (w/w). To prepare the initial bulk phases, usually 20-70% of water by weight is added to the amphiphile, usually at room temperature (about 22 to about 25° C.). The amphiphile-water mixture is then sheared using methods known to those skilled in the art. In a preferred embodiment, the amphiphile-water mixture is sheared using rough homogenization. The mixture may then undergo further processing to produce particles of desirable size and polydispersity. Methods of further processing are known to those skilled in the art and may include, for example, high pressure homogenization, ultrasonication, and extrusion through different membranes with known pore sizes.

The average size and size distribution of the solid lipid particles according to the current invention are similar to those described for the colloidosomes according to the current invention.

Pharmaceutical Compositions

A further aspect of this invention relates to pharmaceutical compositions of the current invention. In one embodiment, the pharmaceutical composition according to the present invention comprises at least one of compounds according to formula (I). In another embodiment, the pharmaceutical composition comprises at least one self-assembled structure according to the current invention. In a further embodiment, the composition comprises at least one of the solid-lipid particles of the current invention.

In one embodiment, the pharmaceutical composition according to the current invention may be freeze-dried, spray freeze dried, lyophilised or spray-dried powder.

Pharmaceutical compositions according to the present invention may include pharmaceutically acceptable carriers, excipients, diluents, additives and vehicles selected based upon the intended form of administration, and consistent with conventional pharmaceutical practices. Suitable pharmaceutical carriers, excipients, diluents, additives and vehicles are known to those skilled in the art and are described in publications, such as, for example Remington: The Science and Practice of Pharmacy.

The pharmaceutical compositions according to the present invention may further include adjuvants that include, but are not limited to: preservatives, wetting agents or antimicrobial agents. Other adjuvants include but are not limited to: cryoprotectants, spray drying adjuvants, buffers, isotonically adjusting agents, and pH adjusting materials.

The amount of active ingredient that may be combined with the carrier materials to produce a single dosage form will vary depending upon the host treated and the particular mode of administration. Dosage unit forms will generally contain between from about 1 mg to about 5,000 mg of an active ingredient, preferably contain between 20 and 1,000 mg of an active ingredient, and most preferably between 40 and 750 mg of an active ingredient.

It will be understood that reference to the mass of the active ingredient refers to the mass of the platinum (IV)-based prodrug, and not the mass of self-assembled structures or solid lipid particles thereof.

Methods of Treatment

Another aspect of this invention relates to use of a self-assembled structure, solid lipid particle or pharmaceutical compositions thereof according to the present invention for the inhibition of tumour growth. In a preferred embodiment, a pharmaceutical composition of the current invention is used to inhibit growth of solid and metastatic tumours. In a particularly preferred embodiment, a pharmaceutical composition according to the current invention is used to inhibit growth of solid or metastatic tumours associated with pancreatic cancer, colon cancer, colorectal cancer, stomach cancer, ovarian cancer, lung cancer, testicular cancer, bladder cancer, cervical cancer or breast cancer.

In one embodiment there is provided a method of treating or preventing cancer in an individual, including administering to a person in need thereof a self-assembled structure according to the invention.

'Treatment' generally refers to both therapeutic treatment and prophylactic or preventative measures.

The objective or outcome of treatment may be to reduce the number of cancer cells; reduce the primary tumour size; inhibit (i.e., slow to some extent and preferably stop) cancer cell infiltration into peripheral organs; inhibit (i.e., slow to some extent and preferably stop) tumour metastasis; inhibit, to some extent, tumor growth; and/or relieve to some extent one or more of the symptoms associated with the disorder.

Efficacy of treatment can be measured by assessing the duration of survival, time to disease progression, the response rates (RR), duration of response, and/or quality of life.

In one embodiment, the method is particularly useful for delaying disease progression.

In one embodiment, the method is particularly useful for extending survival of the human, including overall survival as well as progression free survival.

In one embodiment, the method is particularly useful for providing a complete response to therapy whereby all signs of cancer in response to treatment have disappeared. This does not always mean the cancer has been cured.

In one embodiment, the method is particularly useful for providing a partial response to therapy whereby there has been a decrease in the size of one or more tumours or lesions, or in the extent of cancer in the body, in response to treatment.

In another embodiment, there is provided a method of providing a prodrug of an active drug in vivo to an individual in need thereof, preferably the active drug is gemcitabine, wherein the prodrug undergoes bioconversion for example, by hydrolytic, oxidative, reductive or enzymatic cleavage to the active drug, preferably at the desired site of action (such as a tumour). The prodrug may exhibit one of more characteristics when compared with the active drug: reduced systemic toxicity, improved pharmacokinetics and/or pharmacodynamics, and improved stability in biological fluids. The prodrug may enable delivery of higher payloads of the active drug, and protect the active drug from premature deactivation, resulting in increased efficacy and reduced systemic toxicity. Preferably, the prodrug is provided in the form of a self-assembled structure. More preferably, the self-assembled structure comprises an additional component selected from the group consisting of: phospholipids, cholesterol, glycerol lipids, prodrug amphiphiles, hydrophobic drugs and combinations thereof. Most preferably, the self-assembled structure comprises an additional component selected from the group consisting of: phospholipids, cholesterol, and combinations thereof.

It will be recognised that the intended form of administration of the self-assembled structure will be as either its bulk phase, as colloidal particles derived therefrom or as solid-lipid particles.

The dosage regimen of a self-assembled structure, solid lipid particle or pharmaceutical compositions thereof according to the current invention will vary depending upon known factors such as the pharmacodynamic characteristics of the compounds, self-assembled structures, colloidal particles or nanoparticles and compositions thereof of the current invention, and their mode and route of administration; the age, sex, health, medical condition, and weight of the patient, the nature and extent of symptoms, the kind of concurrent treatment, the frequency of treatment, the renal, hepatic and cardiovascular and otherwise general health status of the patient in need of such treatment, and can readily be determined by standard clinical techniques.

It will be understood that the invention disclosed and defined in this specification extends to all alternative combinations of two or more of the individual features mentioned or evident from the text or drawings. All of these different combinations constitute various alternative aspects of the invention.

The examples that follow are intended to illustrate but in no way limit the present invention.

Materials:

All solvents were of analytical grade and purchases from Merck Australia. All reagents were obtained from Sigma-Aldrich. Cisplatin,carboplatin and oxaliplatin was purchased from SimagChem, China. Fatty acids and alcohols were purchased from Nucheck Prep INC. (MN, USA). t-Boc-amino (PEG)$_3$- alcohol linker was purchased from Leo Biochem (china).

Instrumentation:

Nuclear magnetic resonance (NMR): The $^1$H NMR spectra (200 MHz) were recorded on a Bruker AC400 spectrometer in deuterated solvent with Tetramethylsilane (($CH_3$)$_4$Si, TMS) as internal standard unless otherwise stated. Solute concentrations were approximately 15 mg/ml in standard 5 mm NMR tubes. The spectra were analysed using mNova software. The chemical shift values (δ) were expressed in ppm, coupling constants were expressed as J values, in Hertz units.

High performance liquid chromatography (HPLC): Analytical HPLC was performed on Waters HPLC equipment (Waters Corporation, Milford, MA, USA), comprising of a 600 solvent delivery system with a 600 automated gradient controller using a Phenomenex Gemini C18 column (5 μm, 4.6×150 mm), an Altech 3300 Evaporative Light scattering (ELS) and a Shimadzu UV-Vis (λ=260 nm) detectors. Mobile phases for the analysis of prodrug amphiphiles consisted of (A) 50:50 $H_2O$/acetonitrile and (B) 60:40 THF/acetonitrile.

Flash column chromatography: Purification of prodrug amphiphiles was performed on a Reveleris® iES flash chromatography system (Grace Division Discover Sciences, Deerfield, IL, USA) using a Reveleris® C18 12 or 40 g, and 80 g columns. Mobile phases for the purification of prodrug amphiphiles or their intermediates consisted of (Buffer A): $H_2O$/Ethanol (90/10), (Buffer B): Ethanol, unless otherwise stated.

Electrospray Ionization Mass Spectroscopy (ESI-MS): Electro-spray ionisation mass-spectroscopy (ESI-MS) was performed on a Finnigan LCQ Advantage MAX ion trap mass spectrometer (Thermo Electron Corporation, San Jose, CA, USA) equipped with ESI and APCI interface. Samples were injected using a syringe pump or an autosampler with LC system (Thermo Electron Corporation, San Jose, CA, USA). Methanol was used as the mobile phase unless otherwise stated.

Physicochemical Characterization

Differential Scanning Calorimetry (DSC): Differential scanning calorimetry (DSC) measurements were performed on a Mettler Toledo DSC 822 system with a Mettler TSO 801 RO sample robot (Mettler Toledo, Switzerland). Samples were prepared by weighing 4-8 mg of the samples into 40 μL aluminium crucibles and sealed. Samples were cooled to −130° C. before heating at a rate of 2.5° C./min up to 300° C. DSC thermograms were recorded using the STARe software package (Mettler Toledo, Switzerland). Indium was used for the calibration of the instrument.

Polarized Optical Microscopy (POM): Samples used for Polarized Optical Microscopy (POM) were prepared by placing a small amount of prodrug amphiphile on a microscope slide and covered with a cover slip. Water was placed on the edges of the cover slip and allowed to flow into the sample by capillary action. The microscope slide was placed in a Linkam PE94 hot stage (Linkam Scientific Instruments Ltd. Surrey, England) and heated at 3° C./min between room temperature and 50° C. The interaction of water and the amphiphile was observed with an OlympusGX51 inverted optical microscope (Olympus Australia Pty. Ltd.; Melbourne, Australia) in the presence and absence of crossed polarizing lenses. Images were captured with a Nikon DS-Ri-1 camera. All images were taken at 100× magnification.

Dynamic Light Scattering (DLS): Particle size distributions of the dispersions were analysed using a Malvern Zetasizer (Nano ZS, Worcestershire, UK) equipped with He—Ne Laser (4 mW, 633 nm). Disposable 40 μL cuvettes with a scattering angle of 90° were used for all the measurements. The samples were equilibrated for 1 min at 25° C. The viscosity and refractive index values were set to 0.8872 cp and 1.330 respectively for all the dispersions. Size distribution was recorded by intensity and by number.

Small Angle X-Ray Scattering (SAXS):

SAXS analyses of the bulk and lyotropic phases of the amphiphiles were performed on a Bruker NanoSTAR laboratory SAXS instrument (Brucker AXS, Kalsruhe, Germany).

The equilibrated lyotropic phases were placed into a demountable button sample cell. For the analysis of the dispersions, a multi-capillary holder was used. Button cells and capillary holder interchangeably fit into a block setup that was temperature-controlled with a Peltier heater-cooler system. 2D scattering images were radially averaged to conventional 1 D scattering plots and as a function of the q value ($Å^{-1}$) where q is the length of the scattering vector which was calculated using the formula $q=(4\pi/\lambda) \sin(\theta/2)$, where λ is the wavelength and θ is the scattering angle.

The mesophases formed were determined by indexing peaks using the reflection laws as described by de Campo et al (Langmuir, 2004. 20(13), 5254-5261). Small angle X-ray scattering patterns of emulsions and liposomes display large broad peaks while liquid crystalline phases of highly ordered nanostructured particles such as cubosomes and hexosomes display distinct sharp peaks. The relative positions of the peaks ("spacing") allows for the elucidation of the symmetry of the structure. The interplanar distance (d) between two reflecting planes may be calculated using the formula $d=(2\pi)/q$, where q is the absolute position of the peak. This, in turn allows for the calculation of the lattice parameter (a), the size of the unit cell, to be calculated.

Cell Proliferation and Cytotoxicity Assays:

Cell proliferation and cytotoxicity assays were performed in different cell lines by MTS (3-(4,5-dimethylthiazol-2-yl)-5-(3-carboxymethoxyphenyl)-2-(4-sulfophenyl)-2H-tetrazolium) assay. Cells were treated with free drug or prodrug nanoparticles, and in different concentrations in medium supplemented with 10% FBS and incubated for 72 hours.

Cell Line Derived Xenograft in Mice:

Subcutaneous xenografts were established by implanting 2-3×$10^6$ cells from cultures of CFPAC-1 or MIAPACA-2 human pancreatic cancer cell lines. Six-week-old male Non-bobese diabetic/severe combined immunodeficient (NOD/SCID) or nonobese diabetic/severe combined immunodeficient-gamma (NSG) mice were obtained from Animal Research Centre, Perth, Australia. These mice were acclimatised for one week in the Kearns Facility, Kolling Institute of Medical Research, the University of Sydney, following standard animal regulation and strict health controls allowing transfer between institutions. Animal care and housing was undertaken in accordance with institutional guidelines of Northern Sydney Local Health District (NSLHD) Animal Care & Ethics Committee (ACEC) (Protocol number 1011-015A).

Tumour growth was measured at least twice a week. When tumours were ~40-100 mm3, the treatments were administered two times weekly by intraperitoneal injection (IP.) for control and gemcitabine alone groups, and intravenously (IV.) injection for nanoparticles groups for 4 weeks. At 30 days each experiment organs and tumours were harvested for analysis.

Histopathology:

Tissue samples were fixed in 10% phosphate buffered formalin and embedded in paraffin. Formalin-fixed, paraffin embedded sections were cut 4-μm thick sections and stained with Mayer's hematoxylin and eosin (H & E). For immunohistochemistry, sections were incubated with the specific antibodies then using the Dako Envision+System-HRP labelled polymer detection kit (DaKo) according to manufacturers' protocol and counterstained with Mayer's hema-

Example 1: Synthesis of cis,cis,trans-[PtCl$_2$(NH$_3$)$_2$ (lauroyl)$_2$], CP-bis (lauroyl)

The method involved the synthesis of cisplatin (IV) (oxoplatin) and conjugation with fatty acyl chlorides.

1. Synthesis of cis,trans,cis-[PtCl$_2$(OH)$_2$(NH$_3$)$_2$], Oxoplatin

Cisplatin (2.00 g, (6.65 mmol) was suspended in Millipore water (50 mL) in a round bottom flask. H$_2$O$_2$ (70 mL, 30% v/v, 10 molar equivalents) was added and the solution was stirred for 1.5 hours at 55° C. The solution was returned to room temperature and then stored in a fridge overnight to crystallise the desired product. The precipitate was collected via vacuum filtration, washed with cold water (5 mL), ethanol (5 mL) and diethyl ether (5 mL) consequently to yield a pale-yellow powder of oxoplatin (2.14 g, 6.41 mmol, 95.9%). $^{195}$Pt NMR (86 MHz, D20) δ 837.

II. Oxoplatin (0.300 g, 0.898 mmol) was suspended in a mixture of DMF (6 mL) and pyridine (2 mL). A solution containing 2 molar equivalents of lauroyl chloride (0.400 g, 1.82 mmol) in THE (3 mL) was added drop wise to the oxoplatin suspension and stirred at 45° C. for 2 hours. At the completion of the reaction the off-white hydrochloride salt was removed by filtration. The resulting solution was evaporated to dryness under reduced pressure. The residue was redissolved in DCM and extracted with water to remove the unreacted oxoplatin. A white precipitate was isolated from the DCM layer. This was collected by filtration and determined to be the desired product. CP-bislauroyl appeared as a white powder (0.560 g, 89.3%). $^1$H NMR (400 MHz, THF-d8): δ 6.23 (m, 6H, —NH$_3$); 2.24 (t, 4H, α-CH$_2$—); 1.54 (m, 4H, β-CH$_2$—); 1.21-1.40 (m, 32H, —CH$_2$—); 0.89 (t, 6H, —CH$_3$). $^{13}$C NMR (400 MHz, THF-d$_8$): δ 183.14, 36.90, 32.94, 30.69, 30.62, 30.51, 30.37, 30.30, 30.18, 26.90 23.62 14.50. $^{195}$Pt-{$^1$H NMR (86 MHz, THF-d8)}: δ 1146 ppm. ESI-MS (50/50 MeOH:THF) −ve mode m/z: 697.80 [M−H]−, 733.47 [M−H+Cl]−, 1395.27 [2M−2H]−, 1431.07 [2M−H+Cl]−.

Example 2: Synthesis of cis,cis,trans-[PtCl$_2$(NH$_3$)$_2$ (myristoyl)$_2$], CP-bis(myristoyl)

Oxoplatin (0.125 g, 0.374 mmol) was suspended a mixture of DMF (6 mL) and pyridine (2 mL). A solution containing 2 molar equivalents of myristoyl chloride (0.185 g, 0.749 mmol) in THE (3 mL) was added drop wise to the oxoplatin suspension and stirred at 45° C. for 2 hours. At the completion of the reaction the off-white hydrochloride salt was removed by filtration. The resulting solution was reduced to dryness under reduced pressure. Unreacted myristoyl chloride was removed by washing with hexane followed by filtration to isolate the desired compound. A DCM/water extraction was performed to purify the compound. A white precipitate was isolated from the DCM layer. This was collected by filtration and determined to be the desired product. CP-bis(myristoyl) appeared as chloride salt white powder (0.182 g, 64.4%). $^1$H NMR (400 MHz, DMSO-d$_6$): δ, ppm 6.48 (m, 6H, NH$_3$); 2.23 (t, 4H, α-CH$_2$—); 1.54 (m, 4H, J=6.84 Hz, β-CH$_2$—); 1.20-1.32 (m, 40H, CH$_2$—); 0.85 (t, 6H, —CH$_3$). 13C NMR (400 MHz, THF-d$_8$): δ 181.17, 36.09, 35.94, 31.63, 29.44, 29.38, 29.31, 29.13, 29.07, 29.05, 28.93, 25.70, 22.34, 13.42. 195Pt-{1H NMR (86 MHz, THF-d$_8$)}: δ 1218 ppm. ESI-MS (500/50 MeOH:THF) −ve mode m/z: 753.60 [M−H]−, 789.33 [M−H+Cl]−, 1507.47 [2M−2H]−, 1543.33 [2M−2H+Cl]−

Example 3: Synthesis of cis,cis,trans-[PtCl$_2$(NH$_3$)$_2$ (palmitoyl)$_2$], CP-bis (Palmitoyl)

Oxoplatin (0.125 g, 0.374 mmol) was suspended a mixture of DMF (6 mL) and pyridine (2 mL). A solution containing 2 molar equivalents of palmitoyl chloride (0.207 g, 0.751 mmol) in THE (3 mL) was added drop wise to the oxoplatin suspension and stirred at 45° C. for 2 hours. At the completion of the reaction the off-white hydrochloride salt was removed by filtration. The resulting solution was reduced to dryness under reduced pressure. Unreacted palmitoyl chloride was removed by washing with hexane followed by filtration to isolate the desired compound. A DCM/water extraction was performed to purify the compound. A white precipitate was isolated from the DCM layer. This was collected by filtration and determined to be desired product. CP-bis(palmitoyl) appeared as a white powder (0.236 g, 74.8%). $^1$H NMR (400 MHz, THF-d$_8$): δ 6.19 (m, 6H, —NH$_3$); 2.25 (t, 4H, α-CH$_2$—); 1.55 (m, 4H, β-CH$_2$—); 1.17-1.41 (m, 48H, CH$_2$—); 0.89 (t, 6H, J=6.07 Hz, —CH$_3$). $^{13}$C NMR (400 MHz, THF-d$_8$): δ 183.26, 37.00, 33.05, 30.84, 30.79, 30.75, 30.63, 30.42, 27.02, 26.02, 25.82, 25.62, 25.39, 25.18, 23.74, 14.61. $^{195}$Pt-{$^1$H NMR (86 MHz, THF-d$_8$)}: δ 1198 ppm. ESI-MS (50/50 MeOH:THF) −ve mode m/z: 809.93 [M−H]−, 846.00 [M+Cl]−, 1619.87 [2M−2H]−, 1655.67 [2M−2H+Cl]−

Example 4: Synthesis of cis,cis,trans-[PtCl$_2$(NH$_3$)$_2$ (oleoyl)$_2$], CP-bis (oleoyl)

Oxoplatin (0.166 g, 0.497 mmol) was suspended a mixture of DMF (6 mL) and pyridine (2 mL). A solution containing 2 molar equivalents of oleoyl chloride (0.300 g, 0.997 mmol) in THE (3 mL) was added drop wise to the oxoplatin suspension and stirred at room temperature overnight. The pH of the solution was maintained at approximately pH 9 using TEA. At the completion of the reaction the off-white hydrochloride salt was removed by filtration. The resulting solution was reduced to dryness under reduced pressure. Unreacted oleoyl chloride was removed by washing with hexane followed by filtration to isolate the desired compound. A DCM/water extraction was performed to purify the compound. A yellow precipitate was isolated from the DCM layer. This was collected by filtration and determined to be desired product. CP-bis(oleoyl) appeared as a yellow wax (0.167 g, 38.9%). $^1$H NMR (400 MHz, THF-d$_8$): δ 6.25 (m, 6H, —NH$_3$); 5.33 (m, 4H, C=C); 2.24 (t, 4H, J=7.54 Hz, α-CH$_2$—); 2.03 (q, 8H, J=5.64 Hz, —CH$_2$—); 1.56 (m, 4H, J=7.14 Hz, β-CH$_2$—); 1.22-1.41 (m, 40H, —CH$_2$—); 0.89 (t, 6H, J=6.82 Hz, —CH$_3$). $^{13}$C NMR (400 MHz, THF-d$_8$): δ 183.24, 130.73, 130.63, 37.01, 33.03, 30.89, 30.66, 30.53, 30.45, 30.41, 28.24, 28.19, 27.01, 26.02, 25.82, 25.62, 23.73, 14.61. $^{195}$Pt-{$^1$H NMR (86 MHz, THF-d$_8$}): δ 1220 ppm. ESI-MS (50/50 MeOH:THF) −ve mode m/z: 861.13 [M−H]−, 896.91 [M−H+Cl]−, 1725.00 [2M−2H]−, 1758.90 [2M−2H+Cl]−.

Example 5: Synthesis of cis,cis,trans-[PtCl$_2$(NH$_3$)$_2$ (linoleoyl)$_2$], CP-bis (linoleoyl)

Oxoplatin (0.48 g, 1.43 mmol) was suspended a mixture of DMF (6 mL) and pyridine (2 mL). A solution containing 2 molar equivalents of linoleoyl chloride (0.86 g, 2.87 mmol) in THF (3 mL) was added drop wise to the oxoplatin suspension and stirred at room temperature overnight. The pH of the solution was maintained at approximately pH 9 using TEA. At the completion of the reaction the off-white hydrochloride salt was removed via filtration. The resulting solution was reduced to dryness under reduced pressure. The compound was isolated by purification on a C18 column using the mobile phase (A) 50:50 H$_2$O/acetonitrile and (B) 60:40 THF/acetonitrile. CP-bis(linoleoyl) appeared as a yellow coloured wax (0.20 g, 16.2%). $^1$H NMR (400 MHz, THF-d$_8$): δ 6.20 (m, 6H, —NH$_3$); 5.25-5.40 (m, 8H, C=C); 2.78 (t, 4H, —CH$_2$—); 2.27 (t, 4H, α-CH$_2$—); 2.06 (m, 8H, —CH$_2$—); 1.54 (m, 4H, β-CH$_2$—); 1.24-1.42 (m, 28H, —CH$_2$—); 0.90 (t, 6H, J=6.64 Hz, —CH$_3$). $^{13}$C NMR (400 MHz, THF-d$_8$): δ 183.28, 130.85, 128.99, 37.01, 32.62, 30.81, 30.52, 30.47, 30.39, 28.20, 27.01, 26.52, 26.02, 25.82, 23.63, 14.59. $^{195}$Pt-{$^1$H NMR (86 MHz, THF-d$_8$)}: δ 1053 ppm. ESI-MS (50/50 MeOH:THF) –ve mode m/z: 857.73 [M–H]–, 893.40 [M–H+Cl]–, 1715.40 [2M–2H]–, 1752.07 [2M–H+Cl]–.

Example 6: Synthesis of cis,cis,trans-[PtCl$_2$(NH$_3$)$_2$ (phytanoyl)$_2$], CP-bis (phytanoyl)

Oxoplatin (0.30 g, 0.88 mmol) was suspended a mixture of DMF (6 mL) and pyridine (2 mL). A solution containing 2 molar equivalents of phytanoyl chloride (0.40 g, 1.80 mmol) in THF (3 mL) was added drop wise to the oxoplatin suspension and stirred at 45° C. for 2 hours. The pH of the solution was maintained at approximately pH 9 using TEA. At the completion of the reaction the off-white hydrochloride salt was removed via filtration. The resulting solution was reduced to dryness under reduced pressure. The compound was isolated by purification on a C18 column using the mobile phase (A) 50:50 H2O/acetonitrile and (B) 60:40 THF/acetonitrile. The compound appeared as a pale yellow-coloured wax (0.15 g, 18.1%). $^1$H NMR (400 MHz, THF-d$_8$): δ 6.24 (m, 6H, —NH$_3$); 2.23-2.37 (m, 2H, α-CH—); 2.03-2.10 (m, 2H, —CH—); 1.89 (m, 2H J=6.3 Hz, —CH—) 1.53 (m, 2H, J=6.65 Hz, β-CH$_2$—); 0.99-1.45 (m, 40H, —CH$_2$—); 0.92 (d, 6H —CH$_2$—); 0.88 (d, 12H, —CH$_2$—); 0.86 (d, 12H, —CH$_3$). $^{13}$C NMR (400 MHz, THF-d$_8$): δ 182.85, 44.55, 38.56, 38.49, 38.45, 38.42, 38.32, 38.24, 33.86, 31.94, 29.99, 28.99, 25.90, 25.30, 25.50, 23.12, 20.25, 20.13. $^{195}$Pt-{$^1$H NMR (86 MHz, THF-d$_8$)}: δ 1044 ppm. ESI-MS (50/50 MeOH:THF) –ve mode m/z: 921.47 [M–2H]–, 957.13 [M–H+Cl]–, 1844.27 [2M–2H]–, 1879.67 [2M–2H+Cl]–.

Example 7: Synthesis of cis,cis,trans-[PtCl$_2$(NH$_3$)$_2$ (oleoyl carbonate)$_2$], CP bis (oleoyl-carbonate)

Oxoplatin (0.150 g, 0.449 mmol) was suspended a mixture of DMF (6 mL) and pyridine (2 mL). A solution containing 2 molar equivalents of oleoyl chloroformate (0.330 g, 0.906 mmol) in THF (3 mL) was added drop wise to the oxoplatin solution and stirred at room temperature overnight. The pH of the solution was maintained at 9 using TEA. At the completion of the reaction, the side product, pyridine hydrochloride salt precipitate, was filtered off. The resulting solution was reduced to dryness under reduced pressure. Unreacted oleoyl chloroformate was removed by washing with hexane followed by filtration. A DCM/water extraction was performed to purify the compound. A white precipitate was isolated from the DCM layer. This was collected by filtration and determined to be desired product. CP-bis (oleoyl-carbonate) appeared as a yellow wax (0.127 g, 32.6%). $^1$H NMR (400 MHz, THF-d$_8$): δ 6.44 (m, 6H, —NH$_3$); 5.33 (m, 4H, C=C); 3.94 (t, 4H, J=6.64, α-CH$_2$—); 2.03 (q, 8H, —CH$_2$—); 1.55 (m, 4H, β-CH$_2$—); 1.22-1.41 (m, 44H, —CH$_2$—); 0.89 (t, 6H, —CH$_3$). $^{13}$C NMR (400 MHz, THF-d$_8$): δ 161.79, 130.69, 130.67, 33.03, 30.92, 30.88, 30.66, 30.54, 30.45, 30.41, 30.27, 28.21, 28.18, 27.10, 26.01, 25.81, 25.61, 23.73, 14.61. $^{195}$Pt-{$^1$H NMR (86 MHz, THF-d$_8$)}: δ 1251 ppm. ESI-MS (50/50 MeOH:THF) –ve mode m/z: 921.40 [M–2H]–, 957.13 [M–H+Cl]–, 1843.20 [2M–2H]–, 1879.00 [2M–2H+Cl]–.

Example 8: Synthesis of (cis,cis,trans-(PtCl$_2$(NH$_3$)$_2$) [(Nα-succinoyl)-(Nε-oleoyl)-lysinoyl-ethanolamide)]$_2$, CP-bis (suc-lys(oleoyl)-ethanolamide)

The title compound synthesis involved a 5-step synthesis to prepare the Nε-Oleoyl lysinoyl-ethanolamide and reaction with Oxaliplatin succinic acid.

Synthesis of Intermediate Compounds

Example 8.1: Synthesis of Intermediate Compound Cis,Cis,Trans-[PtCl$_2$(NH$_3$)$_2$(succinoyl)$_2$] (CP-suc)

Oxoplatin (2.06 g, 6.17 mmol) and succinic anhydride (2.47 g, 25 mmol) were dissolved in DMSO (6 mL) and stirred at 70° C. for 1.5 h. The reaction mixture was then cooled to room temperature and DMSO was removed by Freeze-drying the solution. The residue was precipitated in THF. Subsequent THF washes followed by filtration resulted in a yellow solid. (2.03 g, 61.7% yield). $^1$H NMR (400 MHz, DMSO-d$_6$): δ 12.12 (s, 2H, —OH), 6.44 (bs, 6H, —NH$_3$), 2.45 (m, 4H, —CH$_2$—), 2.34 (m, 4H, —CH$_2$—).

Example 8.11: Synthesis of intermediate compound (Nα-Boc, Nε-Cbz) lysinoyl ethanolamide Nα-Boc-(Nε-Cbz)-Lysine (5.00 g, 13.14 mmol) was dissolved in DMF (20 mL) and reacted with O-(Benzotriazol-1-yl)-N,N,N',N'-tetramethyluronium tetrafluoroborate (TBTU) (5.48 g, 17.07 mmol) by stirring in a round bottom flask for one hour at room temperature. Ethanolamine (1.61 mL, 26.36 mmol) was then added dropwise and pH was adjusted to 9.0 using triethylamine. The reaction was left to stir at room temperature for two hours and the reaction progress was monitored using HPLC and ESI/MS. The product was isolated by purification on a C18 column using the mobile phase (A) 90:10 H$_2$O/EtOH and (B) 100% EtOH. The compound appeared as a white powder (3.35 g, 68.1%). $^1$H NMR (400 MHz, CDCl$_3$) δ 7.33 (s, 5H, CH), 6.60 (s, 1H, —NH) 5.25 (s, 1H, —NH) 5.07 (s, 2H, —CH$_2$—), 4.93 (s, 1H, —OH), 3.99 (s, 1H, CH), 3.66 (t, 2H, —CH$_2$—), 3.39 (dt, —CH$_2$—), 3.18 (q, 2H), 1.79 (s, $^1$H, —NH), 1.69 (s, 2H, —CH$_2$—), 1.50 (m, 2H, —CH$_2$—), 1.41 (s, 9H, —CH$_3$), 1.36 (t, 2H, —CH$_2$—). ESI-MS (MeOH) +ve mode m/z: 446.05[M+H+Na]+.

Example 8.111: Synthesis of Intermediate Compound Nα-Boc-Lysinoyl ethanolamide

Nα-Boc-(Nε-Cbz)-Lysinoyl ethanolamide (3.35 g, 7.91 mmol) was dissolved in methanol and 10% DCM in a hydrogenation flask. Activated palladium carbon (0.34 g) was added to the flask and the contents of the flask was shaken under 40 PSI hydrogen atmosphere overnight using a Parr hydrogenator. The palladium/carbon was filtered using celite. The solution of Nα-Boc-Lysinoyl ethanolamide was then evaporated to dryness to yield a white powder (2.04 g, 88.9%). ESI-MS (MeOH) +ve mode m/z: 289.80 [M+H]+.

Example 8.IV: Synthesis of intermediate compound Nα-amino-(Nε-oleoyl)-Lysinoyl ethanolamide Oleic acid (2.00 g, 7.08 mmol) was dissolved in DMF (10 mL) and TBTU (2.90 g, 9.03 mmol) was added and the reaction mixture was stirred for one hour at room temperature. Nα-Boc-Lysinoyl ethanolamide (2.04 g, 7.05 mmol) was dissolved in DMF and then added to the reaction mixture dropwise. The reaction pH was adjusted to 9.0 and allowed to stir at room temperature for two hours. The reaction was monitored using HPLC and ESI/MS. The compound was isolated by purification on a C18 column using the mobile phase (A) 90:10 $H_2O$/EtOH and (B) 100% EtOH. The Boc group was then removed by stirring the compound in a 4 mL solution of DCM:TFA 50/50 at 4° C. for 30 min. The solution was then evaporated under reduced pressure and used in future steps without any further purification. The compound appeared as a light brown oil (1.71 g, 53.4%). $^1$H NMR (400 MHz, CDCl$_3$) δ 8.28 (bs, 3H, —NH$_2$, NH), 7.96 (s, 1H, —NH), 6.97 (bs, 1H, —OH), 5.31 (q, J=5.4 Hz, 2H, C═C), 3.99 (s, 1H, —CH), 3.18 (m, 4H, —CH$_2$—), 2.21 (t, 2H, —CH$_2$—), 1.97 (m, 4H, —CH$_2$—), 1.51 (m, 6H, —CH$_2$—), 1.36-1.18 (m, 22H, —CH$_2$—), 0.85 (t, J=6.7 Hz, 3H, —CH$_3$). ESI-MS (MeOH) +ve mode m/z: 576.07[M+H+Na]+, 1129.07 [2M+H+Na]+.

Example 8.V: Synthesis of the title compound

Cis,cis,trans-[PtCl$_2$(NH$_3$)$_2$(succinate)$_2$] (0.812 g, 1.52 mmol) was dissolved in DMF (20 mL), followed by addition of 2-(1H-Benzotriazole-1-yl)-1,1,3,3-tetramethylaminium tetrafluoroborate (TBTU) (1.216 g, 3.79 mmol) and TEA (0.530 mL, 3.79 mmol). The reaction mixture was stirred for one hour at room temperature. (Nα-amino-(Nε-oleoyl)-Lysinoyl) ethanolamide (1.377 g, 3.03 mmol) was then added to the solution and the pH was adjusted to 9.0 by addition of TEA. The reaction was left to stir at room temperature for two hours and monitored using HPLC and ESI/MS. The solvents were evaporated off and the residue was redissolved in ethanol and purified on a C18 column using the mobile phase (A) 90:10 $H_2O$/EtOH and (B) 100% EtOH. The compound appeared as a light-yellow wax (1.22 g, 57.1%). $^1$H NMR (400 MHz, DMSO-d$_6$) δ 7.95 (dd, 2H, —NH), 7.81 (q, 2H, —NH—), 7.71 (t, 2H, —NH—), 6.50 (s, 6H, NH$_3$), 5.32 (m, 4H, C═C), 4.64 (m, 2H, —OH), 4.14 (m, 2H—CH), 3.37 (d, 4H, —CH$_2$—), 3.11 (q, J=5.7 Hz, 4H, —CH$_2$—), 2.97 (q, J=6.7 Hz, 4H, —CH$_2$—), 2.46 (d, 4H, —CH$_2$—), 2.33 (m, 4H, —CH$_2$—), 1.98 (m, 12H, —CH$_2$—), 1.61 (m, 4H, —CH$_2$—) 1.46 (m, 8H, —CH$_2$—), 1.39-1.13 (m, 44H, —CH$_2$—), 0.85 (t, 6H, —CH$_3$). $^{13}$C NMR (101 MHz, THF-d$_8$) δ 182.16, 174.27, 173.83, 173.74, 130.73, 130.65, 68.14, 61.98, 54.67, 43.25, 39.84, 37.17, 37.05, 33.04, 30.97, 30.90, 30.68, 30.62, 30.58, 30.55, 30.46, 30.43, 28.27, 28.22, 26.02, 25.89, 25.82, 23.74, 14.62. $^{195}$Pt-NMR (86 MHz, THF-d$_8$): δ 1219 ppm. ESI-MS (MeOH) +ve mode m/z: 1445.92[M+H+Na]+, 423.63 [M+H]+.

Example 9: Synthesis of cis,cis,trans-(PtCl$_2$(NH$_3$)$_2$-(succinoyl-triethylene glycolyl-oleoyl)$_2$), CP-bis (suc-amino-PEG$_3$-oleoyl)

The title compound involved a 3-step synthesis to prepare the amino-triethyleneglycol-oleoyl and reaction with Oxoplatin succinic acid.

Example 9.I: Synthesis of Intermediate Compound oleoyl chloride

Oleic acid (5.5 g, 19.57 mmol) was dissolved in 30 mL DCM and cooled on an ice bath. Oxalyl chloride (5 mL, 58.7 mmol) was added dropwise to the solution for 30 min. The reaction mixture was stirred at 4° C. for an additional 30 min and then returned to room temperature and continued to stir for 1 h. The solvent and excess oxalyl chloride was removed under reduced pressure using a rotary evaporator, and repeated co-evaporation of the residue with additional DCM. The resulting oil was used in further reactions without any further purification.

Example 9.II: Synthesis of intermediate compound amino-triethyleneglycol-oleoyl (Oleyl-PEG$_3$-NH$_2$)

Oleoyl chloride (2.6 g, 8.66 mmol) was dissolved in 20 mL DCM and added dropwise to a 10 mL DCM solution of O-(2-Boc-amino) ethyl O'-diethyleneglycol (2 g, 8.66 mmol) over a period of 10 min. The pH of the reaction mixture was adjusted to 8-9 by addition of 1 mL TEA and stirred for 1 h at room temperature. The completion of the reaction was confirmed by MS and HPLC. The solvent was evaporated under reduced pressure using rotary evaporator, followed by deprotection of the BOC group; the oily residue was redissolved in 10 mL DCM and cooled in an ice bath. Trifluroacetic acid (10 mL) was added and the reaction mixture was stirred at 4° C. for 1 h. The solvent and TFA were evaporated to dryness and the residue redissolved in Ethanol and purified on a Reveleris C18 column using the mobile phase (A) 90:10 $H_2O$/EtOH and (B) 100% EtOH. The compound appeared as a light-yellow oil (3.0 g, yield: 65.2%). ESI-MS (MeOH) +ve mode m/z: 414.22 [M+H].

Example 9.III: Synthesis of the Title Compound

CP-succinate (930 mg, 1.748 mmol), synthesised as described in example 8.1 was dissolved in 2 mL DMF. TBTU (1.4 g, 4.37 mmol) and TEA (353.76 mg, 3.496 mmol) were added to the solution and stirred at room temperature for 1 h. Oleoyl-PEG$_3$ NH$_2$ (1.59 g, 3.846 mmol), dissolved in 5 mL DCM was added to the reaction mixture and the pH was adjusted by adding 1.1 mL of TEA. The reaction mixture was stirred for 30 minutes. solvents were evaporated to dryness and the residue redissolved in ethanol and purified on a on a Reveleris C18 column using the mobile phase (A) 90:10 $H_2O$/EtOH and (B) 100% EtOH to yield 1.3 g of the pure title compound with the total yield of 27.3%.

$^1$H NMR (400 MHz, DMSO-d$_6$) δ 7.85 (2H, —NH—CO), 6.50 (s, 6H, NH$_3$), 5.32 (m, 4H, C═C), 4.2 (t, 4H—CH$_2$—OCO), 3.55 (t, (t, 4H, O—CH$_2$—CH$_2$—O—CO), 3.49 (q, 8H, —CH$_2$—O), 3.37 (t, 4H, —CH$_2$—O), 3.15 (t, 4H, —CH$_2$—NH), 2.4 (t, 4H, α-CH$_2$—), 2.26 (t, 8H, —CH$_2$—CO), 1.98 (m, 8H, —CH$_2$—), 1.61 (m, 4H, —CH$_2$—) 1.46 (m, 4H, β-CH$_2$—), 1.39-1.13 (m, 40H, —CH$_2$—), 0.85 (t, 6H, —CH$_3$). $^{13}$C NMR (101 MHz, THF-d$_8$) δ 182.16, 173.49, 172.07, 130.26, 70.29, 70.14, 69.72, 68.94, 63.63, 40.76, 40.55, 40.34, 40.13, 39.92, 39.51, 34.01, 31.94, 31.90, 29.71, 29.68, 29.45, 29.30, 29.20, 29.17, 29.08, 29.02, 27.18, 25.04, 22.7, 14.62. $^{195}$Pt (THF-d$_8$): δ 1219 ppm. ESI-MS (MeOH) –ve mode m/z: 1323.27[M–H], 1358.97 [M–H+Cl].

Example 10: Synthesis of cis,cis,trans-(PtCl$_2$(-triethyleneglycolyl-oleoyl)), CP-PEG$_3$-monooleoyl and cis,cis,trans-(PtCl$_2$(-triethyleneglycolyl-oleoyl)$_2$), CP-bis (PEG$_3$oleoyl)

The title compounds involved a 4-step synthesis to prepare the triethyleneglycol-oleoyl and reaction with Oxoplatin succinic acid.

Example 10I, II: Synthesis of Intermediate Compound oleoyl-PEG$_3$

Oleic acid (5.0 g, 17.8 mmol) was dissolved in 30 mL DCM and cooled on an ice bath. Oxalyl chloride (5 ml, 49.6 mmol), was added dropwise to the solution for 30 min. The reaction mixture was stirred at 4° C. for an additional 30 min and then returned to room temperature and continued to stir for 1 h. The solvent and excess oxalyl chloride was removed under reduced pressure using a rotary evaporator, and repeated co-evaporation of the residue with additional DCM. The resulting oil was used in further reactions without any further purification.

Oleoyl chloride (2.67 g, 8.9 mmol) was dissolved in 20 mL DCM and added dropwise to a 10 mL DCM solution of triethylene glycol (5.34 g, 35.6 mmol) over a period of 10 min. The pH of the reaction mixture was adjusted to 8-9 by addition of 1.28 mL TEA and stirred for 1 h at room temperature. The completion of the reaction was confirmed by MS and HPLC. The solvent was evaporated under reduced pressure using rotary evaporator, the residue was redissolved in Ethanol and purified on a Reveleris C18 column using the mobile phase (A) 90:10 H$_2$O/EtOH and (B) 100% EtOH. The compound appeared as a transparent oil (3.0 g, yield: 81.5%). ESI-MS (MeOH) +ve mode m/z: 415.00 [M+H].

Example 10.III: Synthesis of Intermediate Compound oleoyl-PEG$_3$-chloroformate To PEG$_3$ oleoyl (1.0 g, 2.4 mmol), which was dissolved in 10 mL DCM, was added triphosgene (0.237 g, 0.8 mmol). Anhydrous pyridine (0.2 mL, 2.4 mmol) was added to the mixed solution on an ice bath and the reaction mixture was stirred for 30 min, followed by 2 h at room temperature. The reaction mixture was evaporated to dryness and the residue was used for the next step reaction.

Example 10.IV: Synthesis of the Title Compound

Oxoplatin (1.08 g, 3.07 mmol) was dissolved in a solution of dry DMF (8 mL) and dry pyridine (3 mL). The oleoyl-PEG$_3$-chloroformate from previous step (1.1 g, 2.4 mmol), dissolved in 10 mL DCM was added to the reaction mixture on ice. The reaction continued for 30 min in ice and 2 h at room temperature. The precipitate was removed and the filtrate was evaporated to dryness under reduced pressure and the residue was redissolved in ethanol and purified on a Reveleris C18 column using the mobile phase (A) 90:10 H$_2$O/EtOH and (B) 100% EtOH to yield 270 mg of CP-mono(PEG$_3$ oleoyl) and 60 mg CP-bis(PEG$_3$-oleoyl). Both samples appeared as transparent yellow oil, yield: 15%.

ESI-MS (MeOH) –ve mode m/z: 773.00 [M–H], 808.87 [M–H+Cl] for mono (PEG$_3$-oleoyl) and 1213.27 [M–H], and 1248.93 [M–H+Cl] for bis(PEG$_3$-oleoyl).

$^1$H NMR of CP-mono(PEG$_3$-oleoyl) (400 MHz, CDCl3) δ 6.20 (s, 6H, NH$_3$), 5.32 (m, 2H, C═C), 4.22 (t, 2H O—CO—OCH$_2$), 4.18 (t, 2H CO—OCH$_2$), 3.55-3.75 (m, 8H, O—CH$_2$—CH$_2$), 2.4 (t, 2H, α-CH$_2$—), 1.98 (m, 4H, —CH$_2$—CH), 1.61 (m, 2H, β-CH$_2$—) 1.46 (m, 4H, —CH$_2$—), 1.39-1.2 (m, 20H, —CH$_2$—), 0.85 (t, 3H, —CH$_3$).

$^1$H NMR of CP-bis(PEG$_3$-oleoyl) (400 MHz, CDCl$_3$) δ 6.20 (s, 6H, NH$_3$), 5.32 (m, 4H, C═C), 4.22 (t, 4H O—CO—OCH$_2$), 4.18 (t, 2H CO—OCH$_2$), 3.55-3.75 (m, 8H, O—CH$_2$—CH$_2$), 2.4 (t, 2H, α-CH$_2$—), 1.98 (m, 8H, —CH$_2$—), 1.61 (m, 4H, β-CH$_2$—) 1.46 (m, 4H, —CH$_2$—), 1.39-1.2 (m, 40H, —CH$_2$—), 0.85 (t, 6H, —CH$_3$). $^{195}$Pt-{$^1$H NMR (CDCl$_3$)}: δ 1048 ppm.

Example 11: Synthesis of cis,cis,trans-(PtC12 (succinoyl-triethyleneglycoyl-oleoyl)$_2$), CP-bis(suc-PEG$_3$-oleoyl)

The title compound involved a 4-step synthesis to prepare the oleoyl-PEG$_3$-succinate and reaction with Oxoplatin.

Example 11.I, II: Synthesis of Intermediate Compound oleoyl-PEG$_3$-succinate PEG$_3$-oleoyl (2.0 g, 4.82 mmol), described in example 10.1, was dissolved in 50 mL acetonitrile, and added to succinic anhydride (4.82 g, 48.22 mmol) in 50 ml acetone. TEA was added to the reaction mixture to maintain the pH at 8-9. The reaction mixture was stirred at room temperature for 5 h. The solvents were evaporated to dryness and the residue was redissolved in DCM and extracted with water. The DCM phase was extracted with fresh water for three times. The DCM phase was evaporated to dryness and the residue was redissolved in ethanol and purified on a Reveleris C18 column using the mobile phase (A) 90:10 H$_2$O/EtOH and (B) 100% EtOH to yield 2.3 g of the pure sample, ESI-MS (MeOH) +ve mode m/z: 515 [M+H], 537[M+H+Na].

Example 11.III: Synthesis of Intermediate Compound oleoyl-PEG$_3$-succinoyl chloride To Oleoyl-PEG$_3$-succinate (1 g, 1.95 mmol) in 20 mL DCM was added oxalyl chloride (0.99 g, 7.8 mmol) and the reaction mixture was stirred at RT for 4 h. The excess oxalyl chloride was evaporated under reduced pressure using rotary evaporator. The residue was used for the next step reaction without further purification.

Example 11.IV: Synthesis of the Title Compound

To Oxoplatin (0.15 g, 0.44 mmol), suspended in a mixture of DMF (10 mL) and pyridine (3 mL), was added dropwise a solution of 0.48 g of oleoyl-PEG$_3$-succinoyl chloride, dissolved in 5 mL THF. The reaction pH was adjusted to 8-9 by adding 0.2 mL of DIEA and the reaction mixture was stirred at 45° C. for 2 h. The precipitate was filtered and the filtrate was evaporated to dryness under reduced pressure, using rotary evaporator. The residue was redissolved in 2 mL ethanol and purified on a Reveleris C18 column using the mobile phase (A) 90:10 H$_2$O/EtOH and (B) 100% EtOH to yield 210 mg of a pale-yellow oil (36% yield), ESI-MS (MeOH) –ve mode m/z: 1325.13[M–H], 1360[M+H+Cl].

¹H NMR of CP-bis (suc-PEG₃-oleoyl), (400 MHz, CDCl₃) δ 5.80 (s, 6H, NH₃), 5.32 (m, 4H, C=C), 4.22 (t, 4H O—CO—OCH₂), 3.55-3.75 (m, 8H, O—CH₂—CH₂), 2.71 (t, 8H, CH₂—C=O), 2.32 (t, 2H, α-CH₂—), 1.98 (m, 8H, —CH₂—CH), 1.61 (m, 4H, β-CH₂—) 1.46 (m, 4H, —CH₂—), 1.39-1.2 (m, 40H, —CH₂—), 0.85 (t, 6H, —CH₃). ¹⁹⁵Pt-NMR (CDCl₃): δ 1048 ppm.

Example 12: Synthesis of cis, trans [Pt ((1R, 2R)-1,2 cyclohexanediamine-N,N') (oxalate(2-)O,O') (myristoyl)₂], Oxaliplatin-bis (myristoyl)

The method involved the synthesis of oxaliplatin (IV) and conjugation with myristoyl chlorides.

Example 12.I: Synthesis of Intermediate Compound Cis, trans, [Pt ((1R, 2R)-1,2 cyclohexanediamine-N, N') (oxalate(2-)O,O') (OH)₂], Oxaliplatin (IV)

Oxaliplatin (1.00 g, 2.51 mmol) was suspended in Millipore water (25 mL) in a round bottom flask. H2O2 (35 mL, 30% v/v, 10 molar equivalents) was added and the solution was stirred in dark for 5 hours at 55° C. The solution was returned to room temperature and evaporated under reduced pressure. The residual solution was purified on a Reveleris C18 column using the mobile phase (A) H₂O and (B) H₂O/EtOH (50/50). The pure fractions were evaporated to dryness to obtain a white precipitate of Oxaliplatin (IV) (0.8 g, yield: 73%). ¹H NMR (400 MHz, DMSO-d₆): δ 7.62 (b, 2H, NH₂) 6.8 (b, 2H, —NH₂); 2.52 (m, 2, —CH); 2.0 (t, 2H, —CH₂—); 1.55 (m, 2H, —CH₂—); 1.47 (m, 2H, —CH₂—); 1.2 (m, 2H, —CH₂—). ESI-MS (MeOH) –ve mode m/z: 431.30 [M–H], 862.73 [2M–H].

Example 12.II: Synthesis of Title Compound

Oxaliplatin (IV) (0.210 g, 0.49 mmol) was suspended in a mixture of anhydrous DMF (2 mL) and pyridine (1 mL). A solution containing myristoyl chloride (0.256 g, 1.03 mmol) in DCM (2 mL) was added drop wise to the suspension and stirred at 45° C. for 2 hours. At the completion of the reaction the resulting solution was evaporated to dryness under reduced pressure. To the residue was added hexane and stirred for 10 min at room temperature. A white precipitate was formed which was removed by centrifugation and decanting Hexane. The residue was dissolved in DCM and extracted with water to remove the unreacted oxaliplatin (IV). The DCM layer was evaporated to dryness to obtain a white residue and determined to be the desired product. Oxaliplatin bis-myristoyl appeared as a white powder (0.390 g, yield: 94%). ¹H NMR (400 MHz, DMSO-d₆): 8.42 (b, 4H, —NH₂);, 8.21 (b, 4H, —NH₂); 2.59 (m, 2, —CH—NH₂); 2.09-2.33 (m, 6H, α-CH₂—, cyclohexane —CH₂—), 1.36-1.60 (m, 8H, —CH₂—, O—CH₂—); 1.2-1.36 (m, 40H, —CH₂—); 1.15 (m, 2H, —CH₂—). 0.89 (t, 6H, —CH₃). 13 C NMR (400M MHz, DMSO-d₆): 180.8, 174.3, 174.1, 163.0, 61.0, 35.7, 33.5, 31.2, 28.9, 28.6, 28.4. 25.2, 24.3, 22.0, 14.0. ESI-MS (MeOH) –ve mode m/z: 850.10 [M–H]–, 1702.12 [2M–H]–.

Example 13: Synthesis of cis, trans [Pt ((1R, 2R)-1,2 cyclohexanediamine-N,N') (oxalate(2-)O,O') (succinoylamidetriethyleneglycol-myristoyl)₂], Oxaliplatin-bis(suc-PEG₃-myristoyl)

The title compound involved a 3-step synthesis to prepare the amino-triethyleneglycol-myristoyl and reaction with Oxaliplatin bis-succinic acid.

Example 13.I: Synthesis of Intermediate Compound amino triethyleneglycol-myristoyl (Amino-PEG₃-myristoyl)

Myristoyl chloride (2.18 g, 4.42 mmol) was dissolved in 4 mL DCM and added dropwise to a 12 mL DCM solution of O-(2-Boc-amino)ethyl O'-diethyleneglycol (2 g, 8.66 mmol) over a period of 10 min. The pH of the reaction mixture was adjusted to 8-9 by addition of 0.600 mL TEA and stirred for 1 h at room temperature. The completion of the reaction was confirmed by MS and HPLC. The solvent was evaporated under reduced pressure using rotary evaporator. The oily residue was redissolved in 12 mL DCM and cooled in an ice bath. Trifluroacetic acid (12 mL) was added and the reaction mixture was stirred at 4° C. for 1 h. The solvent and TFA were evaporated to dryness. The residue was redissolved in Ethanol/water and purified on a Reveleris C18 column using the mobile phase (A) 90:10 H₂O/EtOH and (B) 100% EtOH. The compound appeared as a transparent oil (2.0 g, yield: 69.4%). 1H NMR (400 MHz, CDCl₃): δ 4.62 (bs, 2H, —NH₂); 4.31(t, 4H, —CH₂—COO); 4.31(t, 2H, —CH₂—O); 3.77 (t, 2H, —CH₂—O); 3.67 (t, 3H, —CH₂—O); 3.66 (t, 2H, —CH₂—O); 3.19 (t, 2H, —CH₂—NH₂); 2.32 (t, 2H, 2.32 (t, 2H, α-CH₂—); 1.60 (m, 2H, β-CH₂—); 1.18-1.35 (m, 20H, —CH₂—); 0.88 (t, 6H, —CH₃). ¹³C NMR (400 MHz, CDCl₃): δ 183.14, 70.7, 69.8, 69.6, 68.8, 65.7, 62.5, 38.7, 33.7, 31.4, 29.2, 29.0, 28.8, 28.6, 24.4, 22.2, 15. ESI-MS (MeOH) +ve mode m/z: 360 [M+H].

Example 13.II: Synthesis of Intermediate Compound cis, trans, [Pt ((1R, 2R)-1,2 cyclohexanediamine-N,N') (oxalate(2-)O,O') (succinoyl)₂], Oxaliplatin(IV)-bis (suc)

Oxaliplatin (IV) (0.62 g, 1.43 mmol) and succinic anhydride (0.58 g, 5.72 mmol) were dissolved in DMSO (3 mL) and stirred at 75° C. for 1 h. The reaction mixture was then cooled to room temperature and DMSO volume was reduced to 1 mL by freeze-drying the solution. To the residue was added 3 mL ethanol/water 50/50 and purified on a Reveleris C18 column using the mobile phase (A) 100% H₂O and (B) 50/50 (EtOH/water). The pure fractions were collected and evaporated to dryness to yield the pure sample. (0.3 6 g, yield: 40%). ¹H NMR (400 MHz, DMSO-d₆): δ 8.38 (b, 2H, —NH₂) 8.17 (b, 2H, —NH₂); 2.47-2.65 (t, 6H, —CH₂—C=O, —CH—NH₂); 2.44 (t, 4H, —CH₂—C=O); 2.12 (t, 2H, —CH₂—); 1.53 (m, 2H, —CH₂—); 1.42 (m, 2H, —CH₂—); 1.18 (m, 2H, —CH₂—). ¹³C NMR (400M MHz, DMSO-d₆): 179.6, 175.5, 173.55, 163.3, 60.7, 30.7, 30.3, 29.5, 28.8, 23.4. ESI-MS (MeOH) –ve mode m/z: 629.80 [M–H]–, 1260.77 [2M–H]–.

Example 13.III: Synthesis of Title Compound

Oxaliplatin (IV)-bis (suc), 0.34 g (0.54 mmol) was dissolved in 1 ml of anhydrous DMF. TBTU (0.433 g, 1.35 mmol) and TEA (10.19 mL, 1.35 mmol) were added to the reaction mixture and stirred for 30 min. Amino-peg₃-myristoyl (0.426 g, 1.31 mmol) was dissolved in 4 mL DCM and added dropwise to the reaction solution. The pH of the reaction mixture was adjusted to 8-9 by addition of 0.3 mL TEA and stirred for 1 h at room temperature. The completion of the reaction was confirmed by MS and HPLC. The solvents were evaporated under reduced pressure using rotary evaporator. The oily residue was redissolved in 5 mL Ethanol/water 50/50 and purified on a Reveleris C18 column using the mobile phase (A) 90:10 H$_2$O/EtOH and (B) 100% EtOH. The compound appeared as a transparent waxy material (0.212 g, yield: %30). $^1$H NMR (400 MHz, DMSO-d$_6$): δ 8.39 (b, 2H, —NH$_2$); 8.17 (b, 2H, —NH$_2$); 7.95 (t, 2H, C═O—NH), 4.15 (t, 4H, CH$_2$—O—C═O); 3.62 (t, 4H, —CH$_2$—O—) 3.55 (t, 4H, —CH$_2$—O); 3.54 (t, 4H, —CH$_2$—0); 3.42 (t, 4H, —CH$_2$—CONH); 3.21 (m, 4H, —CH$_2$—); 2.72 (m, 2H, —CH$_2$—); 2.47-2.52 (m, 8H, —CH$_2$—C═O); 2.32 (m, 6H, α-CH$_2$—, —CH$_2$—); 2.1 (m, 2H, —CH$_2$); 1.54 (m, 4H, β-CH$_2$—); 1.42 (m, 2H, —CH$_2$—); 1.2-1.36 (m, 40H, —CH$_2$—); 1.21 (m, 2H, —CH$_2$); 0.89 (t, 6H, —CH$_3$). $^{13}$C NMR (400M MHz, DMSO-d$_6$): 180.0, 172.8, 171.2, 163.1, 69.5, 69.4, 69.0, 68.2, 62.9, 33.3, 31.2, 30.7, 28.9, 28.8, 28.6, 28.3, 24.5, 21.9, 14.0. ESI-MS (MeOH) –ve mode m/z: 1312.24 [M–H].

Example 14: Synthesis of cis, trans [(Diamine) (1,1-cyclobutanedicarboxylato) (bis myristoyl)], Carboplatin-bis myristoyl The method involved the synthesis of carboplatin (IV) and conjugation with myristoyl chlorides.

Example 14.I: Synthesis of Intermediate Compound Cis, trans [Pt (Diamine) (1,1-cyclobutanedicarboxylato) (OH)$_2$], Carboplatin (IV)

Carboplatin (1.00 g, 2.68 mmol) was suspended in Millipore water (25 mL) in a round bottom flask. H$_2$O$_2$ (35 mL, 30% v/v, 10 molar equivalents) was added and the solution was stirred for 1.5 hour at 55° C. The solution was returned to room temperature and evaporated under reduced pressure. A white precipitate of carboplatin (IV). More water was added to wash the precipitate and left it at 4° C. overnight. The precipitate was recovered by centrifugation and dried to give carboplatin (IV) (1 g, yield 91.4%). $^1$HNMR (400 MHz, D20): δ 2.53 (t, 4H, —CH$_2$—), 1.90 (m, 4H, —CH$_2$—). $^{13}$C NMR (400 MHz, D20): δ 180.8, 55.9, 32.2, 15.8.ESI-MS (MeOH) –ve m/z:404.80 [M–H]–, 808.70 (2M–2H).

Example 14.II: Synthesis of Title Compound

Carboplatin (IV) (0.3 g, 0.74 mmol) was suspended in a mixture of anhydrous DMF (3 mL) and pyridine (1.5 mL). A solution containing myristoyl chloride (0.34 g, 1.48 mmol) in DCM (2 mL) was added dropwise to the suspension and stirred at 45° C. for 2 hours. At the completion of the reaction the resulting solution was evaporated to dryness under reduced pressure. To the residue was added hexane and stirred for 10 min at room temperature. A white precipitate was formed which was removed by centrifugation and decanting Hexane. The residue was dissolved in DCM and extracted with water to remove the unreacted carboplatin (IV). The DCM layer was evaporated to dryness to obtain a white residue and determined to be the desired product. Carboplatin bis-myristoyl appeared as a white powder (0.55 g, 89%). $^1$H NMR (400 MHz, DMSO-d$_6$): δ 5.97 (m, 6H, —NH$_3$); 2.57 (m, 4H, —CH$_2$); 1.84 (m, 2H, —CH$_2$—); 1.45 (m, 4H, β-CH$_2$—); 1.2-1.35 (m, 40H, —CH$_2$—); 0.89 (t, 6H, —CH$_3$). ESI-MS (MeOH) –ve mode m/z: 824.10 [M–H]–, 1648.90 [2M–H]–.

Example 15: Synthesis of cis, [Pt (Diamine) (1,1-cyclobutanedicarboxylato) (succinylamide-triethyleneglycol-myristoyl)$_2$], Carboplatin-bis(suc-PEG$_3$-myristoyl)

The title compound involved a 3-step synthesis to prepare the amino-triethyleneglycol-myristoyl and reaction with Oxaliplatin bis-succinic acid.

Example 15.I: Synthesis of Intermediate Compound amino-triethyleneglycol-myristoyl (Amino-PEG$_3$-myristoyl)

The synthesis of this compound was noted in example 13.1.

Example 15.II: Synthesis of Intermediate Compound Cis, trans [Pt (Diamine) (1,1-cyclobutanedicarboxylato) (succinoyl)$_2$], carboplatin-bis (suc) (IV)

Carboplatin (IV) (0.62 g, 1.43 mmol) and succinic anhydride (0.58 g, 5.72 mmol) were dissolved in DMSO (3 mL) and stirred at 75° C. for 1 h. The reaction mixture was then cooled to room temperature and DMSO volume was reduced to 1 mL by freeze-drying the solution. To the residue was added 3 mL ethanol/water 50/50 and purified on a Reveleris C18 column using the mobile phase (A) 100% H$_2$O and (B) 50/50 (EtOH/water). The pure fractions were collected and evaporated to dryness to yield the pure sample. (0.42 g, yield; 50%). $^1$H NMR (400 MHz, DMSO-d$_6$): δ 6.35 (m, 6H, NH$_3$); 2.46-2.59 (m, 8H, CH$_2$—C═O, —CH$_2$—); 2.38 (m, 4H, CH$_2$—C═O), 1.84 (m, 2H, —CH$_2$—). $^{13}$C NMR (400M MHz, DMSO-d$_6$): 178.5, 176.1, 173.3, 55.6, 31.1, 29.9, 29.5, 15.6. ESI-MS (MeOH) –ve mode m/z: 603.76 [M–H]–, 1208.65 [2M–H]–, 1813.49 [3M–H].

Example 15.III: Synthesis of Title Compound

Carboplatin (IV)-bis (suc) 0.35 g (0.58 mmol) was dissolved in 3 mL of anhydrous DMF. TBTU (0.453 g, 1.45 mmol) and TEA (0.2 mL) were added to the reaction mixture and stirred for 30 min. Amino-peg$_3$-myristoyl) (0.426 g, 1.27 mmol) was dissolved in 4 mL DCM and added dropwise to the reaction solution. The pH of the reaction mixture was adjusted to 8-9 by addition of 0.4 mL TEA and stirred for 1 h at room temperature. The completion of the reaction was confirmed by MS and HPLC. The solvents were evaporated under reduced pressure using rotary evaporator. The oily residue was redissolved in 5 mL Ethanol/water 50/50 and purified on a Reveleris C18 column using the mobile phase (A) 90:10 H$_2$O/EtOH and (B) 100% EtOH. The compound appeared as a transparent waxy material (0.170 g, yield: %22). $^1$H NMR (400 MHz, DMSO-d$_6$): δ 7.92 (t, 2H, O═C—NH); 6.35 (m, 6H, —NH$_3$); 4.15 (t, 4H, CH$_2$—O—C═O); 3.61 (t, 4H, CH$_2$—O—) 3.54 (m, 4H, CH$_2$—O); 3.53 (m, 4H, CH$_2$—O); 3.41 (t, 4H, CH$_2$—O); 3.20 (m, 4H, —CH$_2$—NH—C═O); 2.43-2.59 (m, 8H, —CH$_2$—C═O, CH$_2$); 2.30 (m, 8H, —CH$_2$—C═O, α-CH$_2$); 1.83 (m, 2H, —CH$_2$—); 1.54 (m, 4H, β-CH$_2$); 1.2-1.35 (m, 40H, —CH$_2$—); 0.88 (t, 6H, —CH$_3$). $^{13}$C NMR (400M MHz, DMSO-d$_6$): 178.8, 175.6, 170.3, 169.7, 69.6, 69.4, 68.9, 68.2, 62.90, 38.4, 32.9, 31.2, 28.9, 28.7, 28.6, 28.3, 25.0, 22.0, 14.3. ESI-MS (MeOH) –ve mode m/z: 1287.16 [M–H].

Example 16: DSC of CP-amphiphiles

Figure 3:
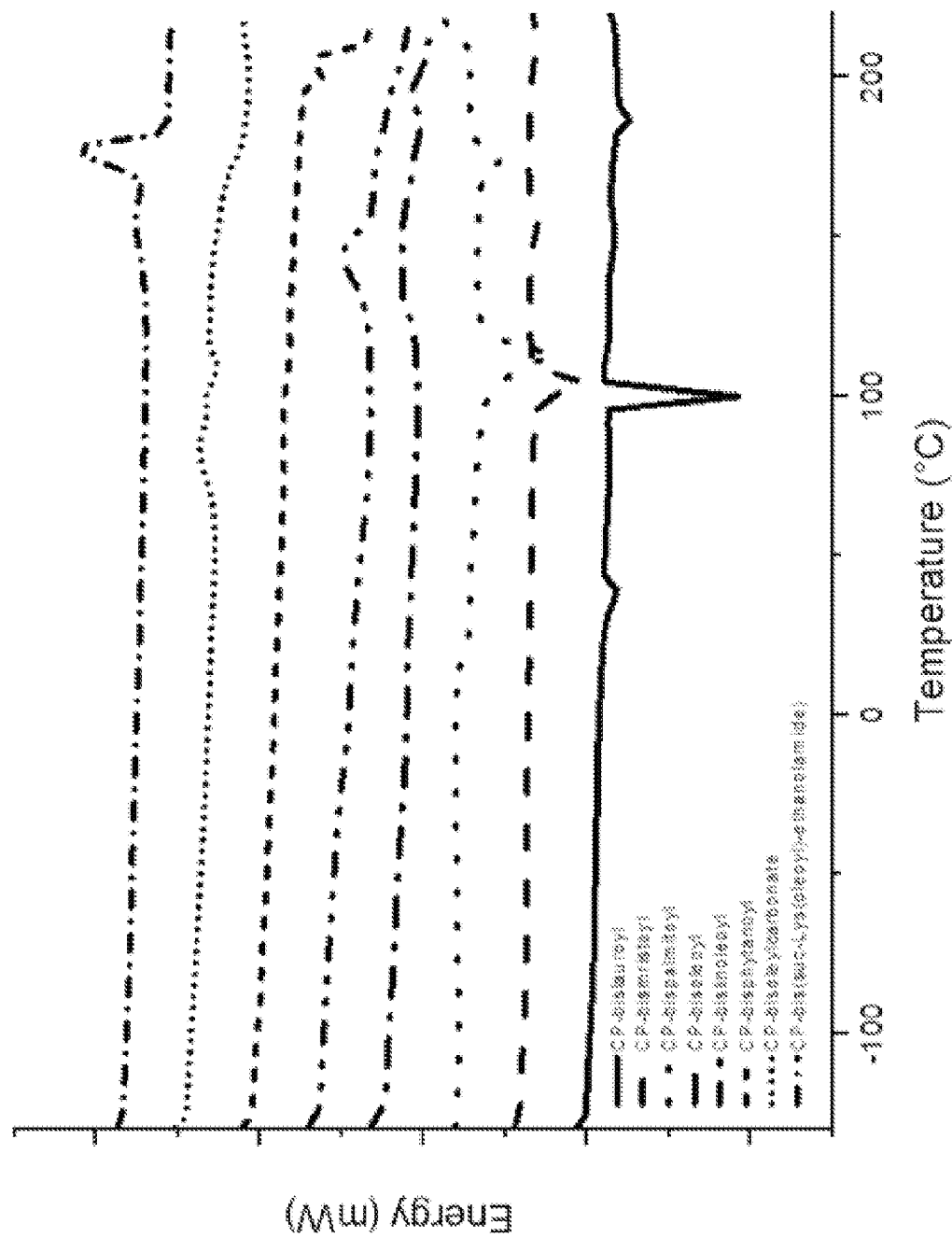
FIG. 3: DSC thermograms of CP-amphiphiles. Transition peaks corresponding to the melting of the amphiphile were not observed, suggesting that the melting point of the amphiphiles may be above the degradation temperature.

DSC was used to measure the temperatures associated with phase transitions of the different cisplatin prodrug amphiphiles (FIG. 3).

Transition temperatures were obtained from the peak minima of the endotherms (Table 2). Enthalpies were obtained by integration of the transition peaks. The DSC thermograms of CP amphiphiles did not show a distinct melting point. The majority of the samples had an endothermic transition temperature related to the transformation of the chains from a rigid fully extended and closely packed crystal to a disordered liquid crystalline fluid chain. This endothermic peak was observed again after a repeat cool and heat-cycle, suggesting a reversible phase transition of states as opposed to degradation. Another endothermic or exothermic transition was observed at higher temperatures, which was the attribute of the degradation of the samples. These peaks were not observed again after a repeat cool and heat-cycle, indicating that the transition corresponds to the degradation temperature of the amphiphile. This phenomenon was also confirmed by visual observation and thermogravimetric analysis (not shown). All the samples without a spacer between the CP (IV) and the hydrophobic acyl chains were solid crystalline compounds, whereas the amphiphiles with the spacers formed either a waxy or oily material.

TABLE 1

Relevant transition temperatures of CP prodrug amphiphiles

| Amphiphile | Transition (° C.) | Enthalpy (Jg$^{-1}$) |
| --- | --- | --- |
| CP-bis (lauroyl) | 37.95 | −13.05 |
|  | 99.90 |  |
|  | (degradation) | −40.82 |
| CP-bis (myristoyl) | 102.34, | −52.7 |
|  | 157.85 | −7.34 |
|  | Degradation |  |
| CP-bis (palmitoyl) | 114.06 | −88.45 |
|  | 176.40 | −31.79 |
| CP-bis (suc-Lys(oleoyl) ethanolamide) | 152.95 | 16.08 |
|  | 177.57 | 86.1 |
| CP-bis (PEG3-oleoyl) | 62.17 | −12.5 |
|  | 94.14 | 88.5 |

Demonstration of Self-Assembly Behaviour

Example 17: Analysis of CP Prodrug Amphiphile Mesophase Behaviour Using Polarized Optical Microscope (POM) and SAXS The formation of lyotropic mesophases is based on the interaction of the prodrug amphiphile with water. Polarized optical microscopy was used to study the liquid crystalline or crystalline structures of the prodrug amphiphiles. This method was used as a preliminary and qualitative investigation to observe the morphological changes of the amphiphile as well as to predict the structural changes of the mesophases which may form upon hydration with water. For each prodrug amphiphile, a small amount of the neat and dry sample was placed on a microscope slide and covered with a cover slip. Water was placed on the edges of the cover slip to allow to flow into the sample by capillary action. Images were captured at 25° C. before and after the addition of water and at 37° C. after exposure to water. 37° C. was selected due to its physiological relevance. Samples were equilibrated for 30 minutes at each temperature which was controlled using a temperature-controlled hot stage. The changes in the appearance of the texture of the amphiphile, such as formation of new dark bands or birefringence after exposure to water suggests the capacity of the prodrug amphiphile to form various mesophases upon hydration.

CP-bis (lauroyl) showed no observable difference after hydration with water at either 25 or 37° C. This indicated that water was not able to interact with the amphiphile or penetrate the crystalline structure. CP-bis(oleoyl), CP-bis (linoleoyl), and CP-bis (phytanoyl) as softening and a visual change in the boundary was observed between the amphiphile and water. However, no distinct mesophases were able to be formed. The fact that CP-bis (myristoyl), CP-bis (palmitoyl), CP-bis (oleoyl), CP-bis (linoleoyl), and CP-bis (phytanoyl) were amenable to swelling to some extent indicated the potential of the CP amphiphiles to form lamellar crystalline structures (images not shown). These observations are summarised below (Table 2).

TABLE 2

Mesophases observed by POM at excess water for various amphiphiles are summarised below.

| Amphiphile | Equilibration Conditions | Neat amphiphile at 25° C. | Appearance of the Lyotropic phase at excess water (25° C.-50° C.) |
| --- | --- | --- | --- |
| CP-bis (lauroyl) | 1 h | powder | No distinct mesophases Lamellar crystalline |
| CP-bis (myristoyl) | 1 h | Powder | No distinct mesophases Lamellar crystalline |
| CP-bis (palmitoyl) | 1 h | powder | No distinct mesophases Lamellar crystalline |
| CP-bis (phytanoyl) | 1 h | Pale yellow wax | No distinct mesophases |
| CP-bis (oleoyl) | 1 h | Waxy material | No distinct mesophases |
| CP-bis (linoleoyl) | 1 h | Pale yellow wax | No distinct mesophases |
| Oxaliplatin-bis (myristoyl) | 1 h | White powder | No distinct mesophase |
| Oxaliplatin-bis (suc-PEG3-myristoyl) | 1 h | Transparent Wax | Lamellar |
| Carboplatin-bis (myristoyl) | 1 h | White powder | No distinct mesophase |
| Carboplatin-bis (suc-PEG3-myristoyl) | 1 h | Yellow Wax | Lamellar |

Figure 4:
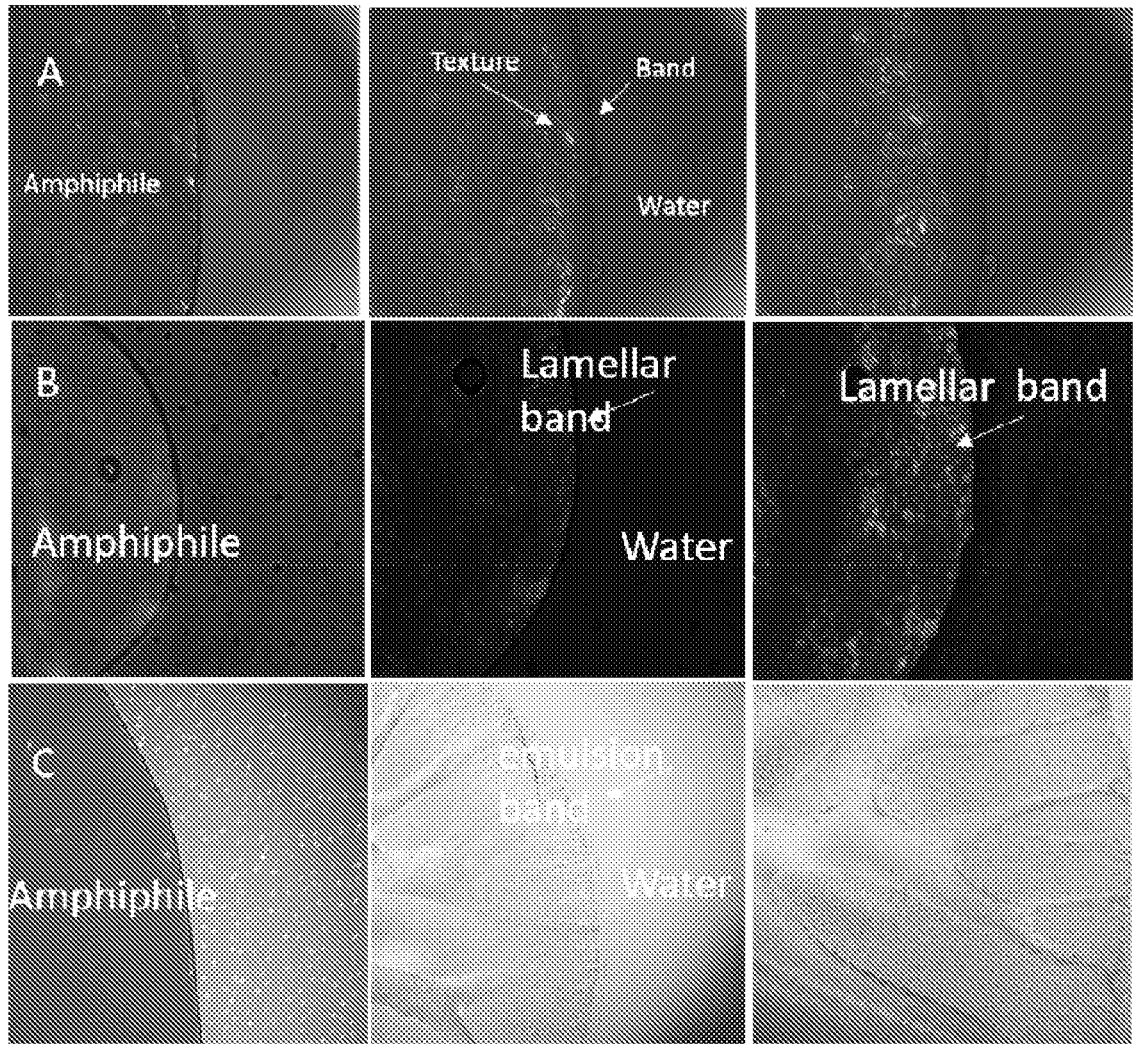
FIG. 4: POM images of typical CP amphiphiles, (A): CP-bis(suc-Lys(oleoyl) ethanolamide), (B): CP-bis(suc-PEG3-oleoyl) and (C): CP-bis(suc-PEG6-oleoyl). Images captured under polarized light microscope at room temperature before the addition of water at 25° C. and after equilibration with water at 25° C. and 37° C. The bands at excess water show that the amphiphiles were able to swell when exposed to water, suggesting the formation of liquid crystalline structures. CP-bis(suc-Lys(oleoyl) ethanolamide) formed a dark band when exposed to water, possibly due to the formation of a cubic phase, whereas the CP-bis(suc-PEG3-oleoyl) and CP-bis (suc-PEG6-oleoyl) showed lamellar and emulsified bands ($L_2$ or $L_3$) mesophases.

Representative images of CP prodrug amphiphiles of CP-bis (suc-lys(oleoyl) ethanolamide), CP-bis (PEG$_3$-oleyl) and CP-bis (suc-PEG$_6$-oleoyl) are shown in FIG. 4.

Water was able to penetrate amphiphiles structures with a spacer between the CP and the hydrophobic chain, demonstrating the possibility of the formation of lyotropic liquid crystalline mesophases. CP-bis (suc-lys(oleoyl)-ethanolamide) demonstrated a dark band at the boundary between the amphiphile and water suggesting the formation of possible cubic phases, which broadened at 37° C. (FIG. 4a). CP-bis (PEG$_3$-oleyl), demonstrated the formation of a lamellar liquid crystalline structures by formation of a new distinct birefringent texture on the boundary with water as shown in FIG. 4b. The CP-bis (suc-PEG$_6$-oleoyl) showed the formation of a less disordered $L_2$ or $L_3$ mesophase, (FIG. 4C).

Example 18: Characterisation of CP Prodrug Amphiphile Mesophase Using Synchrotron Small Angle x-Ray Scattering (SSAXS) and SAXS The SAXS scattering patterns of the neat and hydrated cisplatin amphiphiles were obtained (FIG. 5) and the lattice parameters (unit cell dimensions) were calculated (Table 3). The scattering patterns of the neat CP amphiphiles were characterized by sharp equidistant peaks which are indicative of a lamellar crystalline structure (Lc). Two sets of equidistant peaks, corresponding to two distinct lattice parameters, were observed in all the amphiphiles with aliphatic chains. The aliphatic amphiphiles (CP-bis (lauroyl), CP-bis (myristoyl), and CP-bis (palmitoyl) demonstrated an increase in lattice parameter as the hydrocarbon chain length increased, because the longer chains occupy a larger area. CP-bis (oleoyl), CP-bis (linoleoyl) and CP-bis (phytanoyl) demonstrated one set of equidistant peaks. The two sets of equidistant peaks in the scattering pattern of the aliphatic cisplatin amphiphiles demonstrated two distinct lamellar crystalline phases and may be explained by interdigitation of the lipid chains depending on its orientation. Orientation of the lipid chains in the opposite direction in the trans form may result in full interdigitation or tilting of the chains in a putative arrangement. In this arrangement, the packing of the amphiphile in the crystalline lattice is tighter as the chains are oriented in such a way that it minimizes space. This type of crystalline structure would result in a smaller lattice parameter due to the smaller spacing between each unit cell. Orientation of the lipid chains in a cis form may result in an arrangement that lipid chains are inserted between each other, however due to steric effects only partial interdigitation is able to occur. This partial interdigitation increases the size of the unit cell resulting in a larger lattice parameter. Hydration of the amphiphile with excess water did not affect the scattering pattern or lattice parameter of CP-bis (lauroyl), CP-bis(myristoyl), CP-bis (plamitoyl), CP-bis(oleoyl), CP-bis(linoleoyl) or CP-bis(phytanoyl) as shown in FIGS. 5($a$-$f$) and Table 3.

Figure 5:
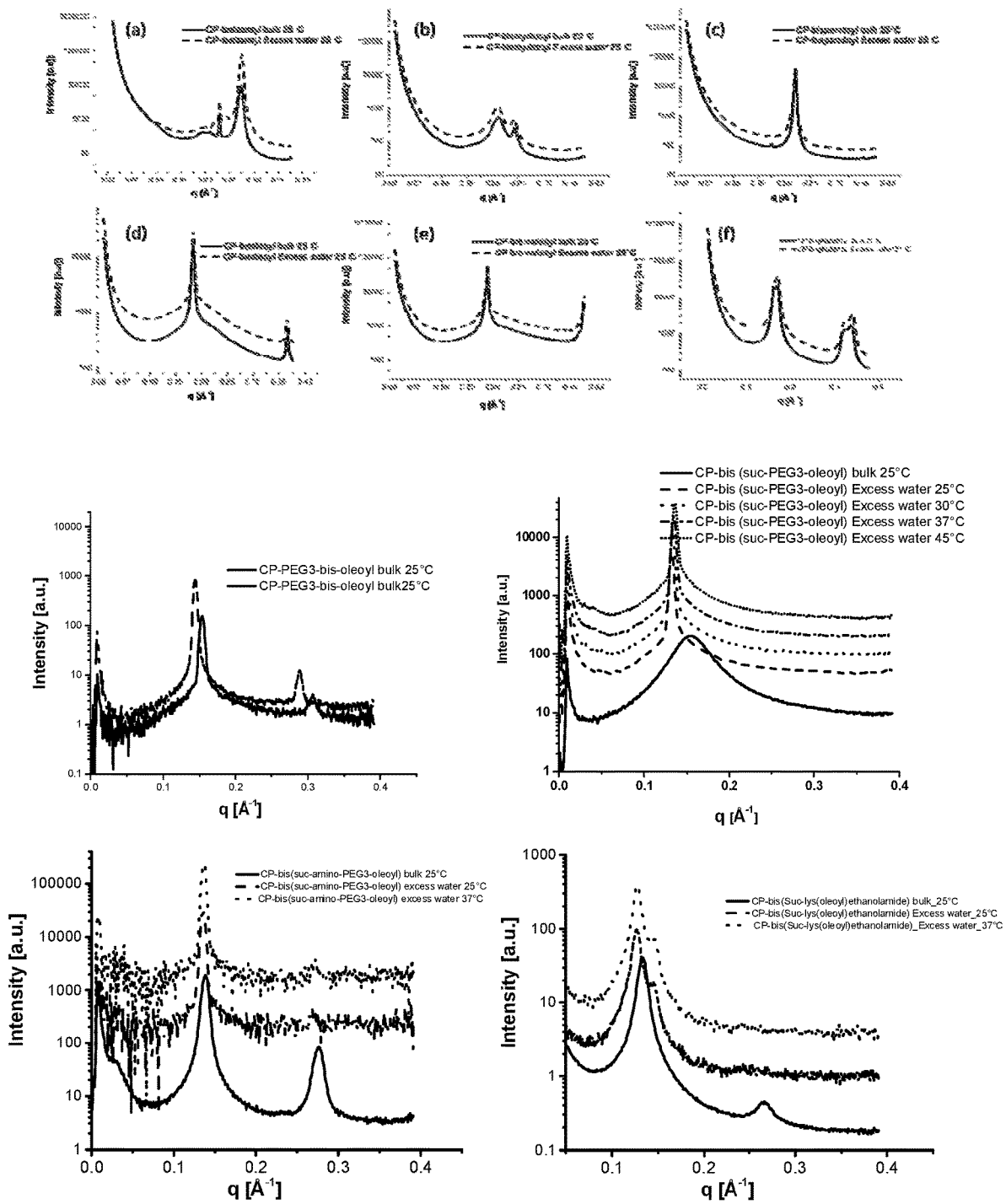
FIG. 5: 1D SAXS diffraction patterns of neat and lyotropic mesophase behaviour of typical cisplatin amphiphile: (a): CP-bis(lauroyl), (b): CP-bis(myristoyl), (c): CP-bis (palmitoyl), (d): CP-bis(oleoyl), (e): CP-bis(linoleoyl), (f): CP-bis(phytanoyl) (g): CP-bis(suc-PEG3-oleolyl), (h): CP-bis(suc-PEG3-oleoyl), (i):CP-bis(suc-amino-PEG3-oleoyl), (j): CP-bis(suc-Lys(oleoyl) ethanolamide).

The SAXS scattering pattern of the CP amphiphiles with various spacers between CP and the hydrophobic acyl chains are shown in FIG. 5($g$-$J$) and their lattice parameters are tabulated in Table 3. CP-bis ($PEG_3$oleoyl) showed a lamellar crystalline mesophases when non-hydrated, which upon hydration transformed to a lamellar liquid crystalline by swelling and increasing of the lattice parameter (FIG. 5$g$). CP-bis ($PEG_6$-oleoyl) showed a more molten phase by showing a broad peak at q=0.153 Å$^{-1}$. Upon hydration with excess water (70/30 w % of water/amphiphile) this molten phase swelled with water and transformed to a lamellar liquid crystalline mesophases with a lattice parameter of 47.42 Å. At 37° C. the lattice parameter decreased to 47.0 Å. The CP-bis (suc-Lys(oleoyl)-ethanolamide) neat amphiphile displayed a scattering pattern with equidistant peaks which is representative of a lamellar crystalline phase with a lattice parameter of 47.0±0.5 Å (FIG. 5$h$). Hydration of the amphiphile with water resulted in the formation of a cubic phase with Ia3d symmetry (gyroid) with a lattice parameter of 121.38±0.5 Å. When the sample was heated to 37° C. the lattice parameter decreased to 121.1±0.5 Å$^{-1}$.

TABLE 3

The phase behaviour of various CP-amphiphiles, at various temperatures. LC (Lamellar crystal), Lα: lamellar liquid crystal, Ia3d: Gyroid inverse cubic.

| Amphiphile | Neat non-hydrated (lattice parameter: Å) | Hydrated (lattice parameter: Å) |
| --- | --- | --- |
| CP-bis (lauroyl) | $L_{C1}$ (23.1 ± 0.5) | $L_{C1}$ (23.1 ± 0.5) |
|  | $L_{C2}$ (27.5 ± 0.5) | $L_{C2}$ (27.5 ± 0.5) |
| CP-bis (myristoyl) | $L_{C1}$ (25.9 ± 0.5) | $L_{C1}$ (25.9 ± 0.5) |
|  | $L_{C2}$ (29.9 ± 0.5) | $L_{C2}$ (29.9 ± 0.5) |
| CP-bis (palmitoyl) | $L_{C1}$ (28.4 ± 0.5) | $L_{C1}$ (28.4 ± 0.5) |
|  | $L_{C2}$ (36.0 ± 0.5) | $L_{C2}$ (36.0 ± 0.5) |
| CP-bis (oleoyl) | $L_{C1}$ (34.2 ± 0.5) | $L_{C1}$ (34.2 ± 0.5) |

TABLE 3-continued

The phase behaviour of various CP-amphiphiles, at various temperatures. LC (Lamellar crystal), Lα: lamellar liquid crystal, Ia3d: Gyroid inverse cubic.

| Amphiphile | Neat non-hydrated (lattice parameter: Å) | Hydrated (lattice parameter: Å) |
| --- | --- | --- |
| CP-bis (linoleoyl) | $L_{C1}$ (33.5 ± 0.5) | $L_{C1}$ (33.5 ± 0.5 |
| CP-bis (phytanoyl) | $L_{C1}$ (37.3 ± 0.5), 25° C. | $L_{C1}$ (37.3 ± 0.5), 25° C. |
|  | $L_{C1}$ (37.3 ± 0.5), 37° C. | $L_{C1}$ (39.8 ± 0.5 37° C. |
| CP-bis ($PEG_3$-oleolyl) | $L_C$ (40.80 ± 0.5) | Lα (43.93 ± 0.5) 25° C. |
| CP-bis ($PEG_6$-oleolyl) | Molten phase | Lα (47.42 ± 0.5) 25° C. |
|  |  | Lα (47.00 ± 0.5) 37°C |
| CP-bis (suc-aminoPEG$_3$-oleolyl) | $L_C$ (46.20 ± 0.5) | Lα (46.54 ± 0.5) 25° C. |
|  |  | Lα (46.33 ± 0.5) 37° C. |
| CP-bis (suc-lys (oleoyl) ethanolamide | $L_C$ (47.0 ± 0.5) | Ia3d (121.38 ± 0.5) 25° C. |
|  |  | Ia3d (121.1 ± 0.5) 37° C. |

Example 19: Preparation of Colloidal Particles or Nanoparticle Dispersions

The preferred prodrugs according to the current invention can be dispersed into aqueous solution and form colloidal particles or nanoparticles with very fine internal nanostructures and in the size range of 20-1000 nm, by using the following procedure.

Typical nanoparticle dispersions were prepared from each sole prodrug amphiphile or in combination with phospholipids, e.g. dioleoylphosphatidylcholine (DOPC) or Dimyristoylphosphatidylcholine (DMPC) and cholesterol according to the following methods:

The CP prodrug amphiphiles were hydrated with warm PBS containing 10-30% PEG4K-oleoyl or other steric stabilisers such $F_{108}$ or $F_{127}$ and sonicated in a sonicator bath and using a probe sonicator resulting in the lipid emulsion. The nanoparticles were then processed through a polycarbonate membrane (3×400 nm, 3×200 nm and 3×100 nm) using an extruder (Avestin, LipoFast LF-50) in order to ensure homogenous sizing. The CP prodrug-phospholipid/cholesterol nanoparticles were prepared by mixing the CP amphiphiles, DMPC and cholesterol in ethanol, followed by vigorous mixing and gentle evaporation under reduced pressure resulting in a thin film. The thin film was then hydrated with warm PBS containing 10-30% of PEG4K-oleoy solution, sonicated in a sonicator bath and using a probe sonicator resulting in the lipid emulsion. The nanoparticles were then processed through a polycarbonate membrane (3×400, 3×200 nm, 9×100 nm) using an extruder (Avestin, LipoFast LF-50) in order to ensure homogenous sizing between 20-200 nm.

Dispersions used for in vitro or in vivo studies were sterile filtered using a 220 μM filter. The final concentration of the nanoparticle solutions was 10-15 mg/mL. The particle size distribution and morphology of the above dispersions were determined using the method as described above by using a nanosizer and cryo-TEM characterisation methods.

Figure 6:
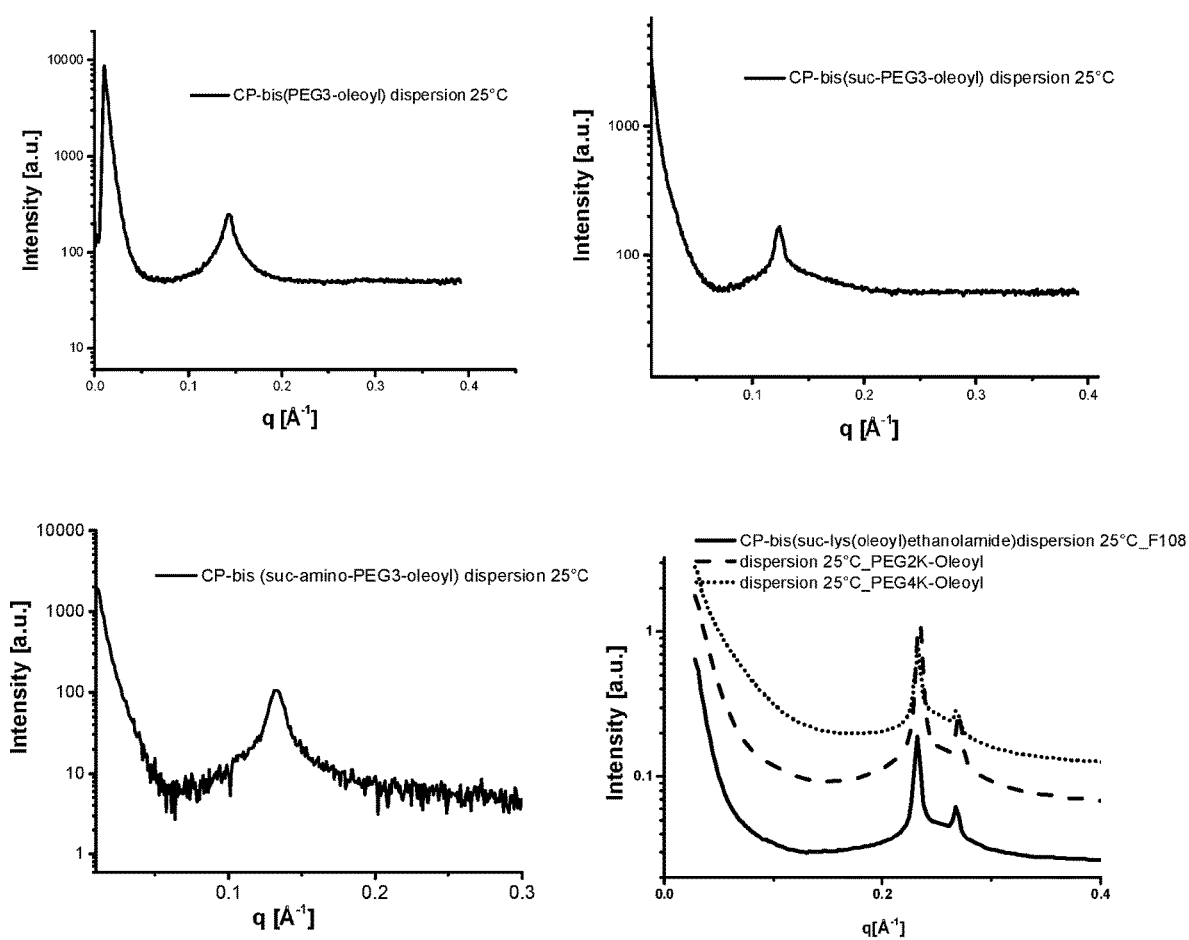
FIG. 6: 1D SAXS diffraction patterns of dispersed nanoparticles of typical cisplatin amphiphile; (a): CP-bis(PEG3-oleoyl), (b): CP-bis(suc-PEG3-oleoyl) (c): CP-bis(suc-amino-PEG3-oleoyl), (d): CP-bis (suc-lys(oleoyl) ethanolamide).

Example 20: Characterisation of CP Prodrug Amphiphile Nanoparticles Using Synchrotron Small Angle x-Ray Scattering (SSAXS) and SAXS Dispersed nanoparticles of CP prodrug amphiphiles with alkyl chains attached directly to the axial hydroxo ligand of cisplatin (IV) were unable to interact with water and form any liquid crystalline structures and therefore could make only solid lipid nanoparticles. However, inserting a hydrophilic spacer such as PEG or lysinoyl ethanolamide via a succinate linker or without were amicable to form liquid crystalline mesophases as evidenced by POM and SAXS analysis. The SAXS of the dispersed nanoparticles of CP-bis (PEG$_3$-oleoyl), CP-bis (suc-aminoPEG3-oleoyl) and CP-bis (suc-Lys(oleoyl)-ethanolamide) are shown in FIG. 6. CP-bis (PEG$_3$-oleoyl), FIG. 6a showed a lamellar dispersed nanoparticle with a lattice parameter of 44.28±0.5 Å consistent with the Lα mesophases shown in the bulk excess water described in example 14. The CP-bis (suc-aminoPEG3-oleoyl) showed a multilamellar dispersed nanoparticle with a lattice parameter of 47.62±0.5 Å (FIG. 6b). Synchrotron SAXS (SSAXS) analysis of CP-bis (suc-Lys(oleoyl)-ethanolamide), FIG. 6C, elucidated the formation of cubosomes with Ia3d symmetry. The first and second scattered peaks are in the ratio of √6, √8, with a lattice parameter of ~121.4 Å. The type of PEG stabilizer did not have an effect on the type of dispersion that was formed. The SSAXS were in agreement with the preliminary results obtained using POM which predicted the formation of cubic phases.

Example 21: Morphology and Size Distribution

21.I Cryo-TEM

Figure 7:
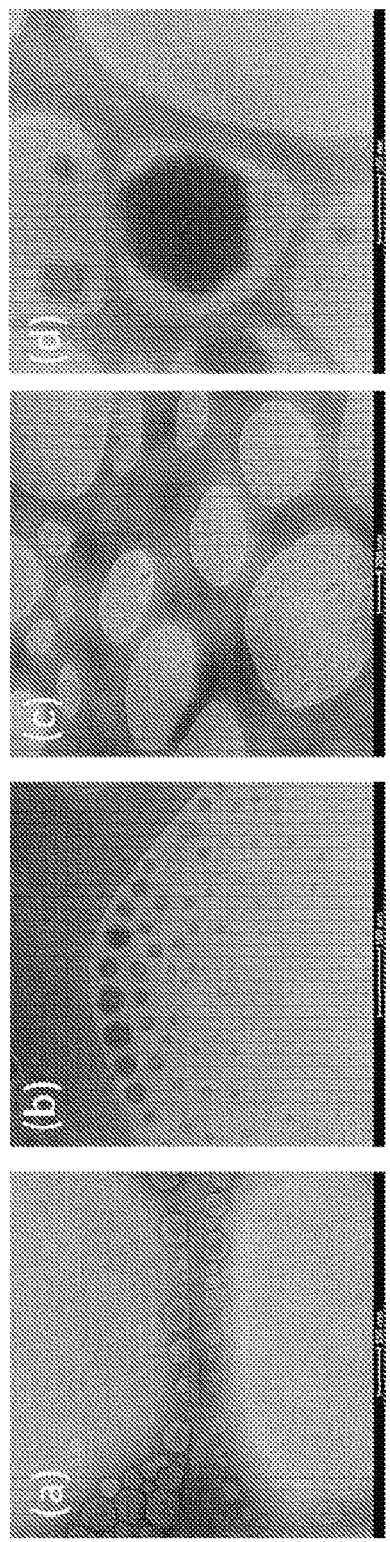
FIG. 7: Cryo-TEM images of CP prodrug nanoparticles, (a): CP-bis(PEG3-oleolyl), (b): bis(suc-aminoPEG3-oleoyl), (c): bis(suc-aminoPEG3-oleoyl)/phospholipid/cholesterol 9/81/10 w/w %, (d): CP-bis(suc-lys(oleoyl) ethanolamide).

Cryo-TEM images of nanoparticles were obtained using a laboratory-built vitrification system allowing humidity to be kept close to 90% during sample plunging and vitrification. 4-5 µl of sample solution was applied to a 300 mesh copper TEM grid coated with a lacey carbon film (ProSciTech, Thuringowa Qld 4817 Australia) and allowed to settle for 30s. The grid was manually blotted for 10-15 s, and the resulting thin film was then vitrified by plunging into liquid ethane. Grids were stored in liquid nitrogen before transferring into a Gatan 626-DH Cryo-holder. Imaging was carried out using an FEI Tecnai 12 TEM, operating at 120 kV, equipped with a MegaView III CCD camera and AnalySis imaging software (Olympus Soft Imaging Solutions). The sample was kept at a temperature of −180° C. and standard low-dose procedures were used to minimize radiation damage. The cryo-TEM of three different nanoparticles made from CP-prodrug amphiphiles only are shown in FIG. 7 (a, b and d). CP-prodrug nanoparticles of various structures showed various morphologies from emulsified nanoparticles to cubosomes and multilamellar liposomes. When they were integrated within the phospholipid/choleterol matrix, the dispersed nanoparticles formed unilamellar liposomes as shown in FIG. 7c (CP-bis (suc-PEG$_3$-oleoyl)).

21.II Dispersions Characterization: Particle Size Distribution

Determination of the particle size distribution of nanoparticle dispersions (colloidosomes) were carried out using a Zetasizer (nano zs, Malvern, England) equipped with a He—Ne Laser (4 mw, 633 nm) and an avalanche photodiode detector. Dynamic light scattering (DLS) analysis was performed on the dispersion in a disposable sizing cuvette with the scattering angle of θ=90° at 25° C. Each measurement was repeated at least three times. The viscosity and RI value of 0.8872cp and 1.330 were used respectively in the data calculation. The size distribution was recorded by intensity.

Figure 8:
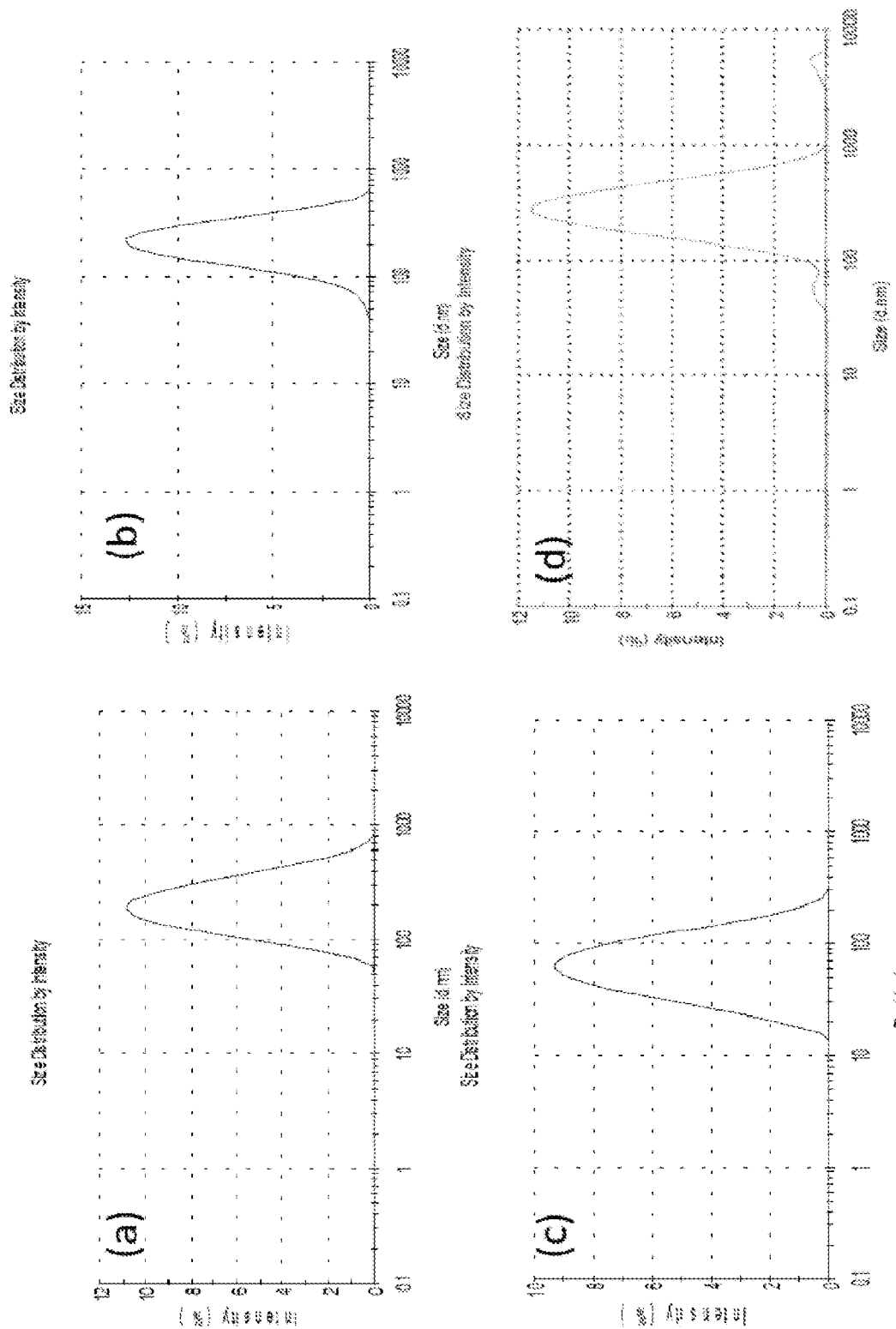
FIG. 8: Particle size distribution of nanoparticle dispersions by intensity determined by dynamic light scattering (DLS), (a): CP-bis (PEG3-oleolyl), (b):CP-bis(suc-aminoPEG3-oleolyl), (c): bis(suc-aminoPEG3-oleolyl)/phospholipid/cholesterol, (d): CP-bis (suc-lys(oleoyl) ethanolamide).

Typical nanoparticle dispersions manufactured from various amphiphiles are shown in FIG. 8 showing homogenous dispersed nanoparticle with average sizes between 50-200 nm.

Demonstration of Biological Activity In Vitro and In Vivo

Example 22: In Vitro Cytotoxicity

The cytotoxicity of CP-prodrug nanoparticles made from sole CP-amphiphiles was evaluated in comparison to native CP in a CFPAC-1 pancreatic cell line.

The cell lines were exposed to media with varying concentrations of the treatments (100-0.2 µM) and incubated for 72 hours. Cell viability was determined using the MTS assay or crystal violate assay and was conducted in triplicate to derive the IC$_{50}$ values.

The treatments resulted in a dose dependent decrease in cell viability in all cell lines. The prodrug CP-bis-PEG$_3$-oleyl nanoparticle, had slightly less IC50 toxicity compared with native CP; 5.1 µM vs 3.6 µM respectively. Reasons for this phenomenon, may be due to a longer window of time required for nanoparticles to completely transform to the active, cytotoxic, free CP. The results of IC$_{50}$ in two other cell lines of MCF7 and CACO2 along with CFPAC1 is listed in Table 4.

TABLE 4

IC$_{50}$ values of CP drug in comparison to CP-prodrug nanoparticles against the CFPAC-1, MCF7, CACO2 and PC3 cell lines for 72 hours. The results show that g CP alone had greater cytotoxicity than the CP- prodrug nanoparticles.

| Cell line | Cisplatin (µM) | CP-nanoparticles CP-bis(suc-PEG3-oleoyl) (µM) |
|---|---|---|
| CFPAC-1 | 3.6 | 5.1 |
| MCF7 | 11.51 | 28.17 |
| CACO2 | 6.74 | 48.97 |

Example 23: Reduction of Pt (IV) Prodrug Amphiphiles to Pt (II)

The Pt (IV) prodrug amphiphiles should undergo reduction inside the cancer cells and generate Pt (II) products to render anticancer activity.

In-situ reduction kinetics was investigated by addition of glutathione (GSH) or ascorbic acid to the nanoparticle dispersions of various Cisplatin, Oxaliplatin and Carboplatin prodrug nanoparticles. The reducing agent was applied at concentrations corresponding to those found in the living cells' environment, e.g. 1 mM ascorbic acid or 2 mM glutathione (GSH).

Dispersed nanoparticles of Pt (IV) prodrug amphiphiles were mixed with GSH, ascorbic acid or their combination. The ratios of the reducing agents to platinum prodrugs were 10:1 or 50:1 for ascorbic acid and 20:1 for GSH. The reduction kinetics was analysed by LC-MS via monitoring the peaks related to each prodrug amphiphile. The prodrugs were detected by negative ions optimised for each platinum amphiphile. The reduction kinetics was plotted as the percentage of the area under the peak of Pt (IV)-prodrug compared to the peak before the addition of the reducing agent against the time of incubation. At each time point 10 µl of a sample withdrawn from the reaction solution was injected directly into a Phenomenex C8 150 mm×2 mm 5 µm Luna column (Phenomenex, Australia). A 100% Methanol solution was used as the mobile phase with a flow rate of 0.5 ml/min for 8 minutes. The sample after the column separation was eluted to the ESI source. The capillary temperature and ion spray voltage were set to 375° C. and 4.60 respectively. The samples were well maintained at a temperature of 37° C. during the entire measurement by incubation in the temperature-controlled auto-sampler. Data was acquired and processed with Xcalibur Quan chromatography software.

Figure 9:
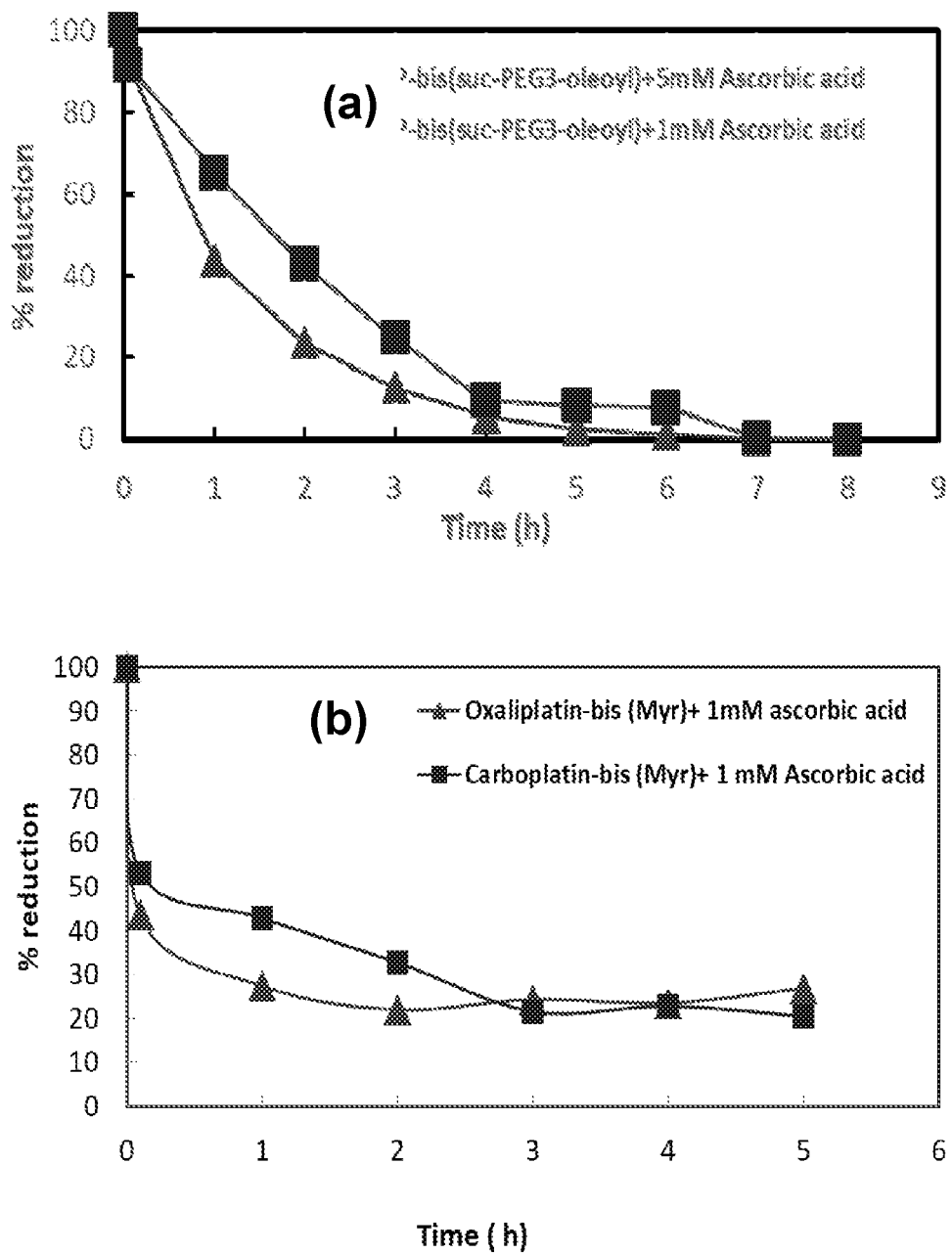
FIG. 9: Reduction kinetics of platinum (IV) prodrug nanoparticles using ascorbic acid as reducing agent (a): CP-bis (suc-aminoPEG3-oleoyl) at two different concentration of 1 and 5 mM of ascorbic acid, the ratio of ascorbic acid to substrate was 50:1 and 10:1; (b): Oxaliplatin-bis (myristoyl) and carboplatin bis (myristoyl) at 1 mM ascorbic acid.

The reduction kinetics of a typical amphiphile, CP-bis (suc-PEG3-oleoyl, at two different concentrations of ascorbic acid, namely 1 mM and 5 mM and prodrug concentration at 0.1 mM was plotted against the incubation time (FIG. 9a). The reduction rate at 5 mM ascorbic acid was slightly greater than 1 mM up to 4 h, however longer incubation time up to 7 h showed similar reduced prodrug at both concentrations. The emergence of the peak related to the hydrophobic ligands (suc-PEG3-Oleoyl) attached to the axial positions of the platinum prodrugs confirmed the reduction of the prodrug to Pt (II) drug.

The 1 mM concentration of ascorbic acid is equivalent to the concentration of the intracellular ascorbic acid in vivo, therefore 1 mM concentration of ascorbic acid was used for reduction of all other platinum prodrug nanoparticles. Typical graphs for two amphiphile prodrugs nanoparticles of Oxaliplatin-bis(myristoyl) and Carboplatin-bis(myristoyl) made at 0.1 mM concentration incorporated within the membrane of liposomal DMPC/cholesterol nanoparticles are also shown in FIG. 9b. The concentration of ascorbic acid to both prodrug amphiphiles was 10:1. The Oxaliplatin prodrug was reduced at a higher rate up to 3 h compared with carboplatin prodrug, However, both carboplatin and oxaliplatin reduced up to 80% at 5 h, and did not change up to 24 h. The maximum reduction of Oxaliplatin and carboplatin amphiphiles was 80% in contrast with 100% for CP amphiphiles. Glutathione reducing agent did not show an active reducing profile for Pt(IV) prodrug nanoparticles.

Example 24: In Vivo Tumour Inhibition

The evaluation of anticancer drugs in vivo is essential as it provides insight into the expected clinical outcomes of a drug. An in vivo evaluation of the anti-cancer efficacy of the CP-prodrug nanoparticles vs. CP was conducted on a resistant MIAPACA-2 (human pancreatic cancer) cell-derived xenograft in NOD-SCID mice. Five mice per group were used in the study and all treatments were administered via an IV injection twice a week for four weeks. The amount of CP administered in the free CP group was 0.75 mg/kg, where the nanoparticles made from CP-bis (suc-PEG$_3$-Oleoyl) and stabilised with 30% PEG4K-oleoyl (FIG. 7b), contained 0.75 mg/kg of equivalent CP.

Figure 10:
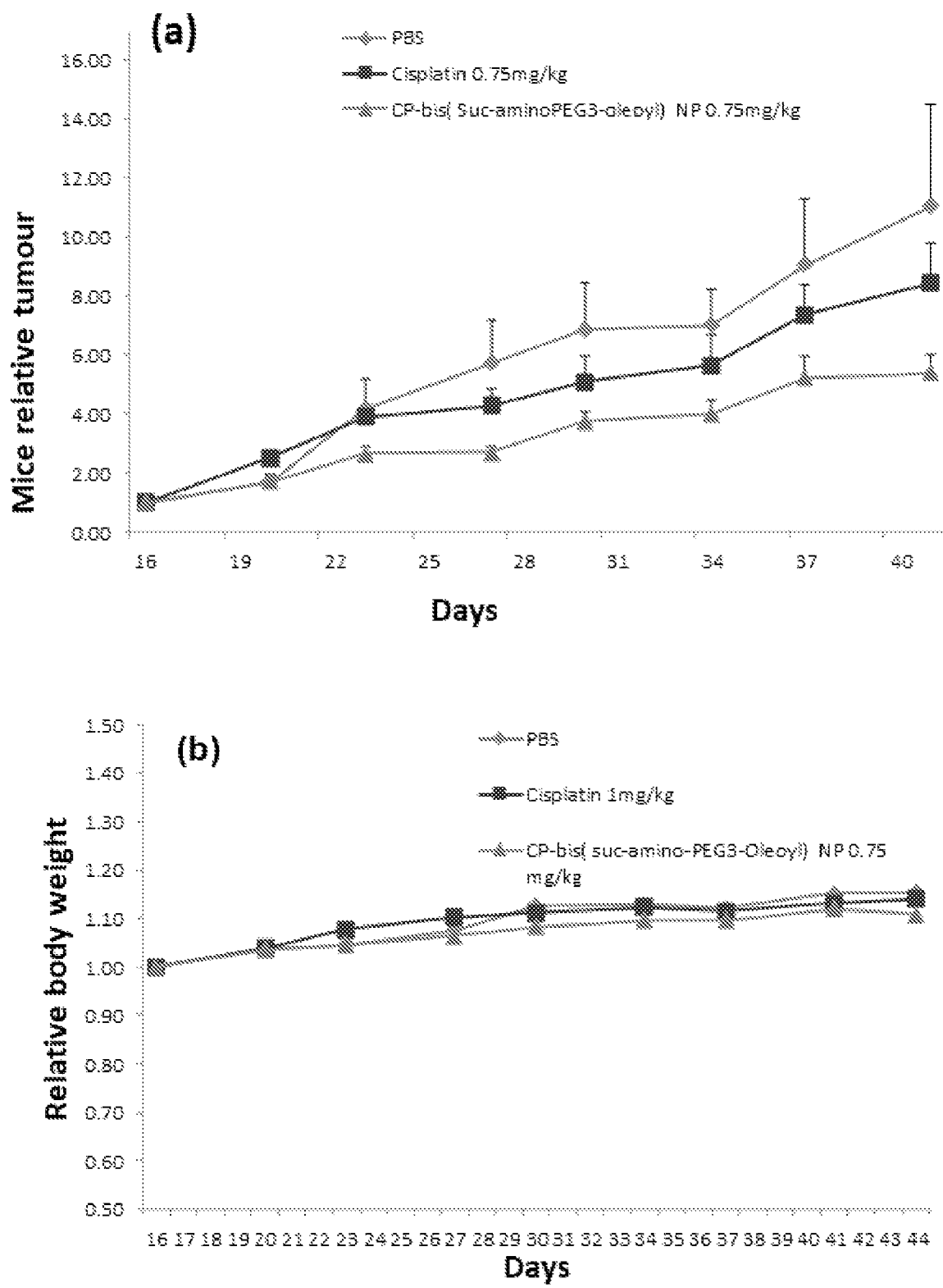
FIG. 10: Tumour inhibition of CP-bis (suc-aminoPEG3-oleoyl) prodrug nanoparticles vs CP and PBS in a resistant MIAPACA-2 pancreatic cancer cell-derived xenograft mouse model. (a): Tumours in all groups (n=5) increased in size, however, the CP-prodrug nanoparticles improved the growth inhibition vs the control group and the CP drug. (b): No body weight loss was observed for all three groups.

Relative tumour volume graphed over time is shown in FIG. 10 (a). The control mice treated with saline alone had a large growth in tumour volume over time. Treatment group with CP-prodrug nanoparticles demonstrated a significant tumour growth inhibition over time as compared with the PBS group (51% of the control group), whereas the free CP group also showed growth inhibition to control PBS group, but less than group treated with nanoparticle. However, the difference was not found to be statistically significant.

The relative body weight of the mice monitored throughout the course of the experiment compared with their initial weights. Body weight of all mice at the conclusion of the experiment in CP-prodrug nanoparticles group, free CP and the control group increased in average by 11%, 14% and 15% respectively (FIG. 10(b)). The difference between groups was not statistically significant. This suggests that a loss of weight was not a side effect of either of the treatments at the dose used in this study.

Figure 11:
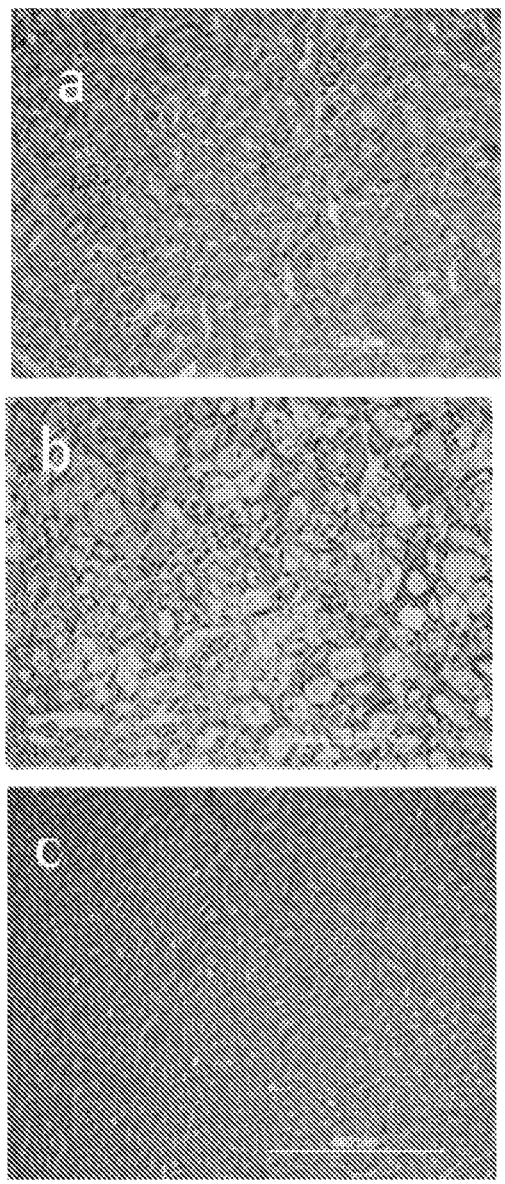
FIG. 11. Histopathology of the kidney. Typical light micrographs of the Kidney sections from each treatment group. Tissues excised from xenograft mouse treated with cisplatin nanoparticles vs. CP and control PBS. Normal tissues were observed with the PBS control mice (a) and mice treated with 0.75 mg/Kg CP-nanoparticles (c), whereas the mice treated with CP drug 0.75 mg/Kg had acute tubular necrosis (b).

Histopathology of the kidney of all treatment groups was also examined. The CP treatment group revealed sever pathological changes in the form of acute tubular necrosis, haemorrhage into many of the glomeruli and swelling of the capillaries (FIG. 11b). However, the treatment group with CP-prodrug NPs (FIG. 11c) showed only mild precipitate in the glomeruli and inflammatory infiltrate, compared with the normal Kidney tissue in PBS group (FIG. 11a).

In another study a dual drug chemotherapeutic prodrug nanoparticle was employed to treat a CFPAC-1 (human pancreatic cancer) cell line-derived xenograft in NOD-SCID gamma mouse (NSG) over 28 days. The nanoparticles were self-assembled from DMPC/cholesterol/Gemcitabine Phytanyl [PCT/AU2019/050363] and CP-bis (myristoyl) in this invention) at a ratio of 75.86/8.35/12.62/3.17 (w/w %). The dose of active Gem and CP dose in the dual nanoparticle group were 4.5 mg/Kg and 1 mg/Kg of the respective equivalent drugs. Mice in Gem nanoparticle group were treated with NPs containing 4.5 mg/Kg of active Gem only. The composition of the Gem-nanoparticle group was 73.52/8.10/18.38 (w/w %) of DMPC/cholesterol/Gemcitabine-Phytanyl respectively. The control groups were injected with the commercially available free Gemcitabine at 100 mg/Kg and PBS (vehicle control). Gemcitabine group were administered by intraperitoneal (IP) injection due to high toxicity of IV injection. 24 mice were used in this study, treating 6 mice/group.

Figure 12:
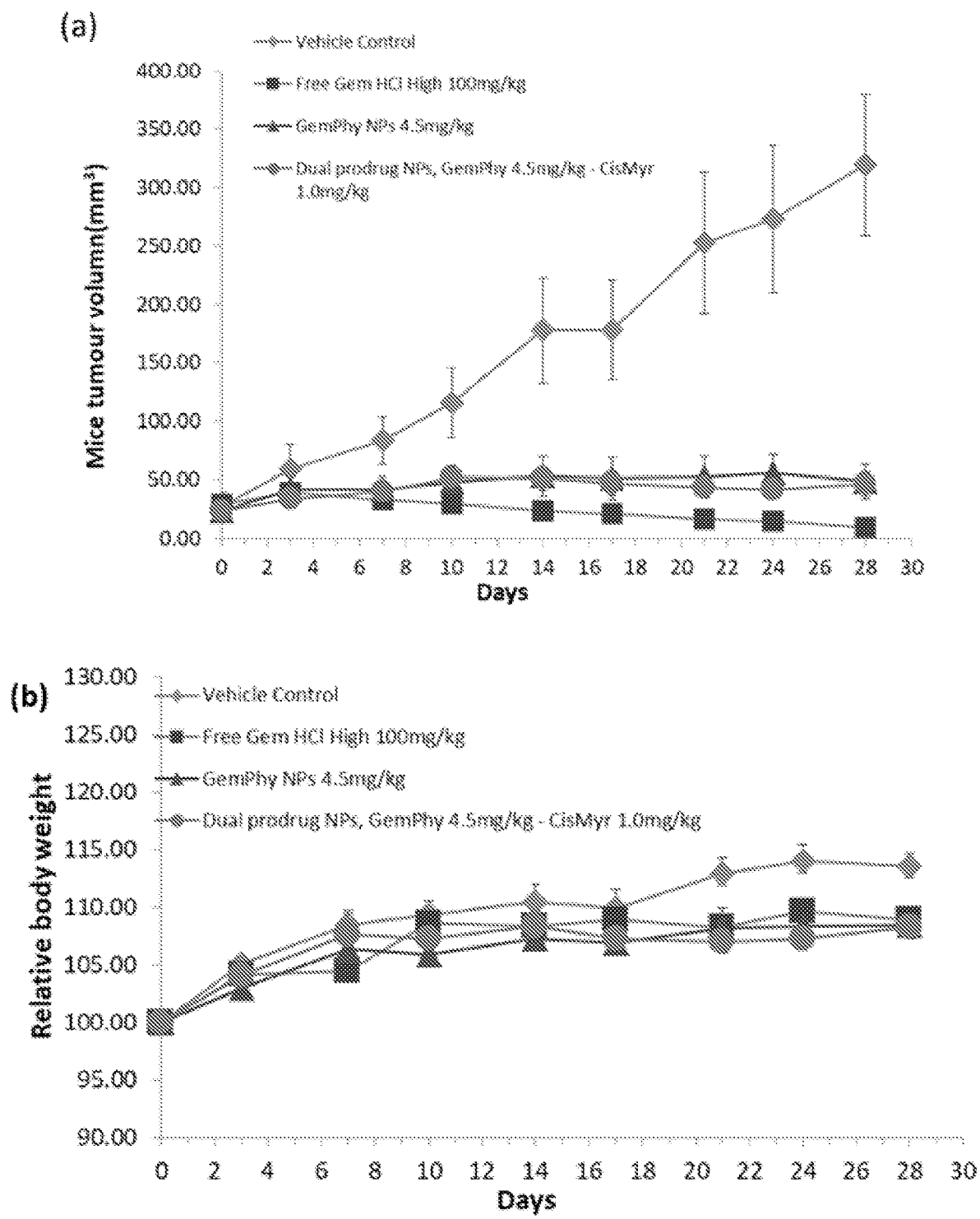
FIG. 12: Tumour growth inhibition in a CFPAC-1 pancreatic cancer cell-derived xenograft mouse model in response to a dual prodrug liposomal nanoparticle (NPs). Groups of 6 mice were treated with 1) dual prodrug NPs (Gem-phytanyl (4.5 mg/Kg), CP-bis(myristoyl) 1 mg/Kg/phospholipid/cholesterol) vs, 2) single prodrug NPs (Gem-Phytanyl (4.5 mg/Kg)/phospholipid/cholesterol), 3) Gemcitabine drug at 100 mg/Kg and 4) PBS vehicle control group, all groups were injected twice a week for 4 weeks. (a): Average tumour size vs. time; Gem control group with significantly higher concentration of Gem (>22-fold of active Gem compared with the Gem active drugs in nanoparticle groups) reduced the size of tumour significantly better than other groups. The tumour growth inhibition of mice treated with the dual drug NPs or Gem only NPs with 4.5% of active Gem of common treatment in mice had significant growth inhibition, however, did not reduce the original tumour size. The dual drug NPs had slightly better inhibition compared with Gem only NPs; (b): No body weight loss was observed for all groups.

Tumour volume was graphed over time and displayed in FIG. 12(a). The control mice treated with saline alone had a large growth in tumour size over 28 days of the study. The mice treated with commercially-available Gemcitabine at a maximum dose of 100 mg/Kg, commonly-used for the treatment of xenograft rodent, significantly reduced the tumour volume. Both nanoparticle groups at a very low dose of 4.5% of the active Gem or dual drug nanoparticles containing 4.5 mg/Kg of equivalent Gem+1 mg/Kg equivalent CP, significantly inhibited the tumour growth compared with the control PBS group. This study, however, did not show any significant improvement in using dual drug-NPs over Gem NPs for the pancreatic xenografts. This may be due to the high sensitivity and sound response of this xenograft model towards Gemcitabine drug only. The body weight of all the mice increased over time compared with their initial weights, shown in FIG. 12(b).

REFERENCES

1) Peterson M. J, Melander, F, Vikbjerg, A. S., Peterson, S. A., Madsen, M. W., Bio-Beddst APS, WO2011032563A1.
2) WO2006098496A1, Coordinated compound composed of diaminocyclohexane platinum (II) and block copolymer and anti-cancer agent comprising the same
3) Gu F., Zhang L., Teply, B. A., Mann, N., Wang A., Aleksandar F. Radovic-Moreno A. F., Langer R., and Farokhzad O. C., Precise engineering of targeted nanoparticles by using self-assembled biointegrated block copolymers, PNAS, 2008, 105,7, P 2586-2591.
4) Yang S. C., Lu, L. F., Cai Y., Zhu, J. B. Liang B. W., Yang Z., Body distribution in mice intravenously injected camptothecin solid lipid nanoparticles and targeting effect on brain. Journal of controlled release, 1999, 3, 299-307.
5) Jin Y., Tong L, Ai P., Li M. and Hou X. Self-assembled drug delivery systems 1. properties and in vitro/in vivo behaviour of acyclovir self-assembled nanoparticles (SAN), International Journal of Pharmaceutics, 2006, 309: 199-207
6) Brannon-Peppas L. Blanchtte J. O., Nanopartiles and targeted systems for cancer theapy, Adv drug delivery reviews, 2012, 64, 206-212

7) Mehnert W., Maeder K., Solid lipid nanoparticles: production, characterisation and applications, Adv drug delivery rev. 2001, 472-3):165-96
8) de Campo L, Yaghmur A, Sagalowicz L, Leser M E, Watzke H, Glatter O. Reversible Phase Transitions in Emulsified Nanostructured Lipid Systems. Langmuir. 2004; 20(13):5254-61.

The invention claimed is:

1. A composition, comprising water and a prodrug amphiphile of general formula (I):

$$X_1-Y_1-A-(Y_2)_n-X_2 \quad (I)$$

wherein A is an oxidised platinum (IV)-based therapeutically active agent;

$Y_1$ and $Y_2$ are independently selected ester and carbonate cleavable bonds between $X_1$ and $X_2$, respectively, and A;

n=0 or 1, wherein when $X_2$ is a substituent according to formula (b) or formula (c), n is 1;

$X_1$ is selected from the group consisting of a substituent according to formula (b) and a substituent according to formula (c):

$$R-S- \quad (b)$$

$$R-S-L- \quad (c)$$

$X_2$ is selected from the group consisting of H and $X_1$;

wherein

R is selected from the group consisting of alkyl, alkenyl, alkynyl, branched alkyl, branched alkenyl, branched alkynyl, substituted alkyl, substituted alkenyl, substituted alkynyl groups, and alpha-tocopherol; wherein R has a chain length equivalent to 14 to 20 carbon atoms;

S is selected from the group consisting of (ethyleneglycol)$_m$, wherein m=1-6, lysine, and an ethanolamide functionalised lysine;

L is a cleavable functional linker group that is selected from the group consisting of succinic anhydride, maleic anhydride, and glutaric anhydride, which is covalently attached to S—R at one attachment site and to the therapeutically active agent A at a second attachment site via the bond Y to A;

wherein the prodrug amphiphile and water form a self-assembled bulk lyotropic liquid crystalline mesophase structure or its dispersed nanoparticles (colloidosomes), possessing the same internal nanostructure of the bulk phase, under physiological conditions in which the temperature is 35° C. to 37° C., a mesophase structure selected from the group consisting of: lamellar, inverse bicontinuous cubic phase, inverse micellar and sponge phases, and wherein the prodrug amphiphile nanoparticles has an average size ranging from 10 to 500.

2. The composition according to claim 1, wherein the oxidised platinum (IV)-based therapeutically active agent is selected from the group consisting of cisplatin, oxaliplatin, and carboplatin.

3. The composition according to claim 1, wherein the general formula (I) is a compound according to formula (II):

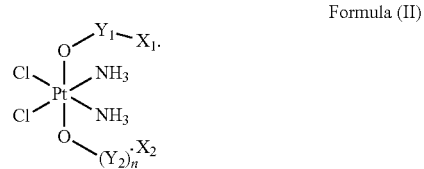

Formula (II)

4. The composition according to claim 3, wherein the compound according to Formula (II) is selected from the group consisting of:

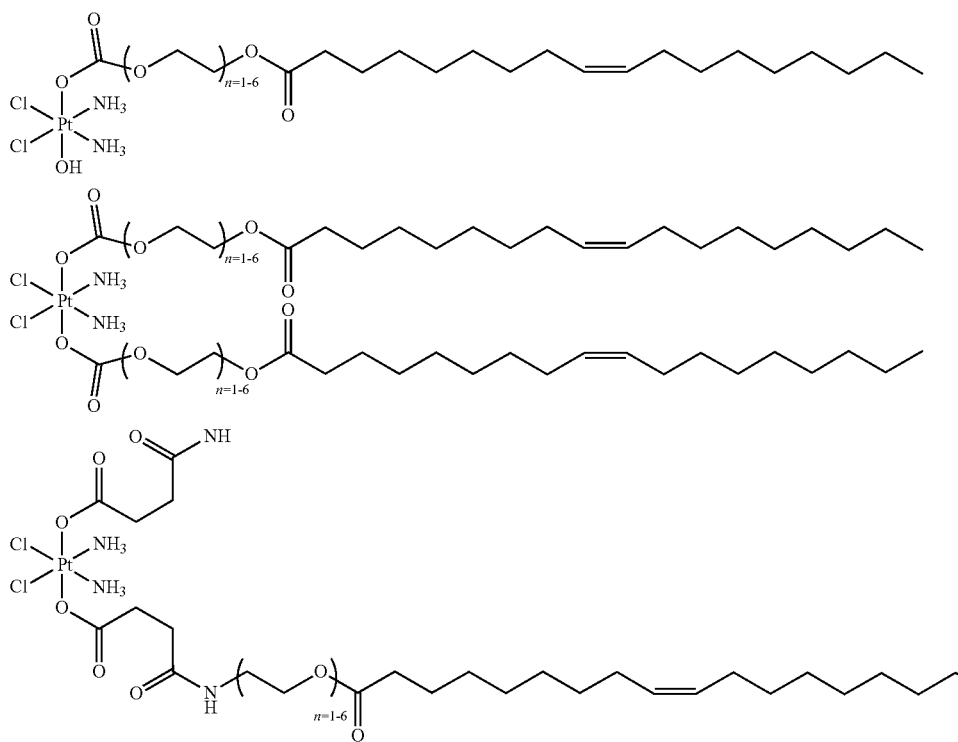

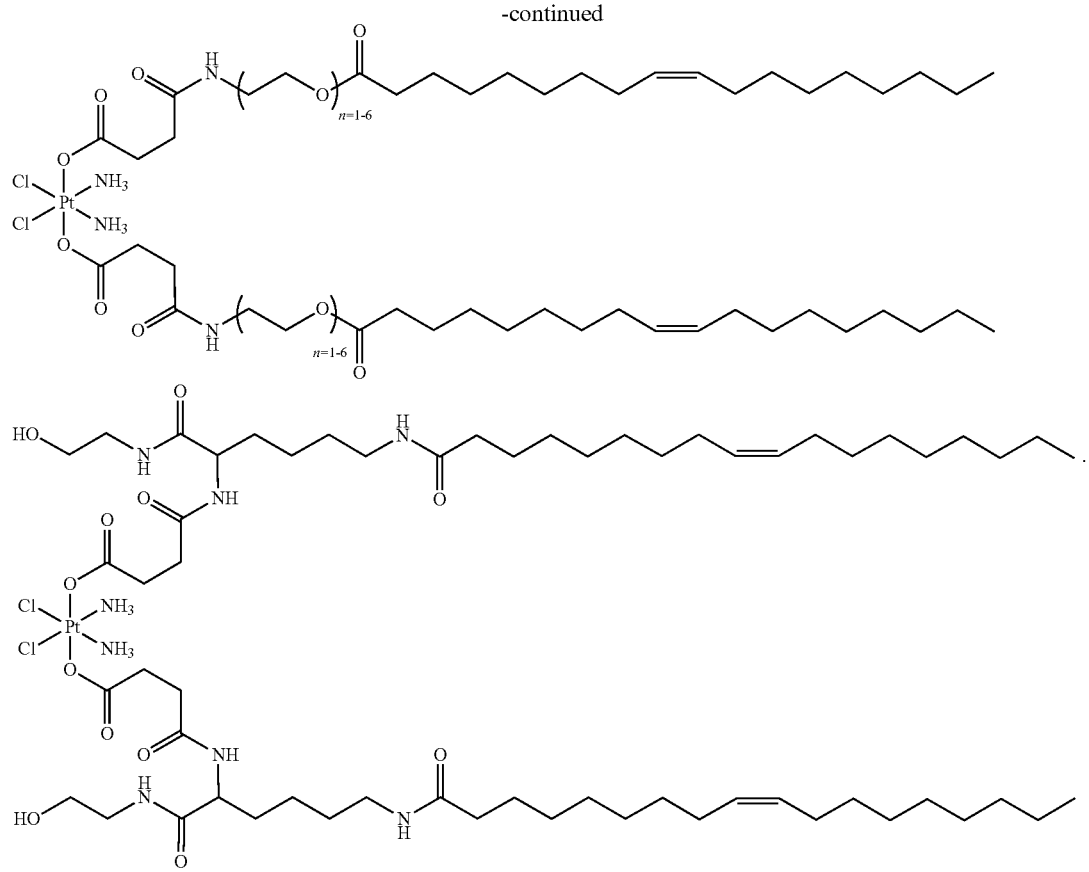

5. The composition according to claim 1, wherein the structure exhibits a mesophase under physiological conditions selected from the group consisting of: lamellar, inverse bicontinuous cubic phase, inverse micelles and sponge phases.

6. The composition according to claim 5, wherein the mesophase exhibited is liquid crystalline lamellar or inverse phases.

7. The composition according to claim 5, further comprising a component selected from the group consisting of: phospholipid, cholesterol, glycerol lipid, other prodrug amphiphile, hydrophobic drugs and combinations thereof.

8. A method of modulating the bioavailability and release of a platinum-based therapeutically active agent or an agent capable of being metabolised in vivo to a platinum-based therapeutically active agent, the method comprising covalently linking an oxidised platinum (IV)-based therapeutically active agent, A, to at least one tail component, X, to form an amphiphile capable of self-assembling into a self-assembled structure under physiological conditions, and wherein the amphiphile is cleavable in vivo to release the therapeutically active agent, wherein the amphiphile is of general formula (I):

wherein
$Y_1$ and $Y_2$ are independently selected ester and carbonate cleavable bonds between $X_1$ and $X_2$, respectively, and A;
n=0 or 1, wherein when $X_2$ is a substituent according to formula (b) or formula (c), n is 1;

$X_1$ is selected from the group consisting of a substituent according to formula (b) and a substituent according to formula (c):

$$R-S- \quad (b)$$

$$R-S-L- \quad (c)$$

$X_2$ is selected from the group consisting of H and $X_1$; wherein
R is selected from the group consisting of alkyl, alkenyl, alkynyl, branched alkyl, branched alkenyl, branched alkynyl, substituted alkyl, substituted alkenyl, substituted alkynyl groups, and alpha-tocopherol; wherein R has a chain length equivalent to 14 to 20 carbon atoms;
S is selected from the group consisting of (ethylene glycol)$_m$, wherein m=1-6, an amino acid, and an ethanolamide functionalised amino acid;
L is a cleavable functional linker group that is selected from the group consisting of succinic anhydride, maleic anhydride, and glutaric anhydride, which is covalently attached to S—R at one attachment site and to the therapeutically active agent A at a second attachment site via the bond Y to A;
wherein the prodrug amphiphile and water form a self-assembled bulk lyotropic liquid crystalline mesophase structure or its dispersed nanoparticles (colloidosomes), possessing the same internal nanostructure of the bulk phase, under physiological conditions in which the temperature is 35° C. to 37° C., a mesophase structure selected from the group consisting of: lamellar, inverse bicontinuous cubic phase, inverse micellar and sponge phases, and wherein the prodrug amphiphile nanoparticles has an average size ranging from 10 to 500 nm.

9. A method according to claim 8, wherein the amphiphile of general formula (I) is a compound according to formula (II):

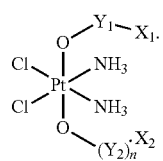

Formula (II)

10. A method according to claim 8, wherein the amphiphile is a substrate for an enzymatic or a chemical reaction that promotes formation of an active form of the therapeutic agent.

11. The method according to claim 8, wherein the prodrug amphiphile nanoparticles has an average size ranging from 10 to 200 nm.

12. The composition according to claim 5, wherein the mesophase structure is a liquid crystalline lamellar or inverse colloidosomes (nanoparticles).

13. The composition according to claim 4, wherein the structure exhibits a mesophase under physiological conditions selected from the group consisting of: lamellar, inverse bicontinuous cubic phase, inverse micelles and sponge phases.

14. The composition according to claim 3, wherein the structure exhibits a mesophase under physiological conditions selected from the group consisting of: lamellar, inverse bicontinuous cubic phase, inverse micelles and sponge phases.

15. The composition according to claim 2, wherein the structure exhibits a mesophase under physiological conditions selected from the group consisting of: lamellar, inverse bicontinuous cubic phase, inverse micelles and sponge phases.

16. The composition according to claim 1, wherein the structure exhibits a mesophase under physiological conditions selected from the group consisting of: lamellar, inverse bicontinuous cubic phase, inverse micelles and sponge phases.

\* \* \* \* \*